US008632780B2

(12) United States Patent
Vogel et al.

(10) Patent No.: US 8,632,780 B2
(45) Date of Patent: Jan. 21, 2014

(54) HUMAN COMPLEMENT C3 DERIVATES WITH COBRA VENOM FACTOR-LIKE FUNCTION

(75) Inventors: Carl-Wilhelm Vogel, Honolulu, HI (US); David C. Fritzinger, Honolulu, HI (US)

(73) Assignee: University of Hawaii, Honolulu, HI (US)

( * ) Notice: Subject to any disclaimer, the term of this patent is extended or adjusted under 35 U.S.C. 154(b) by 1054 days.

(21) Appl. No.: 11/579,235

(22) PCT Filed: Apr. 29, 2005

(86) PCT No.: PCT/US2005/015119
§ 371 (c)(1),
(2), (4) Date: Aug. 15, 2007

(87) PCT Pub. No.: WO2005/107785
PCT Pub. Date: Nov. 17, 2005

(65) Prior Publication Data
US 2008/0311132 A1    Dec. 18, 2008

Related U.S. Application Data

(60) Provisional application No. 60/567,069, filed on Apr. 30, 2004, provisional application No. 60/653,247, filed on Feb. 14, 2005, provisional application No. 60/667,352, filed on Mar. 31, 2005.

(51) Int. Cl.
| *A01K 39/00* | (2006.01) |
| *A61K 35/14* | (2006.01) |
| *A61K 38/16* | (2006.01) |
| *C07K 1/00* | (2006.01) |
| *C07K 14/00* | (2006.01) |
| *C07K 16/00* | (2006.01) |
| *C07K 17/00* | (2006.01) |

(52) U.S. Cl.
USPC .................. 424/185.1; 530/350; 530/380

(58) Field of Classification Search
None
See application file for complete search history.

(56) References Cited

U.S. PATENT DOCUMENTS

| 4,661,347 | A | 4/1987 | Muller-Eberhard et al. |
| 5,714,344 | A | 2/1998 | Ollert et al. |
| 5,773,243 | A | 6/1998 | Fritzinger et al. |
| 5,849,297 | A | 12/1998 | Harrison et al. |
| 6,221,657 | B1 | 4/2001 | Harrison et al. |
| 6,303,754 | B1 | 10/2001 | Vogel et al. |
| 6,607,897 | B2 | 8/2003 | Vogel et al. |
| 7,553,931 | B2 | 6/2009 | Kölln et al. |
| 2005/0079585 | A1 | 4/2005 | Kolln et al. |
| 2008/0234191 | A1 | 9/2008 | Vogel et al. |
| 2009/0270324 | A1 | 10/2009 | Kolln et al. |
| 2010/0179092 | A1 | 7/2010 | Fritzinger et al. |

FOREIGN PATENT DOCUMENTS

| WO | WO-2005/003159 A1 | 1/2005 |
| WO | WO-2005/107785 A2 | 11/2005 |
| WO | WO-2005/107785 A3 | 11/2005 |
| WO | WO-2008/060634 A2 | 5/2008 |

OTHER PUBLICATIONS

Fritzinger et al. 'Molecular cloning and derived primary structure of cobra venom factor.' Proc. Natl. Acad. Sci. 91:12775-12779, 1994.*
Kock et al. 'Structure and Function of Recombinatn Cobra Venom Factor.' J. Biol. Chem. 279(29):30836-30843, 2004.*
Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 1994.491-495.*
Ngo et al. 'Computational Complexity, Protein Structure Prediction,and the Levinthal Paradox'. The Protein Folding Problem and Tertiary Structure Prediction. Ed° K. Merz and S. Le Grand. Boston: Birkhauser, 1994.491-495.*
Burgess et al. 'Possible Dissociation of the Heparin-binding and Mitogenis Activities of Heparin-binding (Acidis Fibroblast) Growth Factor-1 from Its Receptor-binding Activites by Site-directed Mutagenesis of a Single Lysine Residue.' J. Cell. Biol. 111:2129-2138, 1990.*
Lazar et al. 'Transforming Growth Factor alpha:Mutation of Aspartic Acid 47 and Leucine 48 Results in Different Biological Activities.' Mol. Cell. Biol. 8(3):1247-1252, 1988.*
Skolnick et al. 'From genes to protein structure and function: novel applications of computational approaches in the genomic era.' Trends in Biotech. 18:34-39, 2000.*
Attwood et al. 'The Babel of Bioinformatics.' Science. 290(5491):471-473.*
Vogel et al. 'Cobra venom factor: Structure, function, and humanization for therapeutic complement depletion.' Toxicon 56:1198-1222, 2010.*
Alsenz, J. et al. (Jan.-Feb. 1992). "Phylogeny of the Third Component of Complement, C3: Analysis of the Conservation of Human CR1, CR2, H, and B Binding Sites, Concanavalin A Binding Sites, and Thiolester Bond in the C3 From Different Species," *Developmental and Comparative Immunology* 16(1):63-76.
Carporale, L.H. et al. (May 1981). "A Fluorescent Assay for Complement Activation," *The Journal of Immunology* 126(5):1963-1965.

(Continued)

*Primary Examiner* — Nora Rooney
(74) *Attorney, Agent, or Firm* — Morrison & Foerster LLP

(57) ABSTRACT

A modified human complement C3 protein (C3) is disclosed comprising a substitution of a portion of a human C3 protein, with a corresponding portion of a Cobra Venom Factor protein (CVF) which results in a human C3 protein with CVF functions, but with substantially reduced immunogenicity. Advantageously, the C3 protein can be manipulated to contain at least one of the following CVF functions: increased stability of the C3 convertase and increased resistance to the actions of factors H and/or I. A large number of hybrid C3 proteins containing substitutions in the C-terminal portion of the alpha chain of C3 are presented and tested for the above functions. Methods of treatment of diseases such as reperfusion injury, autoimmune diseases, and other diseases of increased complement activation are presented as well as methods of increasing the effectiveness of gene therapeutics and other therapeutics.

33 Claims, 19 Drawing Sheets

(56) References Cited

OTHER PUBLICATIONS

Chen, C. et al. (Aug. 1987). "High-Efficiency Transformation of Mammalian Cells by Plasmid DNA," *Molecular and Cellular Biology* 7(8):2745-2752.

Cochrane, C.G. et al. (Jul. 1970). "Depletion of Plasma Complement in Vivo by a Protein of Cobra Venom: Its Effect on Various Immunologic Reactions," *The Journal of Immunology* 105(1):55-69.

Daha, M.R. et al. (Aug. 1976). "C3 Requirements for Formation of Alternative Pathway C5 Convertase," *The Journal of Immunology* 117(2):630-634.

Fecke, W. et al. (Feb. 1998). "Expression of Factor I-Resistant Mutants of the Human Complement Component C3 in Heterologous Systems," *Xenotransplantation* 5(1):29-34.

Fritzinger, D.C. et al. (Sep. 2003). "Functional Characterization of Cobra Venom Factor/Cobra C3 Hybrid Proteins," *Molecular Immunology* 40(2-4):199, Abstract 58.

Grunwald, T. et al. (1993). "Cobra Venom Factor: An Intact β-Chain is not Required for Activity," *Molecular Immunology* 30(Supp.1):13.

Ho, S.N. et al. (1989). "Site-Directed Mutagenesis by Overlap Extension Using the Polymerase Chain Reaction," *Gene* 77(1):51-59.

Kock, M.A. et al. (Jul. 16, 2004). "Structure and Function of Recombinant Cobra Venom Factor," *The Journal of Biological Chemistry* 279(29):30836-30843.

Kölln, J. et al. (May 2004). "Functional Analysis of Cobra Venom Factor/Human C3 Chimeras Transiently Expressed in Mammalian Cells," *Molecular Immunology* 41(1):19-28.

Köln, J. et al. (Apr. 15, 2005). "Engineering of Human Complement Component C3 for Catalytic Inhibition of Complement," *Immunology Letters* 98(1):49-56.

Kölln, J. et al. (2004). "Complement Inactivation by Recombinant Human C3 Derivatives," *The Journal of Immunology* 173:5540-5545.

Lambris, J.D. et al. (Jun. 15, 1996). "Dissection of CR1, Factor H, Membrane Cofactor Protein, and Factor B Binding and Functional Sites in the Third Complement Component," *The Journal of Immunology* 156(12)9:4821-4832.

Müller-Eberhard, H.J. (1988). "Molecular Organization and Function of the Complement System," *Ann. Rev. Biochem.* 57:321-347.

Oran, A.E. et al. (Feb. 19, 1999). "Identification of Residues within the 727-767 Segment of Human Complement Component C3 Important for Its Interaction with Factor H and with Complement Receptor 1 (CR1, CD35)," *The Journal of Biological Chemistry* 274(8):5120-5130.

Pangburn, M.K. et al. (May 1, 2000). "Molecular Mechanisms of Target Recognition in an Innate Immune System: Interactions Among H, C3b, and Target in the Alternative Pathway of Human Complement," *The Journal of Immunology* 164(9): 4742-4751.

Petrella, E.C. et al. (1987). "Antibody Conjugates With Cobra Venom Factor—Synthesis and Biochemical Characterization," *The Journal of Immunological Methods* 104(1-2):159-172.

Vogel, C-W et al. (Jun. 2004). "Recombinant Cobra Venom Factor," *Molecular Immunology* 41(2/3):191-199.

Vogel, C-W. et al. (Jul. 25, 1982). "The Cobra Venom Factor-Dependent C3 Convertase of Human Complement—A Kinetic and Thermodynamic Analysis of a Protease Acting on its Natural High Molecular Weight Substrate," *The Journal of Biological Chemistry* 257(14):8292-8299.

Vogel, C.W. et al. (1984). "Cobra Venom Factor: Improved Method for Purification and Biochemical Characterization," *Journal of Immunological Methods* 73(1):203-220.

Diefenbeck, M. et al. (Nov. 1998). "Intravital Microscopic Investigation of Xenogeneic Microcirculation and Impact of Complement Depletion by Cobra Venom Factor," *Xenotransplantation* 5(4):262-273.

Hoffman, C. et al. (Jan. 1, 1998). "Baculovirus-mediated Gene Transfer in the Presence of Human Serum or Blood Facilitated by Inhibition of the Complement System," *Gene Therapy* 5:531-536.

Juhl, H. et al. (Nov. 1997). "Additive Cytotoxicity of Different Monoclonal Antibody-Cobra Venom Factor Conjugates for Human Neuroblastoma Cells," *Immunobiology* 197(5):444-459.

Kölln, J. (2003). *Humanisierung von Cobra Venom Factor*, Dissertation zur Erlangung des Doktorgrades des Fachbereiches Chemie der Universität [Dissertation for Completion of a Doctorate from the Chemistry Department of the University of Hamburg], University of Hamburg: Hamburg, Germany, 197 pages.

Fritzinger, D.C. et al. (2010). "Complement Depletion with Humanized Cobra Venom Factor in a Mouse Model of Age-Related Macular Degeneration," *Adv. Exp. Med. Biol.* 703:151-162.

Fritzinger, D.C. et al. (2008). "Derivatives of Human Complement Component C3 for Therapeutic Complement Depletion: A Novel Class of Therapeutic Agents," *Adv. Exp. Med. Biol.* 632:293-307.

Fritzinger, D. et al. (Sep./Oct. 2008). "A Novel Concept for the Treatment of Paroxysmal Nocturnal Haemoglobinuria (PNH): Complement Depletion with a Human C3 Derivative with Cobra Venom Factor-like Activity Prevents Lysis of PNH Erythrocytes," *Mol. Immunol.* 45:4177 ($22^{nd}$ International Complement Workshop, Basel, Switzerland).

Fritzinger, D. et al. (Sep./Oct. 2008). "Human C3/Cobra Venom Factor Hybrid Proteins for Therapeutic Complement Depletion: In Vivo Activity and Lack of Toxicity in Primates," *Mol. Immunol.* 45:4112 ($22^{nd}$ International Complement Workshop, Basel, Switzerland).

Gorsuch, W.B. et al. (Dec. 2009, e-pub. Sep. 10, 2009). "Humanized Cobra Venom Factor Decreases Myocardial lschemia-Reperfusion Injury," *Mol. Immunol.* 47(2-3):506-510.

Takahashi, K. et al. (Dec. 2011, e-pub. Oct. 5, 2011). "Complement 3 is Involved with Ventilator-Induced Lung Injury," *Int. Immunopharmacol.* 11(12):2138-2143.

Vogel, C.-W. et al. (Dec. 15, 2010, e-pub. Apr. 22, 2010). "Cobra Venom Factor: Structure, Function, and Humanization for Therapeutic Complement Depletion," *Toxicon* 56(7):1198-1222.

Wang, S.-Y. et al. (Dec. 17, 2009, e-pub. Oct. 5, 2009). "Depletion of the C3 Component of Complement Enhances the Ability of Rituximab-coated Target Cells to Activate Human NK Cells and Improves the Efficacy of Monoclonal Antibody Therapy in an in Vivo Model," *Blood* 114(26):5322-5330.

\* cited by examiner

| Hybrid Protein | C3 Region Replaced with CVF | % Homology to Human C3 | Complement Depletion in NHS* | Convertase Formation (fB Cleavage)* | C3 Cleavage* | fH and I Cleavage |
|---|---|---|---|---|---|---|
| HC3-1550 | 1550-1663 | 96% identical, 97% similar | + | ++++ | +++ | Slower than C3 |
| HC3-1504 | 1504-1663 | 95% identical, 96% similar | + | +++ | ++ | Slower than C3 |
| HC3-1348 | 1348-1663 | 90% identical, 94% similar | ++ | + | ++++ | Slower than C3 |
| HC3-1496 | 1496-1663 | 94% identical, 96% similar | ++ | +++ | ++++ | Slower than C3 |
| HC3-1550/1617 | 1550-1617 | 97% identical, 98% similar | - | ++++ | +++/++§ | ? |
| CVF | NA | 49% identical, 68% similar | +++ | +++ | +++ | No |
| Human C3b | NA | 100% | - | ++++ | - | Yes |

*+++ is defined to activity equivalent to CVF
§ Reaction stops after ~15 minutes

SEQUENCE LISTING

<160> NUMBER OF SEQ ID NOS: 24

<210> SEQ ID NO 1
<211> LENGTH: 5067
<212> TYPE: DNA
<213> ORGANISM: Homo sapiens
<220> FEATURE:
<221> NAME/KEY: CDS
<222> LOCATION: (61)...(5052)

<400> SEQUENCE: 1

| | | | | | |
|---|---|---|---|---|---|
| ctcctcccca tcctctccct ctgtccctct gtccctctga ccctgcactg tcccagcacc | | | | | 60 |
| atg gga ccc acc tca ggt ccc agc ctg ctg ctc ctg cta cta acc cac<br>Met Gly Pro Thr Ser Gly Pro Ser Leu Leu Leu Leu Leu Thr His<br>1                         5                       10                     15 | | | | | 108 |
| ctc ccc ctg gct ctg ggg agt ccc atg tac tct atc atc acc ccc aac<br>Leu Pro Leu Ala Leu Gly Ser Pro Met Tyr Ser Ile Ile Thr Pro Asn<br>                  20                       25                       30 | | | | | 156 |
| atc ttg cgg ctg gag agc gag gag acc atg gtg ctg gag gcc cac gac<br>Ile Leu Arg Leu Glu Ser Glu Glu Thr Met Val Leu Glu Ala His Asp<br>               35                       40                       45 | | | | | 204 |
| gcg caa ggg gat gtt cca gtc act gtt act gtc cac gac ttc cca ggc<br>Ala Gln Gly Asp Val Pro Val Thr Val Thr Val His Asp Phe Pro Gly<br>50                      55                       60 | | | | | 252 |
| aaa aaa cta gtg ctg tcc agt gag aag act gtg ctg acc cct gcc acc<br>Lys Lys Leu Val Leu Ser Ser Glu Lys Thr Val Leu Thr Pro Ala Thr<br>65                      70                       75                   80 | | | | | 300 |
| aac cac atg ggc aac gtc acc ttc acg atc cca gcc aac agg gag ttc<br>Asn His Met Gly Asn Val Thr Phe Thr Ile Pro Ala Asn Arg Glu Phe<br>                  85                       90                       95 | | | | | 348 |
| aag tca gaa aag ggg cgc aac aag ttc gtg acc gtg cag gcc acc ttc<br>Lys Ser Glu Lys Gly Arg Asn Lys Phe Val Thr Val Gln Ala Thr Phe<br>                  100                      105                      110 | | | | | 396 |
| ggg acc caa gtg gtg gag aag gtg gtg ctg gtc agc ctg cag agc ggg<br>Gly Thr Gln Val Val Glu Lys Val Val Leu Val Ser Leu Gln Ser Gly<br>                  115                      120                      125 | | | | | 444 |
| tac ctc ttc atc cag aca gac aag acc atc tac acc cct ggc tcc aca<br>Tyr Leu Phe Ile Gln Thr Asp Lys Thr Ile Tyr Thr Pro Gly Ser Thr<br>130                      135                      140 | | | | | 492 |
| gtt ctc tat cgg atc ttc acc gtc aac cac aag ctg cta ccc gtg ggc<br>Val Leu Tyr Arg Ile Phe Thr Val Asn His Lys Leu Leu Pro Val Gly<br>145                      150                      155                      160 | | | | | 540 |
| cgg acg gtc atg gtc aac att gag aac ccg gaa ggc atc ccg gtc aag<br>Arg Thr Val Met Val Asn Ile Glu Asn Pro Glu Gly Ile Pro Val Lys<br>                  165                      170                      175 | | | | | 588 |
| cag gac tcc ttg tct tct cag aac cag ctt ggc gtc ttg ccc ttg tct<br>Gln Asp Ser Leu Ser Ser Gln Asn Gln Leu Gly Val Leu Pro Leu Ser<br>                  180                      185                      190 | | | | | 636 |
| tgg gac att ccg gaa ctc gtc aac atg ggc cag tgg aag atc cga gcc<br>Trp Asp Ile Pro Glu Leu Val Asn Met Gly Gln Trp Lys Ile Arg Ala<br>                  195                      200                      205 | | | | | 684 |
| tac tat gaa aac tca cca cag cag gtc ttc tcc act gag ttt gag gtg<br>Tyr Tyr Glu Asn Ser Pro Gln Gln Val Phe Ser Thr Glu Phe Glu Val<br>210                      215                      220 | | | | | 732 |
| aag gag tac gtg ctg ccc agt ttc gag gtc ata gtg gag cct aca gag<br>Lys Glu Tyr Val Leu Pro Ser Phe Glu Val Ile Val Glu Pro Thr Glu<br>225                      230                      235                      240 | | | | | 780 |
| aaa ttc tac tac atc tat aac gag aag ggc ctg gag gtc acc atc acc<br>Lys Phe Tyr Tyr Ile Tyr Asn Glu Lys Gly Leu Glu Val Thr Ile Thr<br>                  245                      250                      255 | | | | | 828 |

-continued

| | | |
|---|---|---|
| gcc agg ttc ctc tac ggg aag aaa gtg gag gga act gcc ttt gtc atc<br>Ala Arg Phe Leu Tyr Gly Lys Lys Val Glu Gly Thr Ala Phe Val Ile<br>260                            265                    270 | | 876 |
| ttc ggg atc cag gat ggc gaa cag agg att tcc ctg cct gaa tcc ctc<br>Phe Gly Ile Gln Asp Gly Glu Gln Arg Ile Ser Leu Pro Glu Ser Leu<br>          275                          280                    285 | | 924 |
| aag cgc att ccg att gag gat ggc tcg ggg gag gtt gtg ctg agc cgg<br>Lys Arg Ile Pro Ile Glu Asp Gly Ser Gly Glu Val Val Leu Ser Arg<br>290                            295                    300 | | 972 |
| aag gta ctg ctg gac ggg gtg cag aac ctc cga gca gaa gac ctg gtg<br>Lys Val Leu Leu Asp Gly Val Gln Asn Leu Arg Ala Glu Asp Leu Val<br>305                        310                    315                    320 | | 1020 |
| ggg aag tct ttg tac gtg tct gcc acc gtc atc ttg cac tca ggc agt<br>Gly Lys Ser Leu Tyr Val Ser Ala Thr Val Ile Leu His Ser Gly Ser<br>                      325                    330                    335 | | 1068 |
| gac atg gtg cag gca gag cgc agc ggg atc ccc atc gtg acc tct ccc<br>Asp Met Val Gln Ala Glu Arg Ser Gly Ile Pro Ile Val Thr Ser Pro<br>340                            345                    350 | | 1116 |
| tac cag atc cac ttc acc aag aca ccc aag tac ttc aaa cca gga atg<br>Tyr Gln Ile His Phe Thr Lys Thr Pro Lys Tyr Phe Lys Pro Gly Met<br>355                            360                    365 | | 1164 |
| ccc ttt gac ctc atg gtg ttc gtg acg aac cct gat ggc tct cca gcc<br>Pro Phe Asp Leu Met Val Phe Val Thr Asn Pro Asp Gly Ser Pro Ala<br>370                            375                    380 | | 1212 |
| tac cga gtc ccc gtg gca gtc cag ggc gag gac act gtg cag tct cta<br>Tyr Arg Val Pro Val Ala Val Gln Gly Glu Asp Thr Val Gln Ser Leu<br>385                        390                    395                    400 | | 1260 |
| acc cag gga gat ggc gtg gcc aaa ctc agc atc aac aca cac ccc agc<br>Thr Gln Gly Asp Gly Val Ala Lys Leu Ser Ile Asn Thr His Pro Ser<br>                      405                    410                    415 | | 1308 |
| cag aag ccc ttg agc atc acg gtg cgc acg aag aag cag gag ctc tcg<br>Gln Lys Pro Leu Ser Ile Thr Val Arg Thr Lys Lys Gln Glu Leu Ser<br>420                            425                    430 | | 1356 |
| gag gca gag cag gct acc agg acc atg cag gct ctg ccc tac agc acc<br>Glu Ala Glu Gln Ala Thr Arg Thr Met Gln Ala Leu Pro Tyr Ser Thr<br>                      435                    440                    445 | | 1404 |
| gtg ggc aac tcc aac aat tac ctg cat ctc tca gtg cta cgt aca gag<br>Val Gly Asn Ser Asn Asn Tyr Leu His Leu Ser Val Leu Arg Thr Glu<br>450                            455                    460 | | 1452 |
| ctc aga ccc ggg gag acc ctc aac gtc aac ttc ctc ctg cga atg gac<br>Leu Arg Pro Gly Glu Thr Leu Asn Val Asn Phe Leu Leu Arg Met Asp<br>465                        470                    475                    480 | | 1500 |
| cgc gcc cac gag gcc aag atc cgc tac tac acc tac ctg atc atg aac<br>Arg Ala His Glu Ala Lys Ile Arg Tyr Tyr Thr Tyr Leu Ile Met Asn<br>                      485                    490                    495 | | 1548 |
| aag ggc agg ctg ttg aag gcg gga cgc cag gtg cga gag ccc ggc cag<br>Lys Gly Arg Leu Leu Lys Ala Gly Arg Gln Val Arg Glu Pro Gly Gln<br>                      500                    505                    510 | | 1596 |
| gac ctg gtg gtg ctg ccc ctg tcc atc acc acc gac ttc atc cct tcc<br>Asp Leu Val Val Leu Pro Leu Ser Ile Thr Thr Asp Phe Ile Pro Ser<br>                  515                    520                    525 | | 1644 |
| ttc cgc ctg gtg gcg tac tac acg ctg atc ggt gcc agc ggc cag agg<br>Phe Arg Leu Val Ala Tyr Tyr Thr Leu Ile Gly Ala Ser Gly Gln Arg<br>530                            535                    540 | | 1692 |
| gag gtg gtg gcc gac tcc gtg tgg gtg gac gtc aag gac tcc tgc gtg<br>Glu Val Val Ala Asp Ser Val Trp Val Asp Val Lys Asp Ser Cys Val<br>545                            550                    555                    560 | | 1740 |
| ggc tcg ctg gtg gta aaa agc ggc cag tca gaa gac cgg cag cct gta<br>Gly Ser Leu Val Val Lys Ser Gly Gln Ser Glu Asp Arg Gln Pro Val<br>                      565                    570                    575 | | 1788 |

-continued

| | | |
|---|---|---|
| cct ggg cag cag atg acc ctg aag ata gag ggt gac cac ggg gcc cgg<br>Pro Gly Gln Gln Met Thr Leu Lys Ile Glu Gly Asp His Gly Ala Arg<br>               580                        585                     590 | 1836 |
| gtg gta ctg gtg gcc gtg gac aag ggc gtg ttc gtg ctg aat aag aag<br>Val Val Leu Val Ala Val Asp Lys Gly Val Phe Val Leu Asn Lys Lys<br>595                       600                     605 | 1884 |
| aac aaa ctg acg cag agt aag atc tgg gac gtg gtg gag aag gca gac<br>Asn Lys Leu Thr Gln Ser Lys Ile Trp Asp Val Val Glu Lys Ala Asp<br>               610                     615                   620 | 1932 |
| atc ggc tgc acc ccg ggc agt ggg aag gat tac gcc ggt gtc ttc tcc<br>Ile Gly Cys Thr Pro Gly Ser Gly Lys Asp Tyr Ala Gly Val Phe Ser<br>625                       630                     635                   640 | 1980 |
| gac gca ggg ctg acc ttc acg agc agc agt ggc cag cag acc gcc cag<br>Asp Ala Gly Leu Thr Phe Thr Ser Ser Ser Gly Gln Gln Thr Ala Gln<br>               645                     650                   655 | 2028 |
| agg gca gaa ctt cag tgc ccg cag cca gcc gcc cgc cga cgc cgt tcc<br>Arg Ala Glu Leu Gln Cys Pro Gln Pro Ala Ala Arg Arg Arg Arg Ser<br>                 660                     665                   670 | 2076 |
| gtg cag ctc acg gag aag cga atg gac aaa gtc ggc aag tac ccc aag<br>Val Gln Leu Thr Glu Lys Arg Met Asp Lys Val Gly Lys Tyr Pro Lys<br>             675                     680                     685 | 2124 |
| gag ctg cgc aag tgc tgc gag gac ggc atg cgg gag aac ccc atg agg<br>Glu Leu Arg Lys Cys Cys Glu Asp Gly Met Arg Glu Asn Pro Met Arg<br>             690                     695                   700 | 2172 |
| ttc tcg tgc cag cgc cgg acc cgt ttc atc tcc ctg ggc gag gcg tgc<br>Phe Ser Cys Gln Arg Arg Thr Arg Phe Ile Ser Leu Gly Glu Ala Cys<br>705                     710                     715                   720 | 2220 |
| aag aag gtc ttc ctg gac tgc tgc aac tac atc aca gag ctg cgg cgg<br>Lys Lys Val Phe Leu Asp Cys Cys Asn Tyr Ile Thr Glu Leu Arg Arg<br>                   725                     730                   735 | 2268 |
| cag cac gcg cgg gcc agc cac ctg ggc ctg gcc agg agt aac ctg gat<br>Gln His Ala Arg Ala Ser His Leu Gly Leu Ala Arg Ser Asn Leu Asp<br>               740                     745                   750 | 2316 |
| gag gac atc att gca gaa gag aac atc gtt tcc cga agt gag ttc cca<br>Glu Asp Ile Ile Ala Glu Glu Asn Ile Val Ser Arg Ser Glu Phe Pro<br>             755                     760                   765 | 2364 |
| gag agc tgg ctg tgg aac gtt gag gac ttg aaa gag cca ccg aaa aat<br>Glu Ser Trp Leu Trp Asn Val Glu Asp Leu Lys Glu Pro Pro Lys Asn<br>770                     775                     780 | 2412 |
| gga atc tct acg aag ctc atg aat ata ttt ttg aaa gac tcc atc acc<br>Gly Ile Ser Thr Lys Leu Met Asn Ile Phe Leu Lys Asp Ser Ile Thr<br>785                     790                     795                   800 | 2460 |
| acg tgg gag att ctg gct gtc agc atg tcg gac aag aaa ggg atc tgt<br>Thr Trp Glu Ile Leu Ala Val Ser Met Ser Asp Lys Lys Gly Ile Cys<br>               805                     810                   815 | 2508 |
| gtg gca gac ccc ttc gag gtc aca gta atg cag gac ttc ttc atc gac<br>Val Ala Asp Pro Phe Glu Val Thr Val Met Gln Asp Phe Phe Ile Asp<br>               820                     825                   830 | 2556 |
| ctg cgg cta ccc tac tct gtt gtt cga aac gag cag gtg gaa atc cga<br>Leu Arg Leu Pro Tyr Ser Val Val Arg Asn Glu Gln Val Glu Ile Arg<br>             835                     840                   845 | 2604 |
| gcc gtt ctc tac aat tac cgg cag aac caa gag ctc aag gtg agg gtg<br>Ala Val Leu Tyr Asn Tyr Arg Gln Asn Gln Glu Leu Lys Val Arg Val<br>850                     855                     860 | 2652 |
| gaa cta ctc cac aat cca gcc ttc tgc agc ctg gcc acc acc aag agg<br>Glu Leu Leu His Asn Pro Ala Phe Cys Ser Leu Ala Thr Thr Lys Arg<br>865                     870                     875                   880 | 2700 |
| cgt cac cag cag acc gta acc atc ccc ccc aag tcc tcg ttg tcc gtt<br>Arg His Gln Gln Thr Val Thr Ile Pro Pro Lys Ser Ser Leu Ser Val<br>               885                     890                   895 | 2748 |

| | | |
|---|---|---|
| cca tat gtc atc gtg ccg cta aag acc ggc ctg cag gaa gtg gaa gtc<br>Pro Tyr Val Ile Val Pro Leu Lys Thr Gly Leu Gln Glu Val Glu Val<br>              900                    905                  910 | 2796 |

```
cca tat gtc atc gtg ccg cta aag acc ggc ctg cag gaa gtg gaa gtc      2796
Pro Tyr Val Ile Val Pro Leu Lys Thr Gly Leu Gln Glu Val Glu Val
            900                 905                 910 aag gct gcc gtc tac cat cat ttc atc agt gac ggt gtc agg aag tcc      2844
Lys Ala Ala Val Tyr His His Phe Ile Ser Asp Gly Val Arg Lys Ser
            915                 920                 925 ctg aag gtc gtg ccg gaa gga atc aga atg aac aaa act gtg gct gtt      2892
Leu Lys Val Val Pro Glu Gly Ile Arg Met Asn Lys Thr Val Ala Val
        930                 935                 940 cgc acc ctg gat cca gaa cgc ctg ggc cgt gaa gga gtg cag aaa gag      2940
Arg Thr Leu Asp Pro Glu Arg Leu Gly Arg Glu Gly Val Gln Lys Glu
945                 950                 955                 960 gac atc cca cct gca gac ctc agt gac caa gtc ccg gac acc gag tct      2988
Asp Ile Pro Pro Ala Asp Leu Ser Asp Gln Val Pro Asp Thr Glu Ser
                965                 970                 975 gag acc aga att ctc ctg caa ggg acc cca gtg gcc cag atg aca gag      3036
Glu Thr Arg Ile Leu Leu Gln Gly Thr Pro Val Ala Gln Met Thr Glu
            980                 985                 990 gat gcc gtc gac gcg gaa cgg ctg aag cac ctc att gtg acc ccc tcg      3084
Asp Ala Val Asp Ala Glu Arg Leu Lys His Leu Ile Val Thr Pro Ser
        995                 1000                1005 ggc tgc ggg gaa cag aac atg atc ggc atg acg ccc acg gtc atc gct      3132
Gly Cys Gly Glu Gln Asn Met Ile Gly Met Thr Pro Thr Val Ile Ala
    1010                1015                1020 gtg cat tac ctg gat gaa acg gag cag tgg gag aag ttc ggc cta gag      3180
Val His Tyr Leu Asp Glu Thr Glu Gln Trp Glu Lys Phe Gly Leu Glu
1025                1030                1035                1040 aag cgg cag ggg gcc ttg gag ctc atc aag aag ggg tac acc cag cag      3228
Lys Arg Gln Gly Ala Leu Glu Leu Ile Lys Lys Gly Tyr Thr Gln Gln
                1045                1050                1055 ctg gcc ttc aga caa ccc agc tct gcc ttt gcg gcc ttc gtg aaa cgg      3276
Leu Ala Phe Arg Gln Pro Ser Ser Ala Phe Ala Ala Phe Val Lys Arg
            1060                1065                1070 gca ccc agc acc tgg ctg acc gcc tac gtg gtc aag gtc ttc tct ctg      3324
Ala Pro Ser Thr Trp Leu Thr Ala Tyr Val Val Lys Val Phe Ser Leu
        1075                1080                1085 gct gtc aac ctc atc gcc atc gac tcc caa gtc ctc tgc ggg gct gtt      3372
Ala Val Asn Leu Ile Ala Ile Asp Ser Gln Val Leu Cys Gly Ala Val
    1090                1095                1100 aaa tgg ctg atc ctg gag aag cag aag ccc gac ggg gtc ttc cag gag      3420
Lys Trp Leu Ile Leu Glu Lys Gln Lys Pro Asp Gly Val Phe Gln Glu
1105                1110                1115                1120 gat gcg ccc gtg ata cac caa gaa atg att ggt gga tta cgg aac aac      3468
Asp Ala Pro Val Ile His Gln Glu Met Ile Gly Gly Leu Arg Asn Asn
                1125                1130                1135 aac gag aaa gac atg gcc ctc acg gcc ttt gtt ctc atc tcg ctg cag      3516
Asn Glu Lys Asp Met Ala Leu Thr Ala Phe Val Leu Ile Ser Leu Gln
            1140                1145                1150 gag gct aaa gat att tgc gag gag cag gtc aac agc ctg cca ggc agc      3564
Glu Ala Lys Asp Ile Cys Glu Glu Gln Val Asn Ser Leu Pro Gly Ser
        1155                1160                1165 atc act aaa gca gga gac ttc ctt gaa gcc aac tac atg aac cta cag      3612
Ile Thr Lys Ala Gly Asp Phe Leu Glu Ala Asn Tyr Met Asn Leu Gln
    1170                1175                1180 aga tcc tac act gtg gcc att gct ggc tat gct ctg gcc cag atg ggc      3660
Arg Ser Tyr Thr Val Ala Ile Ala Gly Tyr Ala Leu Ala Gln Met Gly
1185                1190                1195                1200 agg ctg aag ggg cct ctt ctt aac aaa ttt ctg acc aca gcc aaa gat      3708
Arg Leu Lys Gly Pro Leu Leu Asn Lys Phe Leu Thr Thr Ala Lys Asp
                1205                1210                1215
```

```
aag aac cgc tgg gag gac cct ggt aag cag ctc tac aac gtg gag gcc    3756
Lys Asn Arg Trp Glu Asp Pro Gly Lys Gln Leu Tyr Asn Val Glu Ala
        1220                1225                1230 aca tcc tat gcc ctc ttg gcc cta ctg cag cta aaa gac ttt gac ttt    3804
Thr Ser Tyr Ala Leu Leu Ala Leu Leu Gln Leu Lys Asp Phe Asp Phe
    1235                1240                1245 gtg cct ccc gtc gtg cgt tgg ctc aat gaa cag aga tac tac ggt ggt    3852
Val Pro Pro Val Val Arg Trp Leu Asn Glu Gln Arg Tyr Tyr Gly Gly
1250                1255                1260 ggc tat ggc tct acc cag gcc acc ttc atg gtg ttc caa gcc ttg gct    3900
Gly Tyr Gly Ser Thr Gln Ala Thr Phe Met Val Phe Gln Ala Leu Ala
1265                1270                1275                1280 caa tac caa aag gac gcc cct gac cac cag gaa ctg aac ctt gat gtg    3948
Gln Tyr Gln Lys Asp Ala Pro Asp His Gln Glu Leu Asn Leu Asp Val
        1285                1290                1295 tcc ctc caa ctg ccc agc cgc agc tcc aag atc acc cac cgt atc cac    3996
Ser Leu Gln Leu Pro Ser Arg Ser Ser Lys Ile Thr His Arg Ile His
    1300                1305                1310 tgg gaa tct gcc agc ctc ctg cga tca gaa gag acc aag gaa aat gag    4044
Trp Glu Ser Ala Ser Leu Leu Arg Ser Glu Glu Thr Lys Glu Asn Glu
        1315                1320                1325 ggt ttc aca gtc aca gct gaa gga aaa ggc caa ggc acc ttg tcg gtg    4092
Gly Phe Thr Val Thr Ala Glu Gly Lys Gly Gln Gly Thr Leu Ser Val
        1330                1335                1340 gtg aca atg tac cat gct aag gcc aaa gat caa ctc acc tgt aat aaa    4140
Val Thr Met Tyr His Ala Lys Ala Lys Asp Gln Leu Thr Cys Asn Lys
1345                1350                1355                1360 ttc gac ctc aag gtc acc ata aaa cca gca ccg gaa aca gaa aag agg    4188
Phe Asp Leu Lys Val Thr Ile Lys Pro Ala Pro Glu Thr Glu Lys Arg
        1365                1370                1375 cct cag gat gcc aag aac act atg atc ctt gag atc tgt acc agg tac    4236
Pro Gln Asp Ala Lys Asn Thr Met Ile Leu Glu Ile Cys Thr Arg Tyr
        1380                1385                1390 cgg gga gac cag gat gcc act atg tct ata ttg gac ata tcc atg atg    4284
Arg Gly Asp Gln Asp Ala Thr Met Ser Ile Leu Asp Ile Ser Met Met
        1395                1400                1405 act ggc ttt gct cca gac aca gat gac ctg aag cag ctg gcc aat ggt    4332
Thr Gly Phe Ala Pro Asp Thr Asp Asp Leu Lys Gln Leu Ala Asn Gly
    1410                1415                1420 gtt gac aga tac atc tcc aag tat gag ctg gac aaa gcc ttc tcc gat    4380
Val Asp Arg Tyr Ile Ser Lys Tyr Glu Leu Asp Lys Ala Phe Ser Asp
1425                1430                1435                1440 agg aac acc ctc atc atc tac ctg gac aag gtc tca cac tct gag gat    4428
Arg Asn Thr Leu Ile Ile Tyr Leu Asp Lys Val Ser His Ser Glu Asp
        1445                1450                1455 gac tgt cta gct ttc aaa gtt cac caa tac ttt aat gta gag ctt atc    4476
Asp Cys Leu Ala Phe Lys Val His Gln Tyr Phe Asn Val Glu Leu Ile
        1460                1465                1470 cag cct gga gca gtc aag gtc tac gcc tat tac aac ctg gag gaa agc    4524
Gln Pro Gly Ala Val Lys Val Tyr Ala Tyr Tyr Asn Leu Glu Glu Ser
        1475                1480                1485 tgt acc cgg ttc tac cat ccg gaa aag gag gat gga aag ctg aac aag    4572
Cys Thr Arg Phe Tyr His Pro Glu Lys Glu Asp Gly Lys Leu Asn Lys
    1490                1495                1500 ctc tgc cgt gat gaa ctg tgc cgc tgt gct gag gag aat tgc ttc ata    4620
Leu Cys Arg Asp Glu Leu Cys Arg Cys Ala Glu Glu Asn Cys Phe Ile
1505                1510                1515                1520 caa aag tcg gat gac aag gtc acc ctg gaa gaa cgg ctg gac aag gcc    4668
Gln Lys Ser Asp Asp Lys Val Thr Leu Glu Glu Arg Leu Asp Lys Ala
        1525                1530                1535
```

```
tgt gag cca gga gtg gac tat gtg tac aag acc cga ctg gtc aag gtt      4716
Cys Glu Pro Gly Val Asp Tyr Val Tyr Lys Thr Arg Leu Val Lys Val
        1540                1545                1550 cag ctg tcc aat gac ttt gac gag tac atc atg gcc att gag cag acc      4764
Gln Leu Ser Asn Asp Phe Asp Glu Tyr Ile Met Ala Ile Glu Gln Thr
    1555                1560                1565 atc aag tca ggc tcg gat gag gtg cag gtt gga cag cag cgc acg ttc      4812
Ile Lys Ser Gly Ser Asp Glu Val Gln Val Gly Gln Gln Arg Thr Phe
1570                1575                1580 atc agc ccc atc aag tgc aga gaa gcc ctg aag ctg gag gag aag aaa      4860
Ile Ser Pro Ile Lys Cys Arg Glu Ala Leu Lys Leu Glu Glu Lys Lys
1585                1590                1595                1600 cac tac ctc atg tgg ggt ctc tcc tcc gat ttc tgg gga gag aag ccc      4908
His Tyr Leu Met Trp Gly Leu Ser Ser Asp Phe Trp Gly Glu Lys Pro
                1605                1610                1615 aac ctc agc tac atc atc ggg aag gac act tgg gtg gag cac tgg cct      4956
Asn Leu Ser Tyr Ile Ile Gly Lys Asp Thr Trp Val Glu His Trp Pro
            1620                1625                1630 gag gag gac gaa tgc caa gac gaa gag aac cag aaa caa tgc cag gac      5004
Glu Glu Asp Glu Cys Gln Asp Glu Glu Asn Gln Lys Gln Cys Gln Asp
        1635                1640                1645 ctc ggc gcc ttc acc gag agc atg gtt gtc ttt ggg tgc ccc aac tga      5052
Leu Gly Ala Phe Thr Glu Ser Met Val Val Phe Gly Cys Pro Asn *
    1650                1655                1660 ccacaccccc attcc                                                      5067

<210> SEQ ID NO 2
<211> LENGTH: 1663
<212> TYPE: PRT
<213> ORGANISM: Homo sapiens

<400> SEQUENCE: 2

Met Gly Pro Thr Ser Gly Pro Ser Leu Leu Leu Leu Leu Thr His
  1               5                  10                  15

Leu Pro Leu Ala Leu Gly Ser Pro Met Tyr Ser Ile Ile Thr Pro Asn
                 20                  25                  30

Ile Leu Arg Leu Glu Ser Glu Glu Thr Met Val Leu Glu Ala His Asp
              35                  40                  45

Ala Gln Gly Asp Val Pro Val Thr Val Thr Val His Asp Phe Pro Gly
         50                  55                  60

Lys Lys Leu Val Leu Ser Ser Glu Lys Thr Val Leu Thr Pro Ala Thr
 65                  70                  75                  80

Asn His Met Gly Asn Val Thr Phe Thr Ile Pro Ala Asn Arg Glu Phe
                 85                  90                  95

Lys Ser Glu Lys Gly Arg Asn Lys Phe Val Thr Val Gln Ala Thr Phe
            100                 105                 110

Gly Thr Gln Val Val Glu Lys Val Val Leu Val Ser Leu Gln Ser Gly
        115                 120                 125

Tyr Leu Phe Ile Gln Thr Asp Lys Thr Ile Tyr Thr Pro Gly Ser Thr
    130                 135                 140

Val Leu Tyr Arg Ile Phe Thr Val Asn His Lys Leu Leu Pro Val Gly
145                 150                 155                 160

Arg Thr Val Met Val Asn Ile Glu Asn Pro Glu Gly Ile Pro Val Lys
                165                 170                 175

Gln Asp Ser Leu Ser Ser Gln Asn Gln Leu Gly Val Leu Pro Leu Ser
            180                 185                 190

Trp Asp Ile Pro Glu Leu Val Asn Met Gly Gln Trp Lys Ile Arg Ala
```

-continued

```
                195                 200                 205
Tyr Tyr Glu Asn Ser Pro Gln Gln Val Phe Ser Thr Glu Phe Glu Val
210                 215                 220
Lys Glu Tyr Val Leu Pro Ser Phe Glu Val Ile Val Glu Pro Thr Glu
225                 230                 235                 240
Lys Phe Tyr Tyr Ile Tyr Asn Glu Lys Gly Leu Glu Val Thr Ile Thr
                245                 250                 255
Ala Arg Phe Leu Tyr Gly Lys Lys Val Glu Gly Thr Ala Phe Val Ile
            260                 265                 270
Phe Gly Ile Gln Asp Gly Glu Gln Arg Ile Ser Leu Pro Glu Ser Leu
        275                 280                 285
Lys Arg Ile Pro Ile Glu Asp Gly Ser Gly Glu Val Val Leu Ser Arg
290                 295                 300
Lys Val Leu Leu Asp Gly Val Gln Asn Leu Arg Ala Glu Asp Leu Val
305                 310                 315                 320
Gly Lys Ser Leu Tyr Val Ser Ala Thr Val Ile Leu His Ser Gly Ser
                325                 330                 335
Asp Met Val Gln Ala Glu Arg Ser Gly Ile Pro Ile Val Thr Ser Pro
            340                 345                 350
Tyr Gln Ile His Phe Thr Lys Thr Pro Lys Tyr Phe Lys Pro Gly Met
        355                 360                 365
Pro Phe Asp Leu Met Val Phe Val Thr Asn Pro Asp Gly Ser Pro Ala
370                 375                 380
Tyr Arg Val Pro Val Ala Val Gln Gly Glu Asp Thr Val Gln Ser Leu
385                 390                 395                 400
Thr Gln Gly Asp Gly Val Ala Lys Leu Ser Ile Asn Thr His Pro Ser
                405                 410                 415
Gln Lys Pro Leu Ser Ile Thr Val Arg Thr Lys Lys Gln Glu Leu Ser
            420                 425                 430
Glu Ala Glu Gln Ala Thr Arg Thr Met Gln Ala Leu Pro Tyr Ser Thr
        435                 440                 445
Val Gly Asn Ser Asn Asn Tyr Leu His Leu Ser Val Leu Arg Thr Glu
450                 455                 460
Leu Arg Pro Gly Glu Thr Leu Asn Val Asn Phe Leu Leu Arg Met Asp
465                 470                 475                 480
Arg Ala His Glu Ala Lys Ile Arg Tyr Tyr Thr Tyr Leu Ile Met Asn
                485                 490                 495
Lys Gly Arg Leu Leu Lys Ala Gly Arg Gln Val Arg Glu Pro Gly Gln
            500                 505                 510
Asp Leu Val Val Leu Pro Leu Ser Ile Thr Thr Asp Phe Ile Pro Ser
        515                 520                 525
Phe Arg Leu Val Ala Tyr Tyr Thr Leu Ile Gly Ala Ser Gly Gln Arg
530                 535                 540
Glu Val Val Ala Asp Ser Val Trp Val Asp Val Lys Asp Ser Cys Val
545                 550                 555                 560
Gly Ser Leu Val Val Lys Ser Gly Gln Ser Glu Asp Arg Gln Pro Val
                565                 570                 575
Pro Gly Gln Gln Met Thr Leu Lys Ile Glu Gly Asp His Gly Ala Arg
            580                 585                 590
Val Val Leu Val Ala Val Asp Lys Gly Val Phe Val Leu Asn Lys Lys
        595                 600                 605
Asn Lys Leu Thr Gln Ser Lys Ile Trp Asp Val Val Glu Lys Ala Asp
610                 615                 620
```

-continued

```
Ile Gly Cys Thr Pro Gly Ser Gly Lys Asp Tyr Ala Gly Val Phe Ser
625                 630                 635                 640

Asp Ala Gly Leu Thr Phe Thr Ser Ser Gly Gln Gln Thr Ala Gln
            645                 650                 655

Arg Ala Glu Leu Gln Cys Pro Gln Pro Ala Arg Arg Arg Ser
        660                 665                 670

Val Gln Leu Thr Glu Lys Arg Met Asp Lys Val Gly Lys Tyr Pro Lys
    675                 680                 685

Glu Leu Arg Lys Cys Cys Glu Asp Gly Met Arg Glu Asn Pro Met Arg
690                 695                 700

Phe Ser Cys Gln Arg Arg Thr Arg Phe Ile Ser Leu Gly Glu Ala Cys
705                 710                 715                 720

Lys Lys Val Phe Leu Asp Cys Cys Asn Tyr Ile Thr Glu Leu Arg Arg
                725                 730                 735

Gln His Ala Arg Ala Ser His Leu Gly Leu Ala Arg Ser Asn Leu Asp
            740                 745                 750

Glu Asp Ile Ile Ala Glu Glu Asn Ile Val Ser Arg Ser Glu Phe Pro
        755                 760                 765

Glu Ser Trp Leu Trp Asn Val Glu Asp Leu Lys Glu Pro Pro Lys Asn
770                 775                 780

Gly Ile Ser Thr Lys Leu Met Asn Ile Phe Leu Lys Asp Ser Ile Thr
785                 790                 795                 800

Thr Trp Glu Ile Leu Ala Val Ser Met Ser Asp Lys Lys Gly Ile Cys
                805                 810                 815

Val Ala Asp Pro Phe Glu Val Thr Val Met Gln Asp Phe Phe Ile Asp
            820                 825                 830

Leu Arg Leu Pro Tyr Ser Val Val Arg Asn Glu Gln Val Glu Ile Arg
        835                 840                 845

Ala Val Leu Tyr Asn Tyr Arg Gln Asn Gln Glu Leu Lys Val Arg Val
    850                 855                 860

Glu Leu Leu His Asn Pro Ala Phe Cys Ser Leu Ala Thr Thr Lys Arg
865                 870                 875                 880

Arg His Gln Gln Thr Val Thr Ile Pro Pro Lys Ser Ser Leu Ser Val
                885                 890                 895

Pro Tyr Val Ile Val Pro Leu Lys Thr Gly Leu Gln Glu Val Glu Val
            900                 905                 910

Lys Ala Ala Val Tyr His His Phe Ile Ser Asp Gly Val Arg Lys Ser
        915                 920                 925

Leu Lys Val Val Pro Glu Gly Ile Arg Met Asn Lys Thr Val Ala Val
    930                 935                 940

Arg Thr Leu Asp Pro Glu Arg Leu Gly Arg Glu Gly Val Gln Lys Glu
945                 950                 955                 960

Asp Ile Pro Pro Ala Asp Leu Ser Asp Gln Val Pro Asp Thr Glu Ser
                965                 970                 975

Glu Thr Arg Ile Leu Leu Gln Gly Thr Pro Val Ala Gln Met Thr Glu
            980                 985                 990

Asp Ala Val Asp Ala Glu Arg Leu Lys His Leu Ile Val Thr Pro Ser
        995                 1000                1005

Gly Cys Gly Glu Gln Asn Met Ile Gly Met Thr Pro Thr Val Ile Ala
    1010                1015                1020

Val His Tyr Leu Asp Glu Thr Glu Gln Trp Glu Lys Phe Gly Leu Glu
1025                1030                1035                1040

Lys Arg Gln Gly Ala Leu Glu Leu Ile Lys Lys Gly Tyr Thr Gln Gln
                1045                1050                1055
```

```
Leu Ala Phe Arg Gln Pro Ser Ser Ala Phe Ala Ala Phe Val Lys Arg
            1060                1065                1070

Ala Pro Ser Thr Trp Leu Thr Ala Tyr Val Val Lys Val Phe Ser Leu
            1075                1080                1085

Ala Val Asn Leu Ile Ala Ile Asp Ser Gln Val Leu Cys Gly Ala Val
            1090                1095                1100

Lys Trp Leu Ile Leu Glu Lys Gln Lys Pro Asp Gly Val Phe Gln Glu
1105                1110                1115                1120

Asp Ala Pro Val Ile His Gln Glu Met Ile Gly Gly Leu Arg Asn Asn
            1125                1130                1135

Asn Glu Lys Asp Met Ala Leu Thr Ala Phe Val Leu Ile Ser Leu Gln
            1140                1145                1150

Glu Ala Lys Asp Ile Cys Glu Glu Gln Val Asn Ser Leu Pro Gly Ser
            1155                1160                1165

Ile Thr Lys Ala Gly Asp Phe Leu Glu Ala Asn Tyr Met Asn Leu Gln
            1170                1175                1180

Arg Ser Tyr Thr Val Ala Ile Ala Gly Tyr Ala Leu Ala Gln Met Gly
1185                1190                1195                1200

Arg Leu Lys Gly Pro Leu Leu Asn Lys Phe Leu Thr Thr Ala Lys Asp
            1205                1210                1215

Lys Asn Arg Trp Glu Asp Pro Gly Lys Gln Leu Tyr Asn Val Glu Ala
            1220                1225                1230

Thr Ser Tyr Ala Leu Leu Ala Leu Leu Gln Leu Lys Asp Phe Asp Phe
            1235                1240                1245

Val Pro Pro Val Val Arg Trp Leu Asn Glu Gln Arg Tyr Tyr Gly Gly
            1250                1255                1260

Gly Tyr Gly Ser Thr Gln Ala Thr Phe Met Val Phe Gln Ala Leu Ala
1265                1270                1275                1280

Gln Tyr Gln Lys Asp Ala Pro Asp His Gln Glu Leu Asn Leu Asp Val
            1285                1290                1295

Ser Leu Gln Leu Pro Ser Arg Ser Ser Lys Ile Thr His Arg Ile His
            1300                1305                1310

Trp Glu Ser Ala Ser Leu Leu Arg Ser Glu Glu Thr Lys Glu Asn Glu
            1315                1320                1325

Gly Phe Thr Val Thr Ala Glu Gly Lys Gly Gln Gly Thr Leu Ser Val
            1330                1335                1340

Val Thr Met Tyr His Ala Lys Ala Lys Asp Gln Leu Thr Cys Asn Lys
1345                1350                1355                1360

Phe Asp Leu Lys Val Thr Ile Lys Pro Ala Pro Glu Thr Glu Lys Arg
            1365                1370                1375

Pro Gln Asp Ala Lys Asn Thr Met Ile Leu Glu Ile Cys Thr Arg Tyr
            1380                1385                1390

Arg Gly Asp Gln Asp Ala Thr Met Ser Ile Leu Asp Ile Ser Met Met
            1395                1400                1405

Thr Gly Phe Ala Pro Asp Thr Asp Asp Leu Lys Gln Leu Ala Asn Gly
            1410                1415                1420

Val Asp Arg Tyr Ile Ser Lys Tyr Glu Leu Asp Lys Ala Phe Ser Asp
1425                1430                1435                1440

Arg Asn Thr Leu Ile Ile Tyr Leu Asp Lys Val Ser His Ser Glu Asp
            1445                1450                1455

Asp Cys Leu Ala Phe Lys Val His Gln Tyr Phe Asn Val Glu Leu Ile
            1460                1465                1470

Gln Pro Gly Ala Val Lys Val Tyr Ala Tyr Tyr Asn Leu Glu Glu Ser
```

-continued

```
                   1475                1480                1485
Cys Thr Arg Phe Tyr His Pro Glu Lys Glu Asp Gly Lys Leu Asn Lys
    1490                1495                1500

Leu Cys Arg Asp Glu Leu Cys Arg Cys Ala Glu Glu Asn Cys Phe Ile
1505                1510                1515                1520

Gln Lys Ser Asp Asp Lys Val Thr Leu Glu Glu Arg Leu Asp Lys Ala
        1525                1530                1535

Cys Glu Pro Gly Val Asp Tyr Val Tyr Lys Thr Arg Leu Val Lys Val
            1540                1545                1550

Gln Leu Ser Asn Asp Phe Asp Glu Tyr Ile Met Ala Ile Glu Gln Thr
        1555                1560                1565

Ile Lys Ser Gly Ser Asp Glu Val Gln Val Gly Gln Gln Arg Thr Phe
    1570                1575                1580

Ile Ser Pro Ile Lys Cys Arg Glu Ala Leu Lys Leu Glu Glu Lys Lys
1585                1590                1595                1600

His Tyr Leu Met Trp Gly Leu Ser Ser Asp Phe Trp Gly Glu Lys Pro
            1605                1610                1615

Asn Leu Ser Tyr Ile Ile Gly Lys Asp Thr Trp Val Glu His Trp Pro
        1620                1625                1630

Glu Glu Asp Glu Cys Gln Asp Glu Glu Asn Gln Lys Gln Cys Gln Asp
            1635                1640                1645

Leu Gly Ala Phe Thr Glu Ser Met Val Val Phe Gly Cys Pro Asn
        1650                1655                1660

<210> SEQ ID NO 3
<211> LENGTH: 5948
<212> TYPE: DNA
<213> ORGANISM: Naja kaouthia
<220> FEATURE:
<221> NAME/KEY: CDS
<222> LOCATION: (4)...(4932)

<400> SEQUENCE: 3 ccc atg gag agg atg gct ctc tat ctg gtg gct gct cta ttg att ggt     48
    Met Glu Arg Met Ala Leu Tyr Leu Val Ala Ala Leu Leu Ile Gly
    1               5                  10                  15 ttt cca ggg tct tct cat ggg gct ctc tac acc ctc atc acc cct gct     96
Phe Pro Gly Ser Ser His Gly Ala Leu Tyr Thr Leu Ile Thr Pro Ala
                20                  25                  30 gtt ttg cga aca gac aca gaa gag caa att ttg gtg gag gcc cat gga    144
Val Leu Arg Thr Asp Thr Glu Glu Gln Ile Leu Val Glu Ala His Gly
            35                  40                  45 gac agt act cca aaa cag ctt gac atc ttt gtt cat gat ttt cca cgg    192
Asp Ser Thr Pro Lys Gln Leu Asp Ile Phe Val His Asp Phe Pro Arg
        50                  55                  60 aag cag aaa acc ttg ttc caa acc aga gta gat atg aat cca gca gga    240
Lys Gln Lys Thr Leu Phe Gln Thr Arg Val Asp Met Asn Pro Ala Gly
65                  70                  75 ggc atg ctt gtc act cca act ata gag att cca gca aaa gaa gtg agt    288
Gly Met Leu Val Thr Pro Thr Ile Glu Ile Pro Ala Lys Glu Val Ser
 80                  85                  90                  95 acg gac tcc agg caa aat caa tat gtg gtt gtg caa gta act ggt cct    336
Thr Asp Ser Arg Gln Asn Gln Tyr Val Val Val Gln Val Thr Gly Pro
                100                 105                 110 caa gtg aga ttg gaa aag gtg gtt ctc ctt tct tac cag agt agc ttt    384
Gln Val Arg Leu Glu Lys Val Val Leu Leu Ser Tyr Gln Ser Ser Phe
            115                 120                 125 ctg ttt atc cag aca gat aaa ggc atc tat aca cca ggg tct cca gta    432
Leu Phe Ile Gln Thr Asp Lys Gly Ile Tyr Thr Pro Gly Ser Pro Val
```

```
              130                 135                 140
ctc tat cgt gtt ttt tct atg gat cac aac aca agc aag atg aac aaa       480
Leu Tyr Arg Val Phe Ser Met Asp His Asn Thr Ser Lys Met Asn Lys
    145                 150                 155 act gtg att gtt gag ttt cag act cca gaa ggc att ctt gtc agt tct       528
Thr Val Ile Val Glu Phe Gln Thr Pro Glu Gly Ile Leu Val Ser Ser
160                 165                 170                 175 aat tca gtt gac cta aac ttc ttc tgg cct tac aat tta cca gac ctt       576
Asn Ser Val Asp Leu Asn Phe Phe Trp Pro Tyr Asn Leu Pro Asp Leu
                180                 185                 190 gtc agt ttg ggg act tgg agg att gtg gcc aaa tat gaa cat tcc cca       624
Val Ser Leu Gly Thr Trp Arg Ile Val Ala Lys Tyr Glu His Ser Pro
            195                 200                 205 gag aat tat act gca tat ttt gat gtc agg aaa tat gtg tta cca agc       672
Glu Asn Tyr Thr Ala Tyr Phe Asp Val Arg Lys Tyr Val Leu Pro Ser
        210                 215                 220 ttt gaa gtc cgt ctg caa cca tca gag aag ttt ttt tac att gac ggc       720
Phe Glu Val Arg Leu Gln Pro Ser Glu Lys Phe Phe Tyr Ile Asp Gly
    225                 230                 235 aat gaa aat ttc cac gtg tct atc act gca agg tac ttg tat gga gag       768
Asn Glu Asn Phe His Val Ser Ile Thr Ala Arg Tyr Leu Tyr Gly Glu
240                 245                 250                 255 gaa gtg gaa ggt gtg gcc ttt gtc ctc ttt gga gtg aaa ata gat gat       816
Glu Val Glu Gly Val Ala Phe Val Leu Phe Gly Val Lys Ile Asp Asp
                260                 265                 270 gct aaa aag agt att cca gac tca ctc acg aga att ccg att att gat       864
Ala Lys Lys Ser Ile Pro Asp Ser Leu Thr Arg Ile Pro Ile Ile Asp
            275                 280                 285 gga gat ggg aaa gca aca cta aaa aga gat aca ttc cgt tct cga ttt       912
Gly Asp Gly Lys Ala Thr Leu Lys Arg Asp Thr Phe Arg Ser Arg Phe
        290                 295                 300 cca aat ctc aat gag ctt gtt ggg cat act ctg tat gca tct gta aca       960
Pro Asn Leu Asn Glu Leu Val Gly His Thr Leu Tyr Ala Ser Val Thr
    305                 310                 315 gtc atg aca gaa tca ggc agt gat atg gta gtg act gag caa agc ggc      1008
Val Met Thr Glu Ser Gly Ser Asp Met Val Val Thr Glu Gln Ser Gly
320                 325                 330                 335 att cat att gtg gca tct ccc tat cag atc cac ttc aca aaa acc ccc      1056
Ile His Ile Val Ala Ser Pro Tyr Gln Ile His Phe Thr Lys Thr Pro
                340                 345                 350 aaa tat ttc aag cca gga atg cca tat gaa ctg acg gtg tat gtt acc      1104
Lys Tyr Phe Lys Pro Gly Met Pro Tyr Glu Leu Thr Val Tyr Val Thr
            355                 360                 365 aac cct gat ggc tca cca gct gcc cat gtg cca gtg gta tca gag gcc      1152
Asn Pro Asp Gly Ser Pro Ala Ala His Val Pro Val Val Ser Glu Ala
        370                 375                 380 ttt cat tct atg gga acc act ttg agt gat ggg act gct aag ctc atc      1200
Phe His Ser Met Gly Thr Thr Leu Ser Asp Gly Thr Ala Lys Leu Ile
    385                 390                 395 ctg aac ata cca ttg aat gct caa agc cta cca atc act gtt aga act      1248
Leu Asn Ile Pro Leu Asn Ala Gln Ser Leu Pro Ile Thr Val Arg Thr
400                 405                 410                 415 aac cat gga gac ctc cca aga gaa cgc cag gca aca aag tcc atg aca      1296
Asn His Gly Asp Leu Pro Arg Glu Arg Gln Ala Thr Lys Ser Met Thr
                420                 425                 430 gcc ata gcc tac caa acc cag gga gga tct gga aac tat ctt cat gta      1344
Ala Ile Ala Tyr Gln Thr Gln Gly Gly Ser Gly Asn Tyr Leu His Val
            435                 440                 445 gcc att aca tct aca gag att aag ccc gga gat aac tta cct gtc aat      1392
Ala Ile Thr Ser Thr Glu Ile Lys Pro Gly Asp Asn Leu Pro Val Asn
```

```
                450               455               460
ttc aat gtg aag ggc aat gca aat tca ctg aag cag atc aaa tat ttc    1440
Phe Asn Val Lys Gly Asn Ala Asn Ser Leu Lys Gln Ile Lys Tyr Phe
465                 470                 475 aca tac ctc ata ttg aat aaa ggg aag att ttc aag gtt ggc agg caa    1488
Thr Tyr Leu Ile Leu Asn Lys Gly Lys Ile Phe Lys Val Gly Arg Gln
480                 485                 490                 495 ccc agg aga gat ggg cag aat ctg gtg acc atg aat ctg cat atc act    1536
Pro Arg Arg Asp Gly Gln Asn Leu Val Thr Met Asn Leu His Ile Thr
                500                 505                 510 cca gat ctc atc cct tcc ttc cgg ttt gtg gct tac tac caa gtg gga    1584
Pro Asp Leu Ile Pro Ser Phe Arg Phe Val Ala Tyr Tyr Gln Val Gly
            515                 520                 525 aac aac gaa att gtg gct gat tct gtc tgg gtg gat gtg aag gat acc    1632
Asn Asn Glu Ile Val Ala Asp Ser Val Trp Val Asp Val Lys Asp Thr
        530                 535                 540 tgc atg gga acg ttg gtt gtg aaa gga gac aat cta ata caa atg cca    1680
Cys Met Gly Thr Leu Val Val Lys Gly Asp Asn Leu Ile Gln Met Pro
    545                 550                 555 gga gct gca atg aaa atc aaa ttg gaa ggg gat cca ggt gct cgg gtt    1728
Gly Ala Ala Met Lys Ile Lys Leu Glu Gly Asp Pro Gly Ala Arg Val
560                 565                 570                 575 ggt ctt gtg gct gtg gac aaa gca gta tat gtt ctc aat gat aaa tat    1776
Gly Leu Val Ala Val Asp Lys Ala Val Tyr Val Leu Asn Asp Lys Tyr
                580                 585                 590 aag att agc caa gct aag ata tgg gac aca ata gaa aag agt gac ttt    1824
Lys Ile Ser Gln Ala Lys Ile Trp Asp Thr Ile Glu Lys Ser Asp Phe
                595                 600                 605 ggc tgt aca gct ggc agt ggc cag aat aat ctg ggt gtg ttt gaa gat    1872
Gly Cys Thr Ala Gly Ser Gly Gln Asn Asn Leu Gly Val Phe Glu Asp
            610                 615                 620 gct gga ctg gct ctg aca acc agc act aat ctc aac acc aaa cag aga    1920
Ala Gly Leu Ala Leu Thr Thr Ser Thr Asn Leu Asn Thr Lys Gln Arg
625                 630                 635 tca gct gca aag tgt cct cag cct gca aat cgg agg cgt cgc agt tct    1968
Ser Ala Ala Lys Cys Pro Gln Pro Ala Asn Arg Arg Arg Arg Ser Ser
640                 645                 650                 655 gtt ttg ctg ctt gac agc aac gca agc aaa gcg gca gaa ttt cag gat    2016
Val Leu Leu Leu Asp Ser Asn Ala Ser Lys Ala Ala Glu Phe Gln Asp
                660                 665                 670 caa gac ctg cgt aaa tgc tgt gaa gat gtc atg cat gag aac ccc atg    2064
Gln Asp Leu Arg Lys Cys Cys Glu Asp Val Met His Glu Asn Pro Met
            675                 680                 685 ggg tac act tgt gaa aag cgt gca aaa tac atc cag gag gga gat gct    2112
Gly Tyr Thr Cys Glu Lys Arg Ala Lys Tyr Ile Gln Glu Gly Asp Ala
        690                 695                 700 tgt aag gct gcc ttc ctt gaa tgc tgt cgc tac atc aag ggg gtc cga    2160
Cys Lys Ala Ala Phe Leu Glu Cys Cys Arg Tyr Ile Lys Gly Val Arg
705                 710                 715 gat gaa aac caa cgg gag agc gag ttg ttt ctg gca aga gat gat aat    2208
Asp Glu Asn Gln Arg Glu Ser Glu Leu Phe Leu Ala Arg Asp Asp Asn
720                 725                 730                 735 gaa gat ggt ttc ata gca gat agt gat atc atc tca agg tct gat ttc    2256
Glu Asp Gly Phe Ile Ala Asp Ser Asp Ile Ile Ser Arg Ser Asp Phe
                740                 745                 750 ccc aag agt tgg ttg tgg cta aca aag gac ttg acc gag gag cct aac    2304
Pro Lys Ser Trp Leu Trp Leu Thr Lys Asp Leu Thr Glu Glu Pro Asn
            755                 760                 765 agt caa ggg att tca agc aag aca atg tct ttt tat ctg agg gat tcc    2352
Ser Gln Gly Ile Ser Ser Lys Thr Met Ser Phe Tyr Leu Arg Asp Ser
```

-continued

|     | 770 |     |     |     | 775 |     |     |     | 780 |     |     |     |      |
|-----|-----|-----|-----|-----|-----|-----|-----|-----|-----|-----|-----|-----|------|
| atc | aca | acc | tgg | gtg | gtg | ctg | gct | gta | agc | ttt | aca | ccc | acc aaa ggg | 2400 |
| Ile | Thr | Thr | Trp | Val | Val | Leu | Ala | Val | Ser | Phe | Thr | Pro | Thr Lys Gly |
|     | 785 |     |     |     | 790 |     |     |     | 795 |     |     |     |      |

```
atc tgt gtg gct gaa cct tat gaa ata aga gtc atg aaa gtc ttc ttc        2448
Ile Cys Val Ala Glu Pro Tyr Glu Ile Arg Val Met Lys Val Phe Phe
800                 805                 810                 815 att gat ctt caa atg cca tat tca gta gtg aag aat gag cag gtg gag        2496
Ile Asp Leu Gln Met Pro Tyr Ser Val Val Lys Asn Glu Gln Val Glu
                820                 825                 830 att cga gct att ctg cac aac tac gtt aac gag gat att tat gtg cga        2544
Ile Arg Ala Ile Leu His Asn Tyr Val Asn Glu Asp Ile Tyr Val Arg
            835                 840                 845 gtg gaa ctg tta tac aac cca gcc ttc tgc agt gct tcc aca aaa gga        2592
Val Glu Leu Leu Tyr Asn Pro Ala Phe Cys Ser Ala Ser Thr Lys Gly
        850                 855                 860 caa aga tac cga cag cag ttc cca att aaa gcc ctg tcc tcc aga gca        2640
Gln Arg Tyr Arg Gln Gln Phe Pro Ile Lys Ala Leu Ser Ser Arg Ala
    865                 870                 875 gta ccg ttt gtg ata gtc cca tta gag caa gga ttg cat gat gtt gag        2688
Val Pro Phe Val Ile Val Pro Leu Glu Gln Gly Leu His Asp Val Glu
880                 885                 890                 895 att aaa gca agt gtc cag gaa gcg ttg tgg tca gac ggt gtg agg aag        2736
Ile Lys Ala Ser Val Gln Glu Ala Leu Trp Ser Asp Gly Val Arg Lys
                900                 905                 910 aaa ctg aaa gtt gta cct gaa ggg gta cag aaa tcc att gtg act att        2784
Lys Leu Lys Val Val Pro Glu Gly Val Gln Lys Ser Ile Val Thr Ile
            915                 920                 925 gtt aaa ctg gac cca agg gca aaa gga gtt ggt gga aca cag cta gaa        2832
Val Lys Leu Asp Pro Arg Ala Lys Gly Val Gly Gly Thr Gln Leu Glu
        930                 935                 940 gtg atc aaa gcc cgc aaa tta gat gac aga gtg cct gac aca gaa att        2880
Val Ile Lys Ala Arg Lys Leu Asp Asp Arg Val Pro Asp Thr Glu Ile
    945                 950                 955 gaa acc aag att atc atc caa ggt gac cct gtg gct cag att att gaa        2928
Glu Thr Lys Ile Ile Ile Gln Gly Asp Pro Val Ala Gln Ile Ile Glu
960                 965                 970                 975 aac tca att gat gga agt aaa ctc aac cat ctc att atc act cct tct        2976
Asn Ser Ile Asp Gly Ser Lys Leu Asn His Leu Ile Ile Thr Pro Ser
                980                 985                 990 ggc tgt ggg gag caa aat atg atc cgc atg gcc gca cca gtt att gcc        3024
Gly Cys Gly Glu Gln Asn Met Ile Arg Met Ala Ala Pro Val Ile Ala
            995                 1000                1005 acc tac tac ctg gac acc aca gag cag tgg gag act ctc ggc ata aat        3072
Thr Tyr Tyr Leu Asp Thr Thr Glu Gln Trp Glu Thr Leu Gly Ile Asn
        1010                1015                1020 cgc agg act gaa gct gtc aat cag atc gtg act ggt tat gcc cag cag        3120
Arg Arg Thr Glu Ala Val Asn Gln Ile Val Thr Gly Tyr Ala Gln Gln
    1025                1030                1035 atg gtg tac aag aaa gca gat cat tcc tat gca gca ttt aca aac cgt        3168
Met Val Tyr Lys Lys Ala Asp His Ser Tyr Ala Ala Phe Thr Asn Arg
1040                1045                1050                1055 gca tct agt tct tgg cta aca gca tat gtc gta aaa gtc ttt gcc atg        3216
Ala Ser Ser Ser Trp Leu Thr Ala Tyr Val Val Lys Val Phe Ala Met
                1060                1065                1070 gct gcc aaa atg gta gca ggc att agt cat gaa atc att tgt gga ggt        3264
Ala Ala Lys Met Val Ala Gly Ile Ser His Glu Ile Ile Cys Gly Gly
            1075                1080                1085 gtg agg tgg ctg att ctg aac agg caa caa cca gat gga gcg ttc aaa        3312
Val Arg Trp Leu Ile Leu Asn Arg Gln Gln Pro Asp Gly Ala Phe Lys
```

```
                  1090             1095            1100
gaa aat gcc cct gta ctt tct gga aca atg cag gga gga att caa ggt     3360
Glu Asn Ala Pro Val Leu Ser Gly Thr Met Gln Gly Gly Ile Gln Gly
1105                1110                1115 gct gaa gaa gaa gta tat tta aca gct ttc att ctg gtt gcg ttg ttg     3408
Ala Glu Glu Glu Val Tyr Leu Thr Ala Phe Ile Leu Val Ala Leu Leu
1120                1125                1130                1135 gaa tcc aaa aca atc tgc aat gac tat gtc aat agt cta gac agc agc     3456
Glu Ser Lys Thr Ile Cys Asn Asp Tyr Val Asn Ser Leu Asp Ser Ser
                1140                1145                1150 atc aag aag gcc aca aat tat tta ctc aaa aag tat gag aaa ctg caa     3504
Ile Lys Lys Ala Thr Asn Tyr Leu Leu Lys Lys Tyr Glu Lys Leu Gln
            1155                1160                1165 agg cct tac act aca gcc ctc aca gcc tat gct ttg gct gct gca gac     3552
Arg Pro Tyr Thr Thr Ala Leu Thr Ala Tyr Ala Leu Ala Ala Ala Asp
        1170                1175                1180 caa ctc aat gat gac agg gta ctc atg gca gca tca aca gga agg gat     3600
Gln Leu Asn Asp Asp Arg Val Leu Met Ala Ala Ser Thr Gly Arg Asp
1185                1190                1195 cat tgg gaa gaa tac aat gct cac acc cac aac att gaa ggc act tcc     3648
His Trp Glu Glu Tyr Asn Ala His Thr His Asn Ile Glu Gly Thr Ser
1200                1205                1210                1215 tat gcc ttg ttg gcc ctg ctg aaa atg aag aaa ttt gat caa act ggt     3696
Tyr Ala Leu Leu Ala Leu Leu Lys Met Lys Lys Phe Asp Gln Thr Gly
                1220                1225                1230 ccc ata gtc aga tgg ctg aca gat cag aat ttt tat ggg gaa aca tat     3744
Pro Ile Val Arg Trp Leu Thr Asp Gln Asn Phe Tyr Gly Glu Thr Tyr
            1235                1240                1245 gga caa acc caa gca aca gtt atg gca ttt caa gct ctt gct gaa tat     3792
Gly Gln Thr Gln Ala Thr Val Met Ala Phe Gln Ala Leu Ala Glu Tyr
        1250                1255                1260 gag att cag atg cct acc cat aag gac tta aac tta gat att act att     3840
Glu Ile Gln Met Pro Thr His Lys Asp Leu Asn Leu Asp Ile Thr Ile
1265                1270                1275 gaa ctg cca gat cga gaa gta cct ata agg tac aga att aat tat gaa     3888
Glu Leu Pro Asp Arg Glu Val Pro Ile Arg Tyr Arg Ile Asn Tyr Glu
1280                1285                1290                1295 aat gct ctc ctg gct cgg aca gta gag acc aaa ctc aac caa gac atc     3936
Asn Ala Leu Leu Ala Arg Thr Val Glu Thr Lys Leu Asn Gln Asp Ile
                1300                1305                1310 act gtg aca gca tca ggt gat gga aaa gca aca atg acc att ttg aca     3984
Thr Val Thr Ala Ser Gly Asp Gly Lys Ala Thr Met Thr Ile Leu Thr
            1315                1320                1325 ttc tat aac gca cag ttg cag gag aag gca aat gtt tgc aat aaa ttt     4032
Phe Tyr Asn Ala Gln Leu Gln Glu Lys Ala Asn Val Cys Asn Lys Phe
        1330                1335                1340 cat ctt aat gtt tct gtt gaa aac atc cac ttg aat gca atg gga gcc     4080
His Leu Asn Val Ser Val Glu Asn Ile His Leu Asn Ala Met Gly Ala
1345                1350                1355 aag gga gcc ctc atg ctc aag atc tgc aca agg tat ctg gga gaa gtt     4128
Lys Gly Ala Leu Met Leu Lys Ile Cys Thr Arg Tyr Leu Gly Glu Val
1360                1365                1370                1375 gat tct aca atg aca ata att gat att tct atg ctg act ggt ttt ctc     4176
Asp Ser Thr Met Thr Ile Ile Asp Ile Ser Met Leu Thr Gly Phe Leu
                1380                1385                1390 cct gat gct gaa gac ctt aca agg ctt tct aaa gga gtg gac aga tac     4224
Pro Asp Ala Glu Asp Leu Thr Arg Leu Ser Lys Gly Val Asp Arg Tyr
            1395                1400                1405 atc tcc aga tat gaa gtt gac aat aat atg gct cag aaa gta gct gtt     4272
Ile Ser Arg Tyr Glu Val Asp Asn Asn Met Ala Gln Lys Val Ala Val
```

| | |
|---|---|
| atc att tac tta aac aag gtc tcc cac tct gaa gat gaa tgc ctg cac<br>Ile Ile Tyr Leu Asn Lys Val Ser His Ser Glu Asp Glu Cys Leu His<br>1425                   1430                   1435 | 4320 |
| ttt aag att ctc aag cat ttt gaa gtt ggc ttc att cag cca gga tca<br>Phe Lys Ile Leu Lys His Phe Glu Val Gly Phe Ile Gln Pro Gly Ser<br>1440                   1445                   1450                   1455 | 4368 |
| gtc aag gtg tac agc tac tac aat cta gat gaa aaa tgt acc aag ttc<br>Val Lys Val Tyr Ser Tyr Tyr Asn Leu Asp Glu Lys Cys Thr Lys Phe<br>                  1460                   1465                   1470 | 4416 |
| tac cat cca gat aaa gga aca ggc ctt ctc aat aag ata tgt att ggt<br>Tyr His Pro Asp Lys Gly Thr Gly Leu Leu Asn Lys Ile Cys Ile Gly<br>               1475                   1480                   1485 | 4464 |
| aac gtt tgc cga tgt gca gga gaa acc tgt tcc tcg ctc aac cat cag<br>Asn Val Cys Arg Cys Ala Gly Glu Thr Cys Ser Ser Leu Asn His Gln<br>                  1490                   1495                   1500 | 4512 |
| gaa agg att gat gtt cca tta caa att gaa aaa gcc tgc gag acg aat<br>Glu Arg Ile Asp Val Pro Leu Gln Ile Glu Lys Ala Cys Glu Thr Asn<br>         1505                   1510                   1515 | 4560 |
| gtg gat tat gtc tac aaa acc aag ctg ctt cga ata gaa gaa caa gat<br>Val Asp Tyr Val Tyr Lys Thr Lys Leu Leu Arg Ile Glu Glu Gln Asp<br>1520                   1525                   1530                   1535 | 4608 |
| ggt aat gat atc tat gtc atg gat gtt tta gaa gtt att aaa caa ggt<br>Gly Asn Asp Ile Tyr Val Met Asp Val Leu Glu Val Ile Lys Gln Gly<br>                  1540                   1545                   1550 | 4656 |
| act gac gaa aat cca cga gca aag acc cac cag tac ata agt caa agg<br>Thr Asp Glu Asn Pro Arg Ala Lys Thr His Gln Tyr Ile Ser Gln Arg<br>               1555                   1560                   1565 | 4704 |
| aaa tgc cag gag gct ctg aat ctg aag gtg aat gat gat tat ctg atc<br>Lys Cys Gln Glu Ala Leu Asn Leu Lys Val Asn Asp Asp Tyr Leu Ile<br>                  1570                   1575                   1580 | 4752 |
| tgg ggt tcc agg agt gac ctg ttg ccc acg aaa gat aaa att tcc tac<br>Trp Gly Ser Arg Ser Asp Leu Leu Pro Thr Lys Asp Lys Ile Ser Tyr<br>1585                   1590                   1595 | 4800 |
| atc att aca aag aac aca tgg att gag aga tgg cca cat gaa gac gaa<br>Ile Ile Thr Lys Asn Thr Trp Ile Glu Arg Trp Pro His Glu Asp Glu<br>1600                   1605                   1610                   1615 | 4848 |
| tgt cag gaa gaa gaa ttc caa aag ttg tgt gat gac ttt gct cag ttt<br>Cys Gln Glu Glu Glu Phe Gln Lys Leu Cys Asp Asp Phe Ala Gln Phe<br>                  1620                   1625                   1630 | 4896 |
| agc tac aca ttg act gag ttt ggc tgc cct act taa aagttcagaa<br>Ser Tyr Thr Leu Thr Glu Phe Gly Cys Pro Thr *<br>               1635                   1640 | 4942 |
| gaatcaatga taggaaggaa attctcagaa gacagatttt tgagccaatg catatatgtt | 5002 |
| actttgcctc ttgatctttt agtttatgt caatttgctc tgttattttc ccttaaattg | 5062 |
| tttatacata aaataaataa tcgatttctt actttgatat gttcttgatt tttaataaac | 5122 |
| aatggtgatt catgattatt tttttcttct tctgatccgt ccaatatttg aagtgctctg | 5182 |
| aacagagcac ttatggagta atgttttagt gatggatgaa taagttggtg agtcaatatt | 5242 |
| atcaggccct atatactctt atggaagatc gatttgtacc caaagaaaca tagattgaaa | 5302 |
| tgtgttactt tgaaaacaga ggtttcagtt gtatatgttt acacttggat acaatcttaa | 5362 |
| ctcttaataa acactgatct cagaacattt aacagctgct atttaataat gacaaaatat | 5422 |
| tctttgactg cacccacaga aaacattgca ttacattaga atgggtttta tcagatgact | 5482 |
| aagtctgcta gacttgccat ctgtcaaaat gtgcctcttc cccagctcca actttaagga | 5542 |
| tagtaactaa tagatgttct ctcattggct cctgacagag gtgtgggtagc cactgagttt | 5602 |

```
                                    -continued
cccctggatga cactagaagc tggcagcaca ctgcagcctg gtggaggggc ctcttttgct    5662
atcccatgag cttctattca tcctcttatc tgttgggatg gggatgggac gtctctgatt    5722
ttccaggtat acaggtgatc tcatttacta acatcaccac taacttcaag gattggttga    5782
ggggttatgc caatgtgatt gaaggtttca cccatgtgaa tctattctcc aatcccaatg    5842
ctgtatctat gctgctcatt tctgcttgta aaatggtat  aaaaagaata acactgccc     5902 aggcagtcag acatctttgg acactgaaaa aaaaaaaaaa aaaaaa                   5948
```

<210> SEQ ID NO 4
<211> LENGTH: 1642
<212> TYPE: PRT
<213> ORGANISM: Naja kaouthia

<400> SEQUENCE: 4

```
Met Glu Arg Met Ala Leu Tyr Leu Val Ala Leu Leu Ile Gly Phe
 1               5                  10                  15

Pro Gly Ser Ser His Gly Ala Leu Tyr Thr Leu Ile Thr Pro Ala Val
                20                  25                  30

Leu Arg Thr Asp Thr Glu Glu Gln Ile Leu Val Glu Ala His Gly Asp
            35                  40                  45

Ser Thr Pro Lys Gln Leu Asp Ile Phe Val His Asp Phe Pro Arg Lys
        50                  55                  60

Gln Lys Thr Leu Phe Gln Thr Arg Val Asp Met Asn Pro Ala Gly Gly
    65                  70                  75                  80

Met Leu Val Thr Pro Thr Ile Glu Ile Pro Ala Lys Glu Val Ser Thr
                85                  90                  95

Asp Ser Arg Gln Asn Gln Tyr Val Val Gln Val Thr Gly Pro Gln
                100                 105                 110

Val Arg Leu Glu Lys Val Val Leu Leu Ser Tyr Gln Ser Ser Phe Leu
            115                 120                 125

Phe Ile Gln Thr Asp Lys Gly Ile Tyr Thr Pro Gly Ser Pro Val Leu
        130                 135                 140

Tyr Arg Val Phe Ser Met Asp His Asn Thr Ser Lys Met Asn Lys Thr
    145                 150                 155                 160

Val Ile Val Glu Phe Gln Thr Pro Glu Gly Ile Leu Val Ser Ser Asn
                165                 170                 175

Ser Val Asp Leu Asn Phe Phe Trp Pro Tyr Asn Leu Pro Asp Leu Val
            180                 185                 190

Ser Leu Gly Thr Trp Arg Ile Val Ala Lys Tyr Glu His Ser Pro Glu
        195                 200                 205

Asn Tyr Thr Ala Tyr Phe Asp Val Arg Lys Tyr Val Leu Pro Ser Phe
    210                 215                 220

Glu Val Arg Leu Gln Pro Ser Glu Lys Phe Phe Tyr Ile Asp Gly Asn
225                 230                 235                 240

Glu Asn Phe His Val Ser Ile Thr Ala Arg Tyr Leu Tyr Gly Glu Glu
                245                 250                 255

Val Glu Gly Val Ala Phe Val Leu Phe Gly Val Lys Ile Asp Asp Ala
            260                 265                 270

Lys Lys Ser Ile Pro Asp Ser Leu Thr Arg Ile Pro Ile Ile Asp Gly
        275                 280                 285

Asp Gly Lys Ala Thr Leu Lys Arg Asp Thr Phe Arg Ser Arg Phe Pro
    290                 295                 300

Asn Leu Asn Glu Leu Val Gly His Thr Leu Tyr Ala Ser Val Thr Val
305                 310                 315                 320
```

```
Met Thr Glu Ser Gly Ser Asp Met Val Val Thr Gln Ser Gly Ile
            325                 330                 335

His Ile Val Ala Ser Pro Tyr Gln Ile His Phe Thr Lys Thr Pro Lys
            340                 345                 350

Tyr Phe Lys Pro Gly Met Pro Tyr Glu Leu Thr Val Tyr Val Thr Asn
            355                 360                 365

Pro Asp Gly Ser Pro Ala Ala His Val Pro Val Val Ser Glu Ala Phe
            370                 375                 380

His Ser Met Gly Thr Thr Leu Ser Asp Gly Thr Ala Lys Leu Ile Leu
385                 390                 395                 400

Asn Ile Pro Leu Asn Ala Gln Ser Leu Pro Ile Thr Val Arg Thr Asn
            405                 410                 415

His Gly Asp Leu Pro Arg Glu Arg Gln Ala Thr Lys Ser Met Thr Ala
            420                 425                 430

Ile Ala Tyr Gln Thr Gln Gly Gly Ser Gly Asn Tyr Leu His Val Ala
            435                 440                 445

Ile Thr Ser Thr Glu Ile Lys Pro Gly Asp Asn Leu Pro Val Asn Phe
            450                 455                 460

Asn Val Lys Gly Asn Ala Asn Ser Leu Lys Gln Ile Lys Tyr Phe Thr
465                 470                 475                 480

Tyr Leu Ile Leu Asn Lys Gly Lys Ile Phe Lys Val Gly Arg Gln Pro
            485                 490                 495

Arg Arg Asp Gly Gln Asn Leu Val Thr Met Asn Leu His Ile Thr Pro
            500                 505                 510

Asp Leu Ile Pro Ser Phe Arg Phe Val Ala Tyr Gln Val Gly Asn
            515                 520                 525

Asn Glu Ile Val Ala Asp Ser Val Trp Val Asp Val Lys Asp Thr Cys
            530                 535                 540

Met Gly Thr Leu Val Val Lys Gly Asp Asn Leu Ile Gln Met Pro Gly
545                 550                 555                 560

Ala Ala Met Lys Ile Lys Leu Glu Gly Asp Pro Gly Ala Arg Val Gly
            565                 570                 575

Leu Val Ala Val Asp Lys Ala Val Tyr Val Leu Asn Asp Lys Tyr Lys
            580                 585                 590

Ile Ser Gln Ala Lys Ile Trp Asp Thr Ile Glu Lys Ser Asp Phe Gly
            595                 600                 605

Cys Thr Ala Gly Ser Gly Gln Asn Asn Leu Gly Val Phe Glu Asp Ala
            610                 615                 620

Gly Leu Ala Leu Thr Thr Ser Thr Asn Leu Asn Thr Lys Gln Arg Ser
625                 630                 635                 640

Ala Ala Lys Cys Pro Gln Pro Ala Asn Arg Arg Arg Ser Val
            645                 650                 655

Leu Leu Leu Asp Ser Asn Ala Ser Lys Ala Ala Glu Phe Gln Asp Gln
            660                 665                 670

Asp Leu Arg Lys Cys Cys Glu Asp Val Met His Glu Asn Pro Met Gly
            675                 680                 685

Tyr Thr Cys Glu Lys Arg Ala Lys Tyr Ile Gln Glu Gly Asp Ala Cys
            690                 695                 700

Lys Ala Ala Phe Leu Glu Cys Cys Arg Tyr Ile Lys Gly Val Arg Asp
705                 710                 715                 720

Glu Asn Gln Arg Glu Ser Glu Leu Phe Leu Ala Arg Asp Asp Asn Glu
            725                 730                 735

Asp Gly Phe Ile Ala Asp Ser Asp Ile Ile Ser Arg Ser Asp Phe Pro
            740                 745                 750
```

-continued

Lys Ser Trp Leu Trp Leu Thr Lys Asp Leu Thr Glu Glu Pro Asn Ser
                755             760             765

Gln Gly Ile Ser Ser Lys Thr Met Ser Phe Tyr Leu Arg Asp Ser Ile
        770             775             780

Thr Thr Trp Val Val Leu Ala Val Ser Phe Thr Pro Thr Lys Gly Ile
785             790             795             800

Cys Val Ala Glu Pro Tyr Glu Ile Arg Val Met Lys Val Phe Phe Ile
            805             810             815

Asp Leu Gln Met Pro Tyr Ser Val Val Lys Asn Glu Gln Val Glu Ile
        820             825             830

Arg Ala Ile Leu His Asn Tyr Val Asn Glu Asp Ile Tyr Val Arg Val
        835             840             845

Glu Leu Leu Tyr Asn Pro Ala Phe Cys Ser Ala Ser Thr Lys Gly Gln
        850             855             860

Arg Tyr Arg Gln Gln Phe Pro Ile Lys Ala Leu Ser Ser Arg Ala Val
865             870             875             880

Pro Phe Val Ile Val Pro Leu Glu Gln Gly Leu His Asp Val Glu Ile
            885             890             895

Lys Ala Ser Val Gln Glu Ala Leu Trp Ser Asp Val Arg Lys Lys
        900             905             910

Leu Lys Val Val Pro Glu Gly Val Gln Lys Ser Ile Val Thr Ile Val
        915             920             925

Lys Leu Asp Pro Arg Ala Lys Gly Val Gly Gly Thr Gln Leu Glu Val
        930             935             940

Ile Lys Ala Arg Lys Leu Asp Asp Arg Val Pro Asp Thr Glu Ile Glu
945             950             955             960

Thr Lys Ile Ile Ile Gln Gly Asp Pro Val Ala Gln Ile Ile Glu Asn
                965             970             975

Ser Ile Asp Gly Ser Lys Leu Asn His Leu Ile Ile Thr Pro Ser Gly
            980             985             990

Cys Gly Glu Gln Asn Met Ile Arg Met Ala Ala Pro Val Ile Ala Thr
        995             1000            1005

Tyr Tyr Leu Asp Thr Thr Glu Gln Trp Glu Thr Leu Gly Ile Asn Arg
        1010            1015            1020

Arg Thr Glu Ala Val Asn Gln Ile Val Thr Gly Tyr Ala Gln Gln Met
1025            1030            1035            1040

Val Tyr Lys Lys Ala Asp His Ser Tyr Ala Ala Phe Thr Asn Arg Ala
            1045            1050            1055

Ser Ser Ser Trp Leu Thr Ala Tyr Val Val Lys Val Phe Ala Met Ala
            1060            1065            1070

Ala Lys Met Val Ala Gly Ile Ser His Glu Ile Ile Cys Gly Gly Val
        1075            1080            1085

Arg Trp Leu Ile Leu Asn Arg Gln Gln Pro Asp Gly Ala Phe Lys Glu
        1090            1095            1100

Asn Ala Pro Val Leu Ser Gly Thr Met Gln Gly Gly Ile Gln Gly Ala
1105            1110            1115            1120

Glu Glu Glu Val Tyr Leu Thr Ala Phe Ile Leu Val Ala Leu Leu Glu
            1125            1130            1135

Ser Lys Thr Ile Cys Asn Asp Tyr Val Asn Ser Leu Asp Ser Ser Ile
        1140            1145            1150

Lys Lys Ala Thr Asn Tyr Leu Leu Lys Lys Tyr Glu Lys Leu Gln Arg
        1155            1160            1165

Pro Tyr Thr Thr Ala Leu Thr Ala Tyr Ala Leu Ala Ala Ala Asp Gln

-continued

```
          1170                1175                1180
Leu Asn Asp Asp Arg Val Leu Met Ala Ala Ser Thr Gly Arg Asp His
1185                1190                1195                1200

Trp Glu Glu Tyr Asn Ala His Thr His Asn Ile Glu Gly Thr Ser Tyr
                1205                1210                1215

Ala Leu Leu Ala Leu Leu Lys Met Lys Lys Phe Asp Gln Thr Gly Pro
            1220                1225                1230

Ile Val Arg Trp Leu Thr Asp Gln Asn Phe Tyr Gly Thr Tyr Gly
        1235                1240                1245

Gln Thr Gln Ala Thr Val Met Ala Phe Gln Ala Leu Ala Glu Tyr Glu
            1250                1255                1260

Ile Gln Met Pro Thr His Lys Asp Leu Asn Leu Asp Ile Thr Ile Glu
1265                1270                1275                1280

Leu Pro Asp Arg Glu Val Pro Ile Arg Tyr Arg Ile Asn Tyr Glu Asn
                1285                1290                1295

Ala Leu Leu Ala Arg Thr Val Glu Thr Lys Leu Asn Gln Asp Ile Thr
            1300                1305                1310

Val Thr Ala Ser Gly Asp Gly Lys Ala Thr Met Thr Ile Leu Thr Phe
            1315                1320                1325

Tyr Asn Ala Gln Leu Gln Glu Lys Ala Asn Val Cys Asn Lys Phe His
            1330                1335                1340

Leu Asn Val Ser Val Glu Asn Ile His Leu Asn Ala Met Gly Ala Lys
1345                1350                1355                1360

Gly Ala Leu Met Leu Lys Ile Cys Thr Arg Tyr Leu Gly Glu Val Asp
            1365                1370                1375

Ser Thr Met Thr Ile Ile Asp Ile Ser Met Leu Thr Gly Phe Leu Pro
            1380                1385                1390

Asp Ala Glu Asp Leu Thr Arg Leu Ser Lys Gly Val Asp Arg Tyr Ile
            1395                1400                1405

Ser Arg Tyr Glu Val Asp Asn Asn Met Ala Gln Lys Val Ala Val Ile
            1410                1415                1420

Ile Tyr Leu Asn Lys Val Ser His Ser Glu Asp Glu Cys Leu His Phe
1425                1430                1435                1440

Lys Ile Leu Lys His Phe Glu Val Gly Phe Ile Gln Pro Gly Ser Val
            1445                1450                1455

Lys Val Tyr Ser Tyr Tyr Asn Leu Asp Glu Lys Cys Thr Lys Phe Tyr
            1460                1465                1470

His Pro Asp Lys Gly Thr Gly Leu Leu Asn Lys Ile Cys Ile Gly Asn
            1475                1480                1485

Val Cys Arg Cys Ala Gly Glu Thr Cys Ser Ser Leu Asn His Gln Glu
            1490                1495                1500

Arg Ile Asp Val Pro Leu Gln Ile Glu Lys Ala Cys Glu Thr Asn Val
1505                1510                1515                1520

Asp Tyr Val Tyr Lys Thr Lys Leu Leu Arg Ile Glu Glu Gln Asp Gly
                1525                1530                1535

Asn Asp Ile Tyr Val Met Asp Val Leu Glu Val Ile Lys Gln Gly Thr
            1540                1545                1550

Asp Glu Asn Pro Arg Ala Lys Thr His Gln Tyr Ile Ser Gln Arg Lys
            1555                1560                1565

Cys Gln Glu Ala Leu Asn Leu Lys Val Asn Asp Asp Tyr Leu Ile Trp
            1570                1575                1580

Gly Ser Arg Ser Asp Leu Leu Pro Thr Lys Asp Lys Ile Ser Tyr Ile
1585                1590                1595                1600
```

```
Ile Thr Lys Asn Thr Trp Ile Glu Arg Trp Pro His Glu Asp Glu Cys
        1605                1610                1615
Gln Glu Glu Glu Phe Gln Lys Leu Cys Asp Asp Phe Ala Gln Phe Ser
        1620                1625                1630
Tyr Thr Leu Thr Glu Phe Gly Cys Pro Thr
        1635                1640

<210> SEQ ID NO 5
<211> LENGTH: 19
<212> TYPE: PRT
<213> ORGANISM: Artificial Sequence
<220> FEATURE:
<223> OTHER INFORMATION: Vector coded sequence.

<400> SEQUENCE: 5

Arg Ser Pro Trp Pro Gly Val Pro Thr Ser Pro Val Trp Trp Asn Ser
1               5                   10                  15

Ala Asp Ala

<210> SEQ ID NO 6
<211> LENGTH: 31
<212> TYPE: DNA
<213> ORGANISM: Artificial Sequence
<220> FEATURE:
<223> OTHER INFORMATION: Primer HC3H5-1.

<400> SEQUENCE: 6
ggatgccact atgtctatat tggacatatc c                               31

<210> SEQ ID NO 7
<211> LENGTH: 30
<212> TYPE: DNA
<213> ORGANISM: Artificial Sequence
<220> FEATURE:
<223> OTHER INFORMATION: Primer HC3H5-2.

<400> SEQUENCE: 7
tcttctattc gaaccagtcg ggtcttgtac                                 30

<210> SEQ ID NO 8
<211> LENGTH: 35
<212> TYPE: DNA
<213> ORGANISM: Artificial Sequence
<220> FEATURE:
<223> OTHER INFORMATION: Primer HuC3H5-3.

<400> SEQUENCE: 8
gtacaagacc cgactggttc gaatagaaga acaag                           35

<210> SEQ ID NO 9
<211> LENGTH: 36
<212> TYPE: DNA
<213> ORGANISM: Artificial Sequence
<220> FEATURE:
<223> OTHER INFORMATION: Primer HuC3H5-4.

<400> SEQUENCE: 9
tatcatgtaa gcggccgcgt ataaacaatt taaggg                          36

<210> SEQ ID NO 10
<211> LENGTH: 48
<212> TYPE: DNA
<213> ORGANISM: Artificial Sequence
<220> FEATURE:
<223> OTHER INFORMATION: Primer HC3SigRemF.
```

```
<400> SEQUENCE: 10
agatctccat ggaagcttag cgctgggagt cccatgtact ctatcatc                    48

<210> SEQ ID NO 11
<211> LENGTH: 20
<212> TYPE: DNA
<213> ORGANISM: Artificial Sequence
<220> FEATURE:
<223> OTHER INFORMATION: Primer HC3SigRemR.

<400> SEQUENCE: 11
gcgtcccgcc ttcaacagcc                                                   20

<210> SEQ ID NO 12
<211> LENGTH: 24
<212> TYPE: DNA
<213> ORGANISM: Artificial Sequence
<220> FEATURE:
<223> OTHER INFORMATION: Primer HC3H5-3-F1.

<400> SEQUENCE: 12
tctgtgtggc agacccttc gagg                                               24

<210> SEQ ID NO 13
<211> LENGTH: 35
<212> TYPE: DNA
<213> ORGANISM: Artificial Sequence
<220> FEATURE:
<223> OTHER INFORMATION: Primer HC3H5-5-R1.

<400> SEQUENCE: 13
cgttaccaat acatatcttg ttcagctttc catcc                                  35

<210> SEQ ID NO 14
<211> LENGTH: 35
<212> TYPE: DNA
<213> ORGANISM: Artificial Sequence
<220> FEATURE:
<223> OTHER INFORMATION: Primer HuCC3H5-3-F2.

<400> SEQUENCE: 14
ggatggaaag ctgaacaaga tatgtattgg taacg                                  35

<210> SEQ ID NO 15
<211> LENGTH: 31
<212> TYPE: DNA
<213> ORGANISM: Artificial Sequence
<220> FEATURE:
<223> OTHER INFORMATION: Primer HuC3H5-3-R2.

<400> SEQUENCE: 15
catccatgac atagatatca ttaccatctt g                                      31

<210> SEQ ID NO 16
<211> LENGTH: 32
<212> TYPE: DNA
<213> ORGANISM: Artificial Sequence
<220> FEATURE:
<223> OTHER INFORMATION: HuC3H5-5-1R.

<400> SEQUENCE: 16
gcaactgtgc gttatacatt gtcaccaccg ac                                     32

<210> SEQ ID NO 17
<211> LENGTH: 32
<212> TYPE: DNA
```

```
<213> ORGANISM: Artificial Sequence
<220> FEATURE:
<223> OTHER INFORMATION: HuC3H5-5-2F.

<400> SEQUENCE: 17
gtcggtggtg acaatgtata acgcacagtt gc                                   32

<210> SEQ ID NO 18
<211> LENGTH: 41
<212> TYPE: DNA
<213> ORGANISM: Artificial Sequence
<220> FEATURE:
<223> OTHER INFORMATION: HC3H5-4-R1.

<400> SEQUENCE: 18
gagaaggcct gttcctttat ccggatggta gaaccgggta c                         41

<210> SEQ ID NO 19
<211> LENGTH: 35
<212> TYPE: DNA
<213> ORGANISM: Artificial Sequence
<220> FEATURE:
<223> OTHER INFORMATION: HCC3H5-4-F2.

<400> SEQUENCE: 19
ccggttctac catccggata aaggaacagg ccttc                                35

<210> SEQ ID NO 20
<211> LENGTH: 31
<212> TYPE: DNA
<213> ORGANISM: Artificial Sequence
<220> FEATURE:
<223> OTHER INFORMATION: HC3H5-3-R2.

<400> SEQUENCE: 20
catccatgac atagatatca ttaccatctt g                                    31

<210> SEQ ID NO 21
<211> LENGTH: 31
<212> TYPE: DNA
<213> ORGANISM: Artificial Sequence
<220> FEATURE:
<223> OTHER INFORMATION: HuC3H5-F1.

<400> SEQUENCE: 21
ggatgccact atgtctatat tggacatatc c                                    31

<210> SEQ ID NO 22
<211> LENGTH: 33
<212> TYPE: DNA
<213> ORGANISM: Artificial Sequence
<220> FEATURE:
<223> OTHER INFORMATION: HuC3H5-2R1.

<400> SEQUENCE: 22
cccgatgatg tagctgagtt tatctttcgt ggg                                  33

<210> SEQ ID NO 23
<211> LENGTH: 33
<212> TYPE: DNA
<213> ORGANISM: Artificial Sequence
<220> FEATURE:
<223> OTHER INFORMATION: HuC3H5-2F2.

<400> SEQUENCE: 23
cccacgaaag ataaactcag ctacatcatc ggg                                  33
```

```
<210> SEQ ID NO 24
<211> LENGTH: 22
<212> TYPE: DNA
<213> ORGANISM: Artificial Sequence
<220> FEATURE:
<223> OTHER INFORMATION: HuC3H5-2-R2.

<400> SEQUENCE: 24
aattggagct ccaccgcggt gg                                                    22
```

HUMAN COMPLEMENT C3 DERIVATES WITH COBRA VENOM FACTOR-LIKE FUNCTION

RELATED APPLICATIONS

This International application claims priority to U.S. Provisional Applications 60/567,069, filed Apr. 30, 2004, 60/653,247, filed Feb. 14, 2005, and 60/667,352, filed Mar. 30, 2005, each of which is incorporated by reference in its entirety.

FIELD OF THE INVENTION

The invention relates generally to chimeric derivatives of Human Complement C3 having a substitution of a portion of a human C3 protein with a corresponding portion of a Cobra Venom Factor (CVF) protein. Preferably, a portion of the alpha chain of C3 is substituted with the corresponding portion of CVF.

BACKGROUND OF THE INVENTION

The third component of complement, C3, plays a pivotal role in both the classical and alternative pathways of complement activation, and many of the physiologic C3 activation products have important functions in the immune response and host defense. In the alternative pathway, the activated form of C3, C3b, is a structural subunit of the C3 convertase. This bimolecular enzyme consists of C3b and Bb, the activated form of factor B. This enzyme is formed by the binding of C3b to factor B that is subsequently cleaved by factor D, resulting in the formation of the C3 convertase, C3b,Bb, and the release of the activation peptide Ba. The C3 convertase activates C3 by cleaving the molecule into C3b and the anaphylatoxin, C3a. The C3b molecule will bind to a cell or particle in close proximity to the C3 convertase. Eventually, the bound C3b will allow for the activation of C5 into C5b and the anaphylatoxin, C5a. C5 activation occurs by the same C3b,Bb enzyme that can cleave C5 when it is bound to an additional C3b molecule to produce a trimolecular complex composed of $(C3b)_2$,Bb. This C5-cleaving trimolecular enzyme is called C5 convertase. Inasmuch as the activation of both C3 and C5 occurs at the identical active site in the Bb subunit, the enzyme is also called C3/C5 convertase; and only one EC number has been assigned (EC 3.4.21.47).

Cobra venom contains a structural and functional analog of C3 called cobra venom factor (CVF). This molecule can bind factor B in human and mammalian serum to form the complex, CVF,B, which is also cleaved by factor D into the bimolecular enzyme CVF,Bb and Ba. The bimolecular complex CVF,Bb is a C3/C5 convertase that activates C3 and C5 analogously to the C3/C5 convertase formed with C3b. Although the two C3/C5 convertases, C3b,Bb and CVF,Bb, share the same molecular architecture, the active site-bearing Bb subunit, and the substrate specificity, the two enzymes exhibit significant functional differences. The CVF,Bb enzyme is physiochemically far more stable than C3b,Bb, it is resistant to inactivation by the regulatory proteins factors H and I, it exhibits different kinetic properties, and it does not require additional C3b for C5 cleavage.

CVF and mammalian C3 have been shown to exhibit several structural similarities including immunologic cross-reactivity, amino acid composition, circular dichroism spectra, secondary structure, electron microscopic ultrastructure, and amino acid sequence. Nevertheless, significant structural differences exist between the two molecules. Whereas C3 is a two-chain molecule with an apparent molecular mass, dependent on the species, of 170 to 190 kDa, CVF is a three-chain molecule with an apparent molecular mass of 149 kDa that resembles C3c, one of the physiologic activation products of C3. Another significant structural difference between C3 and CVF lies in their glycosylation: CVF has a 7.4% (w/w) carbohydrate content consisting mainly of N-linked complex-type chains with unusual α-galactosyl residues at the non-reducing termini. In contrast, human and rat C3 exhibit a lower extent of glycosylation with different structures of their oligosaccharide chains.

Whereas CVF,Bb and C3b,Bb are both C3/C5 convertases, they exhibit important differences. The CVF-containing enzyme is far more stable than the C3-containing enzyme. Both convertases will spontaneously decay into their two respective subunits. However, the intrinsic half-life (stability) of the CVF-containing convertase is approximately 7 hours at 37° C., several hundred times longer than the C3-containing enzyme with an intrinsic half-life of approximately 1.5 minutes. Furthermore, the CVF-containing enzyme as well as free CVF are not subject to regulation by the complement regulatory proteins factors H and I. The combination of the long intrinsic half-life and the resistance to regulation of the CVF-containing enzymes allows CVF to continuously activate C3 and C5 (and subsequently other complement components), ultimately resulting in depletion of the serum complement activity.

Based on the involvement of the complement system in multiple diseases, including diseases of major prevalence, the last decade has seen the development of multiple anti-complementary agents to interfere with the unwanted complement activation process in these disease states. All complement-oriented drug development attempts are based on inhibiting the activation of complement, while CVF acts by depleting complement in serum. Of interest for the treatment of diseases of complement activation is a C3-type molecule which combines the non- or low immunogenicity of C3, with the complement-depleting function of CVF.

SUMMARY OF THE INVENTION

The following listing of embodiments is a nonlimiting statement of various aspects of the invention. Other aspects and variations will be evident in light of the entire disclosure.

Some embodiments include one or more modified human complement C3 proteins, which can have a substitution of a portion of a human C3 protein, with a corresponding portion of a Cobra Venom Factor protein of a sequence substantially related thereto. In some embodiments the substituted portion of the CVF can be within the alpha chain of C3. In other embodiments, the substituted portion of the CVF can be a C-terminal portion of the alpha chain of C3. In some embodiments, the substituted C-terminal portion can include amino acid 1663 of the human C3 protein. In some embodiments, the substituted C-terminal portion can be an internal portion that does not extend through the entire C-terminus of the human C3 protein. In further embodiments, the modified protein can have substantially the same number of amino acid residues as an unmodified human C3 protein. In some embodiments, the substitution can include any positions within amino acid positions 700-1663 of the human C3 protein. Other embodiments are human complement C3 proteins, which can have a substitution of a portion of a human C3 protein, with a corresponding portion of a Cobra Venom Factor protein of a sequence substantially related thereto and which can have at least two substitutions. In some embodiments, the substitution has a selected beginning position and a selected last position; in some such embodiments, the beginning position can be, for example, 749, 874, 936, 994, 1264, 1348, 1496, 1504, 1550, and the like; the last position can be, for example, 784, 921, 970 1324, 1550, 1617, 1663, and the like. In preferred embodiments, the one or more substitutions can include any of amino acids: 1550-1663, 1504-1663, 1348-1663, 1550-1617, 1504-1617, 1496-1663, 1348-1617, 1496-1617, 1264-1324, 749-784, 874-921, 994-1663, 994-1550 and 936-970. In some embodiments, the substituted portion of CVF can be within the beta chain of C3.

In some embodiments, the modified C3 protein can have an affinity for factor B and can support formation of a convertase. In some embodiments, the resulting convertase can cleave C3 and not C5. In further embodiments, the convertase can have an intrinsic half-life between about 1.5 minutes and about 7 hours at 37° C. In some embodiments, the resulting convertase can have an intrinsic half-life of at least about 7 hours at 37° C.

In some embodiments, the modified C3 protein can be expressed as a single chain protein. In some embodiments, the modified C3 protein can be cleaved into at least two chains in a form that resembles C3. In further embodiments, the modified C3 protein can be cleaved to release a C3a portion therefrom. In some embodiments, the modified protein can have an additional 1 to about 19 amino acids at the N-terminus that are not encoded by C3 or CVF. In some embodiments, the modified protein can include a non-C3 signal peptide, such as a *Drosophila* Bip signal sequence. In some embodiments, the modified C3 protein can have modified affinity for factor B and/or factor D. In some embodiments, the modified protein can show partial or complete resistance to Factor H and/or Factor I. In some embodiments, the modified C3 protein can be substantially non-immunogenic.

Other embodiments can include a method for depleting complement by administering a modified C3 protein to a patient in an amount effective for the depletion of complement. In some embodiments, the administration can be local. In further embodiments, the local administration can be into an organ, subcutaneously, into a cavity, or into a tissue. In other embodiments, the local administration can employ a targeting function capable of concentrating the modified C3 protein in a desired location. In further embodiments, the targeting function can include using an antibody conjugated to the modified C3 protein. In some embodiments, the administration can be a systemic administration, such as intravenous or intraperitoneal.

Further embodiments can be methods for avoiding or ameliorating reperfusion injury in a patient by delivering a modified C3 protein to the patient, sufficient to deplete complement; and permitting reperfusion in the patient. In some embodiments, the delivering step can include injecting the modified C3 protein into an artery. In other embodiments, the delivering step can include a local delivery of the modified C3 protein. In other embodiments, the delivering step can include a systemic delivery of the modified C3 protein. In some embodiments, reperfusion can include opening a blocked artery. In some embodiments, the reperfusion can occur in connection with transplantation of an organ.

Some embodiments can include methods for increasing the efficiency and/or effectiveness of gene therapy by delivering a modified C3 protein in an amount sufficient to deplete complement, providing the gene therapy; and observing an enhanced result therefrom.

Some embodiments can include methods of increasing delivery of a therapeutic or diagnostic agent by delivering a modified C3 protein sufficient to increase blood flow; and providing the therapeutic or diagnostic agent. In some embodiments, the method can include chemically linking the modified C3 protein to an antibody with an affinity for a specific tissue prior to the delivering step. In some embodiments, the antibody can be attached to the modified C3 by recombinant DNA technology. In some embodiments the antibody can be a monoclonal antibody.

Some embodiments include methods of treating an autoimmune disease, comprising administering the modified C3 protein sufficient to deplete complement. In some embodiments, the administration can be episodic and corresponds to periods of at least one elevated disease symptom. In some embodiments, the autoimmune disease can be any of asthma, systemic lupus erythematosus, glomerulonephritis, rheumatoid arthritis, Alzheimer's disease, multiple sclerosis, myocardial ischemia, reperfusion, sepsis, hyperacute rejection, transplant rejection, cardiopulmonary bypass, myocardial infarction, angioplasty, nephritis, dermatomyositis, pemphigoid, spinal cord injury and Parkinson's disease.

Some embodiments include methods of mimicking the properties of CVF in a human protein, by, for example, substituting a portion of a human complement C3 protein with the corresponding portion of a Cobra Venom Factor (CVF) protein. In some embodiments the portion can be within the alpha chain of C3. In other embodiments, the portion can be a C-terminal portion of the alpha chain of C3. In some embodiments, the C-terminal portion can include amino acid 1663 of the human C3 protein. In some embodiments, the substituted C-terminal portion can be an internal portion that does not extend through the entire C-terminus of the human C3 protein.

Other embodiments include methods of selecting a modified C3 protein, by characterizing at least one property of the modified C3 protein to form a function profile of the modified protein; and matching the function profile with a disease or condition to be treated. In some embodiments, at least one property can be selected from the group consisting of: convertase activity, convertase formation, convertase stability, susceptibility to Factor H, susceptibility to Factor I, ability to cleave C3, and ability to cleave C5. In some embodiments, the selected C3 protein participates in formation of a convertase adapted for treatment of a chronic condition. In some embodiments, the adaptation can include any of, for example, long plasma half-life, high stability, resistance to Factor H, resistance to Factor I, and the like. In some embodiments, the convertase can be adapted for treatment of a reperfusion injury. In other embodiments, the adaptation can be any of, for example, high convertase activity, resistance to Factor H, resistance to Factor I and the like.

Some embodiments include a nucleic acid sequence encoding a modified C3 protein, and/or a vector including the nucleic acid and/or a host cell containing the vector. In some embodiments, the host cell can be any of: a *Drosophila* S2 cell, an Sf9 cell, a CHO cell, a COS-7 cell, a HiFive cell, a yeast cell, a BHK cell, an HEK293 cell, and an *E. coli* cell.

Some embodiments include a composition that can include the modified human complement C3 protein and a pharmaceutically acceptable carrier and/or the nucleic acid.

Some embodiments include an expression system expressing the modified C3 protein. In some embodiment, the expression system include a cell selected from the group consisting of: a *Drosophila* S2 cell, an Sf9 cell, a CHO cell, a COS-7 cell, a HiFive cell, a yeast cell, a BHK cell, an HEK293 cell, and an *E. coli* cell.

BRIEF DESCRIPTION OF THE DRAWINGS

FIG. 1 depicts the chain structures of C3 and CVF with shaded portions present in the mature proteins.

FIG. 2 shows a map of the original CVF/cobra C3 hybrid proteins, showing the region of CVF that was substituted with cobra C3 sequences in each of the five hybrid proteins.

Figure 3A:
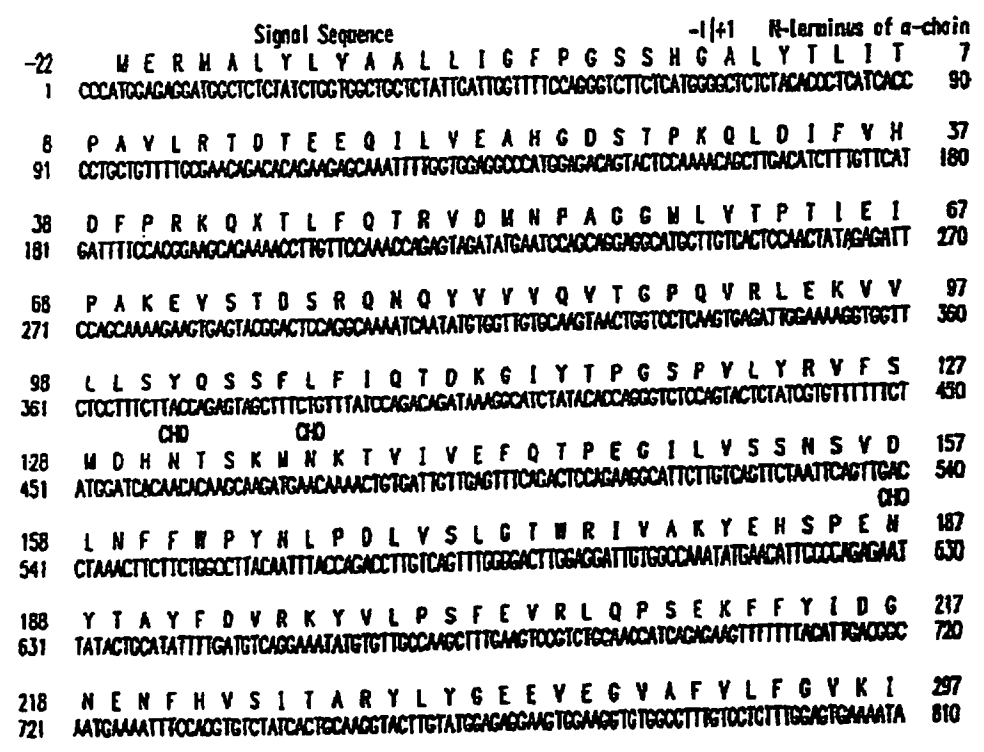
Figure 3B:
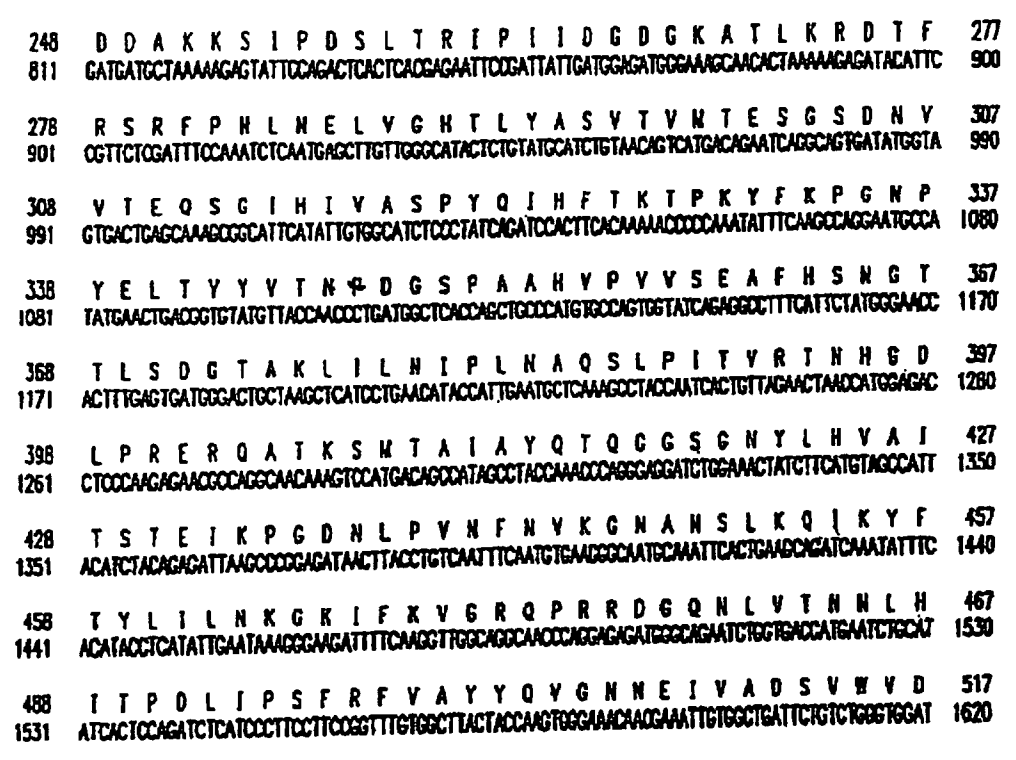
Figure 3C:
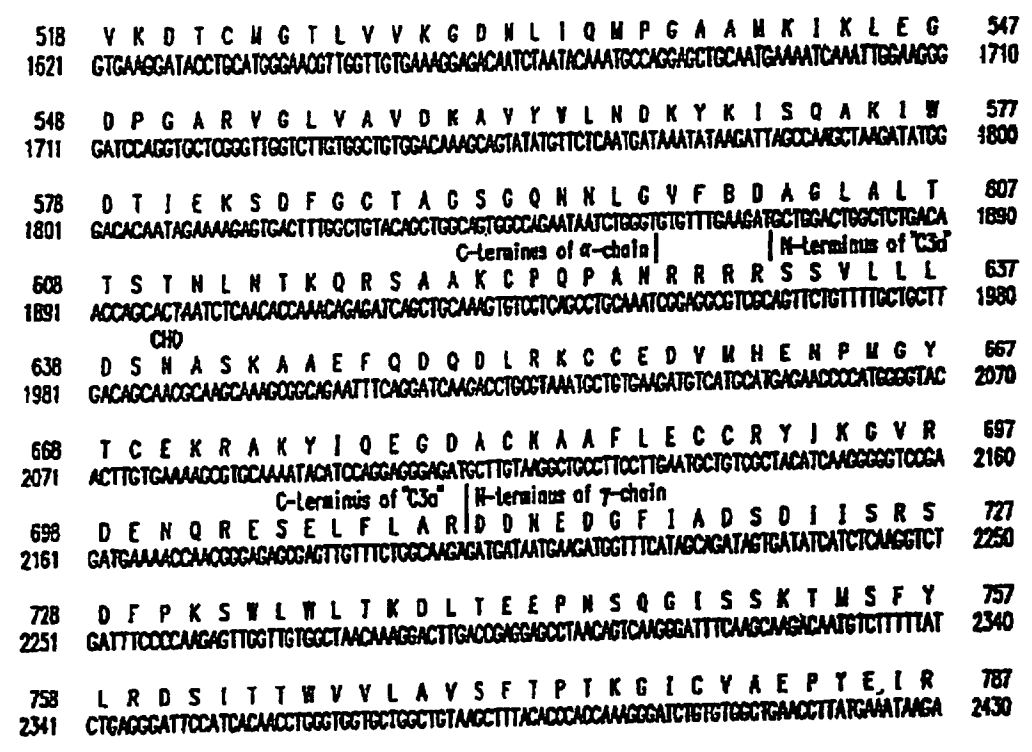
Figure 3D:
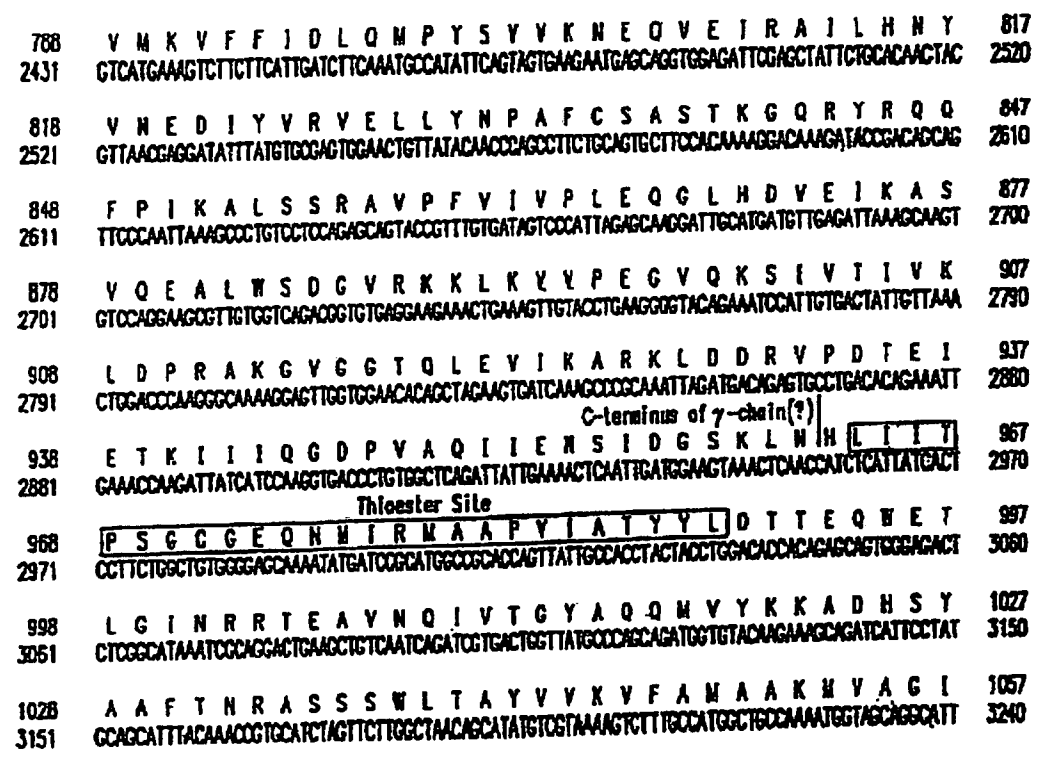
Figure 3E:
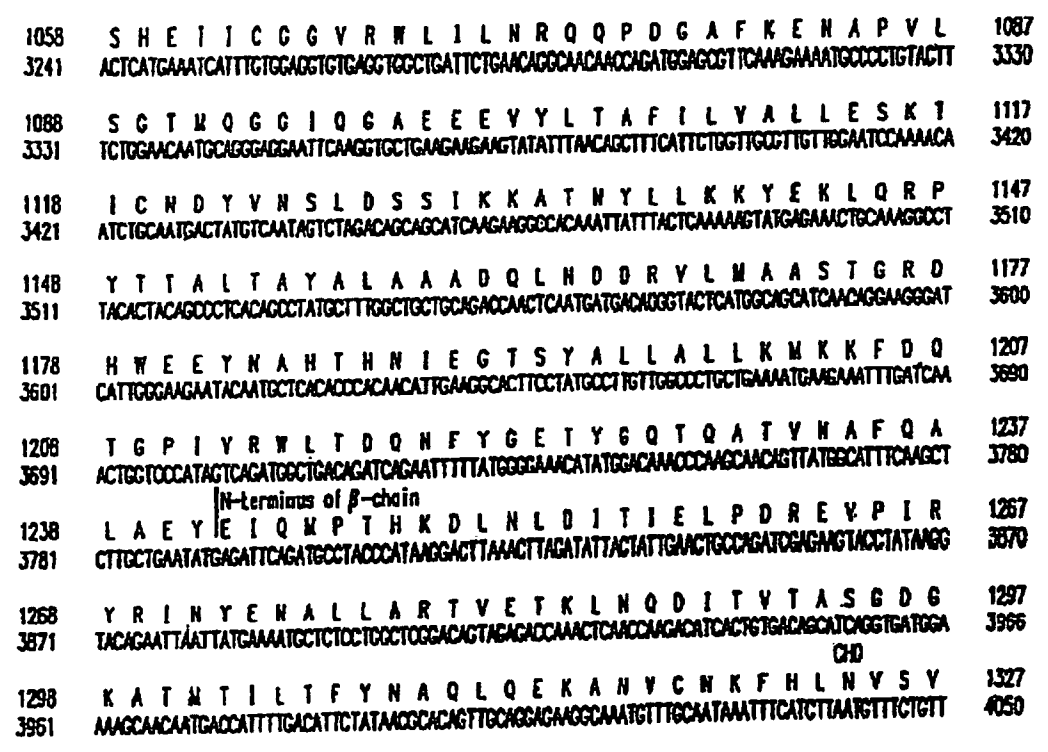
Figure 3F:
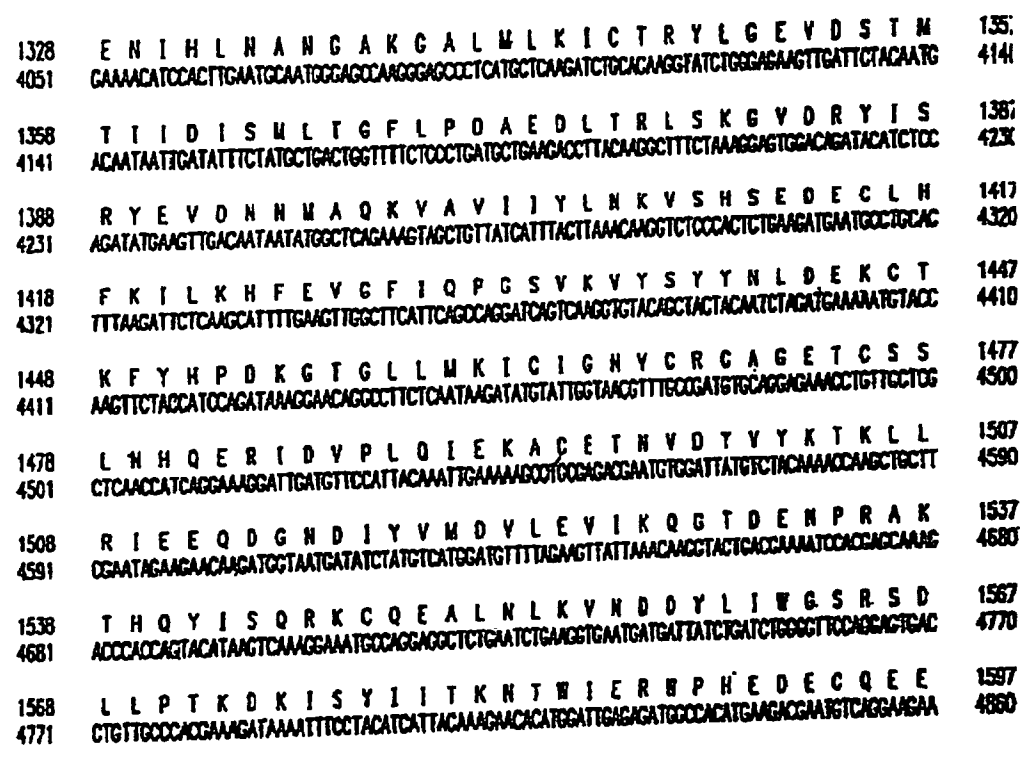
Figure 3G:
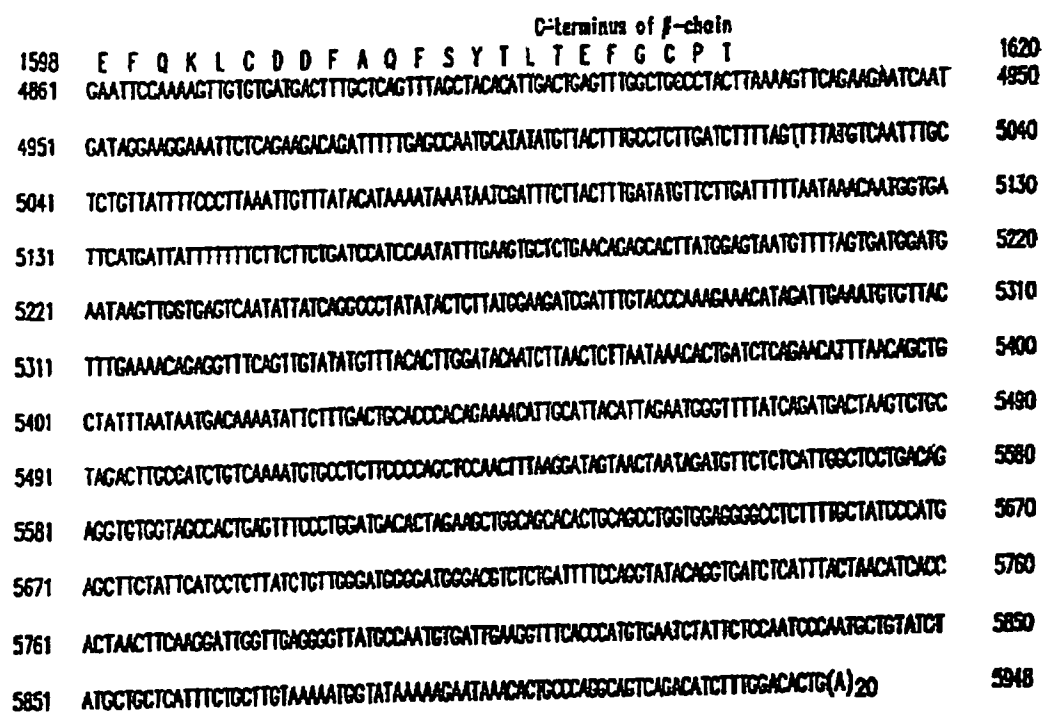

FIGS. 3A-3G show the cDNA and derived amino acid sequence of CVF1 (SEQ ID NOs:3 and 4). The $NH_2$— and C-termini of the α-, γ-, and β-chains, functionally important regions, and known ligand binding sites are indicated. Amino acid residue numbering starts at the $NH_2$-terminus of the pro-CVF1 molecule;

FIG. 8 is a summary of the results for the activity measurements of the three modified human C3 proteins: HC3-1348, HC3-1504, and HC3-1550 as compared to CVF and Human C3b.

Figure 1:
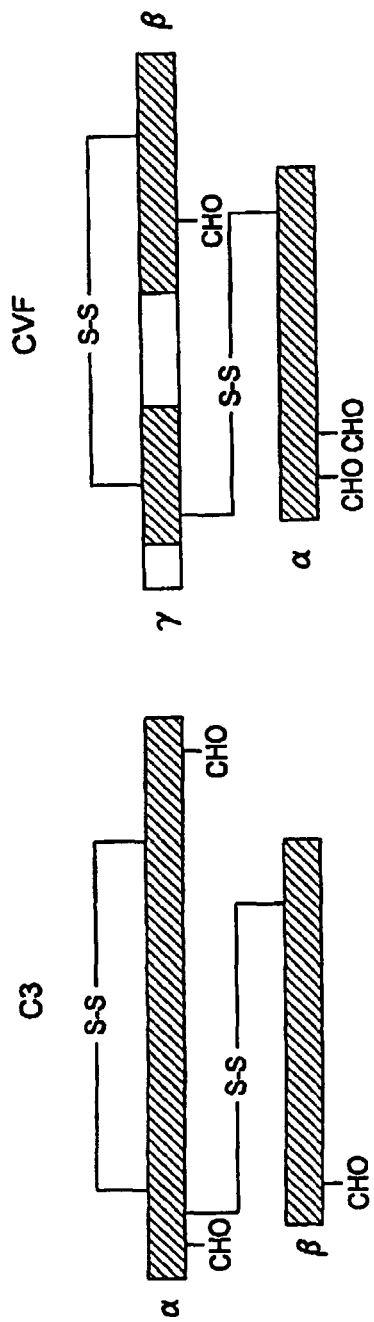
Figure 2:
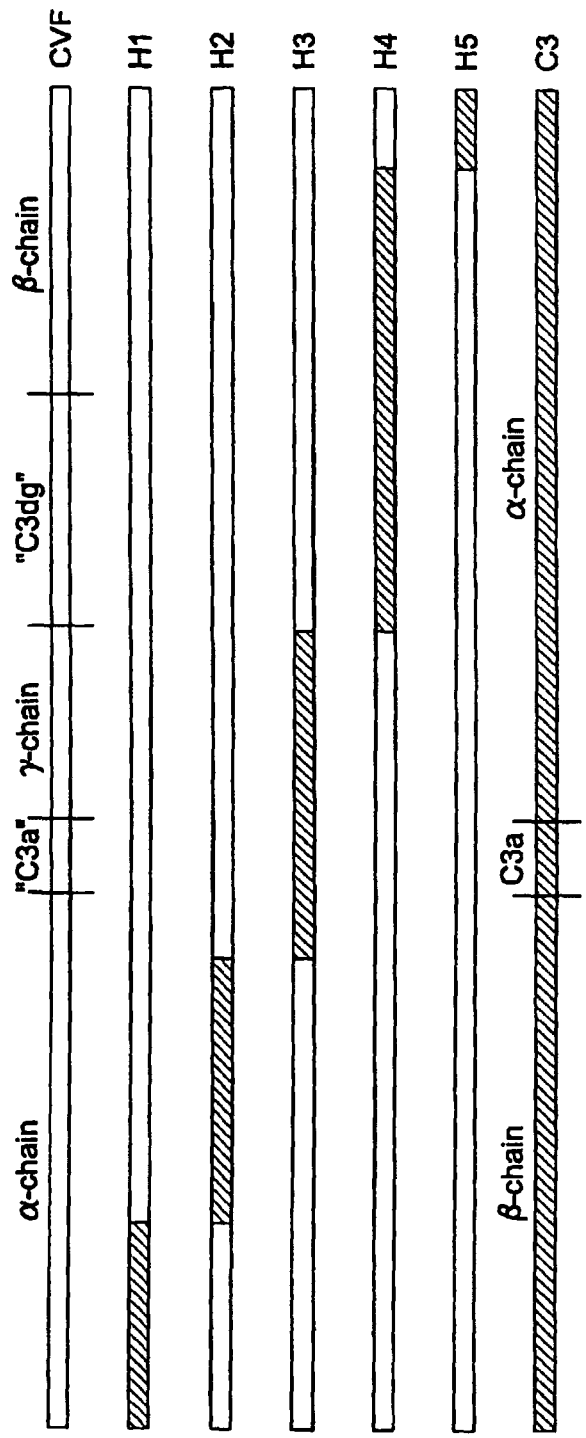
Figure 4:
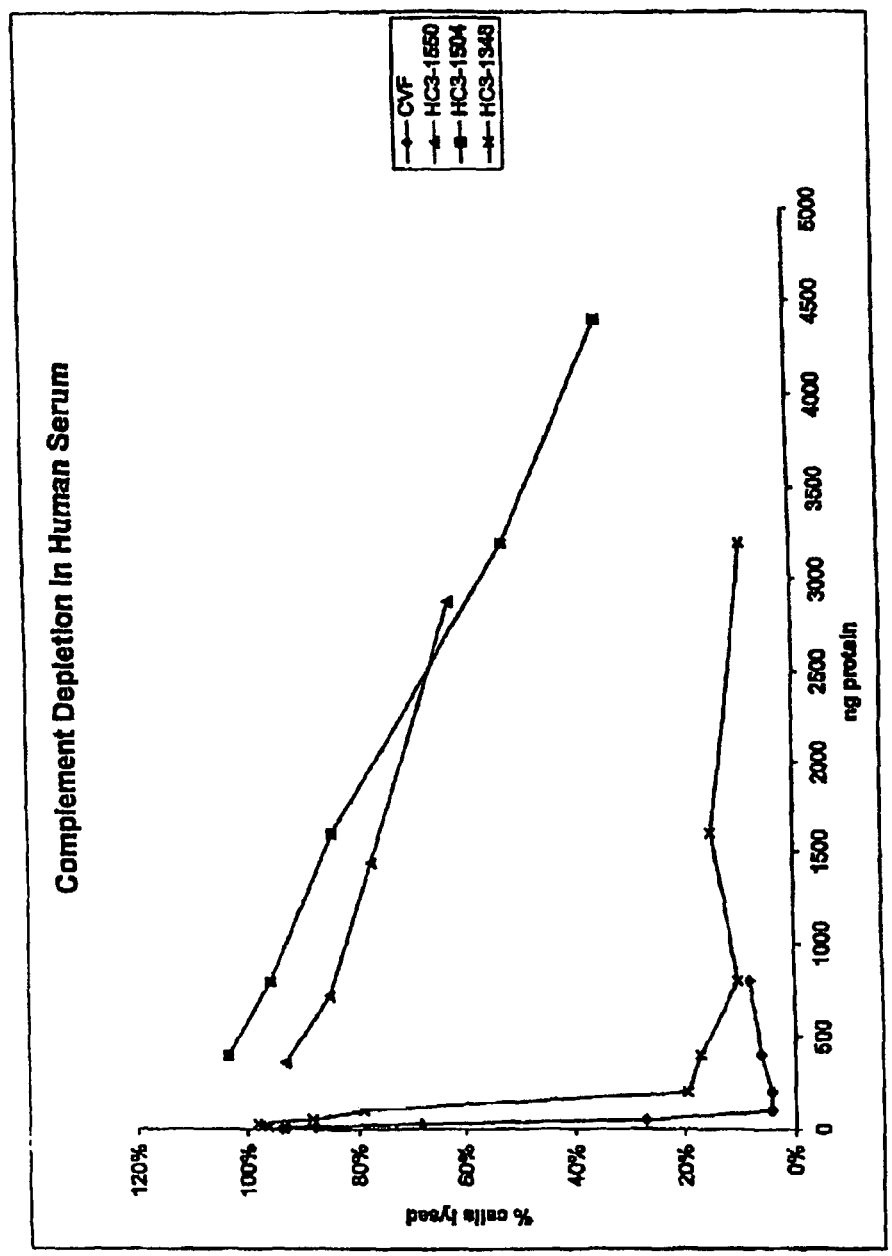
FIG. 4 shows results of a complement depletion assay in human serum of the three modified human C3 proteins (HC3-1348, HC3-1504, and HC3-1550) as compared to CVF.

DETAILED DESCRIPTION OF THE PREFERRED EMBODIMENTS

The replacement of human Complement C3 sequences with CVF sequences representing key structural requirements for CVF specific functions allows the creation of C3 derivatives with CVF-like functions. Preferred embodiments of the invention provide human C3 derivatives that exhibit the CVF-specific function of depleting complement by forming a stable convertase for use as a novel therapeutic agent to deplete complement in clinical situations where complement activation is part of the pathogenesis. Because the structural changes in human C3 caused by CVF-specific sequences are minimal, the modified C3 molecule will exhibit significantly reduced or even absent immunogenicity.

A number of modified human complement C3 proteins (C3) are disclosed that have a substitution of a portion of a human C3 protein, with a corresponding portion of a Cobra Venom Factor protein (CVF) which results in a human C3 protein with CVF functions, but with substantially reduced immunogenicity. The C3 protein may be the pro-protein (a single chain protein) or the cleaved protein by removal of four arginine residues. An additional two chain form may be formed by the removal of the C3a portion. Advantageously, the C3 protein can be manipulated to contain at least one of the following CVF functions: increased ability to form the C3 convertase, increased stability of the C3 convertase, increased resistance to the actions of factors H and/or I, increased activity to cleave C3 and C5, and increased plasma half-life. In one embodiment, the C-terminal portion of the alpha chain of C3 is substituted with a corresponding portion of a CVF protein. A wide variety of specific regions and specific chimerae are disclosed herein. Further, a method of identifying and/or selecting a modified C3 protein is disclosed which involves characterizing the properties of the modified C3 protein to form a function profile of the modified protein, and matching the function profile with a disease or condition to be treated. The function profile may include one or more of the following functions: ability to form a convertase, susceptibility to H and/or I, the ability to cleave C3, the ability to cleave C5, the relative activity of the convertase, the stability of the convertase, and the plasma half-life. The modified C3 protein, also referred to as a chimeric C3 protein, a C3/CVF chimera, or a C3/CVF hybrid protein, can be used to treat a variety of diseases and/or conditions that result from local or systemic complement activation. These diseases include, but are not limited to: reperfusion injury, autoimmune diseases such as rheumatoid arthritis and lupus, and myasthenia gravis and other diseases that result from antibodies that recognize and direct an immune reaction against proteins or structures of the human body.

The Complement System and Disease

The complement system is a component of the vertebrate immune system which is involved in maintaining health through its roles in host defense and immune response. However, complement activation is also involved in the pathogenesis of a multitude of diseases. Examples of these diseases include autoimmune hemolytic anemias, rheumatoid arthritis and other immune complex diseases, and reperfusion injuries in which tissue damage occurs after blood flow has been temporarily suspended. Examples of reperfusion injuries are tissue damage after the reopening of blocked vessels (e.g. heart attack, stroke) and reperfusion with a recipient's blood after organ transplantation. Based on the involvement of the complement system in multiple diseases, including diseases of major prevalence, the last decade has seen the development of multiple anti-complementary agents to interfere with the unwanted complement activation process in these disease states. All of these drug development attempts are based on inhibiting the activation of complement.

Complement Protein C3, Cobra Venom Factor CVF, Similarities and Differences

The third component of complement, C3, plays a pivotal role in both the classical and alternative pathways of complement activation, and many of the physiological C3 activation products have important functions in the immune response and host defense (for review see Müller-Eberhard, H. J. (1988) "Molecular Organization and Function of the Complement System," *Ann. Rev. Biochem.,* 57:321-347, herein incorporated by reference in its entirety). Human C3 is a two-chain glycoprotein with a molecular weight of approximately 185,000. It is synthesized as single-chain pre-pro-C3 which undergoes subsequent processing by removal of four arginine residues between the β- and α-chains. The primary sequence of human C3 is known from molecular cloning. Full or partial sequence information of C3 from other mammalian species as well as non-mammalian species is available including mouse, rat, guinea pig, chicken, cobra, *Xenopus*, and lamprey. The human C3 gene is 42 kb in length and includes 41 exons, ranging in size from 52 to 213 bp.

The major activation product of C3 is C3b. C3b plays a central role in the formation of the alternative pathway C3/C5 convertase. The formation of this enzyme requires initial binding of C3b to Factor B. The weak complex C3b,B is subsequently cleaved by Factor D in the presence of $Mg^{2+}$, resulting in the enzymatically active C3/C5 convertase C3b,Bb and in release of the activation peptide Ba. The C3b,Bb enzyme is very labile, exhibiting spontaneous decay-dissociation into the two subunits C3b and Bb with an intrinsic half life of 1.5 minutes at 37° C. The C3b,Bb enzyme is stabilized by properdin. The C3/C5 convertase cleaves C3 and C5 by hydrolyzing a single peptide bond in the α-chains of the two substrates. In order for the enzyme to cleave C5, C5 has to be bound to another C3b molecule bound to the convertase. In addition to the fast spontaneous decay-dissociation, the C3b,Bb enzyme is subject to stringent control. The enzyme is disassembled by Factor H, and C3b is inactivated by the combined action of factors H and I. In the presence of Factor H, Factor I cleaves the α'-chain of C3b at two cleavage sites. The resulting C3b derivative, called iC3b, can no longer form a convertase with Factor B. Factor I can cleave the α'-chain at a third site, which causes the generation of the two C3 fragments C3c and C3dg. For the third cleavage by Factor I, the C3b receptor, CR1 serves as co-factor.

An unusual structural property of C3 is the presence of an intramolecular thioester in the α-chain. Upon activation of C3 to C3b, the thioester becomes highly reactive and is responsible for the covalent attachment of C3b to cellular and other particular targets. The structural change which accompanies cleavage of the thioester allows the subsequent binding of Factor B and its activation.

The thioester in C3 undergoes slow spontaneous hydrolysis, resulting in the formation of a form of C3 called iC3 or $C3(H_2O)$. iC3 assumes C3b-like functions and can form a fluid-phase convertase with Factors B and D in serum. The resulting convertase iC3,Bb is similarly labile as the C3b,Bb convertase and subject to control by factors H and I. However, spontaneous hydrolysis of the thioester and the ensuing low grade activation of C3 by the iC3,Bb convertase is believed to be responsible for the initial deposition of C3b on target cells or particles, leading to activation of the alternative pathway on so-called activator surfaces.

C3 is a highly unusual multi-functional protein. The protein including its various activation products specifically interacts with approximately twenty different plasma proteins or cell surface receptors. This multifunctionality has spurred significant interest in a detailed structure/function analysis of the molecule. For some ligands of C3, including Factor H, properdin, Factor B, and the complement receptors CR1, CR2, CR3, and C3a receptor binding sites have been proposed or assigned to more or less defined regions of the C3 polypeptide.

Cobra venom contains a structural and functional analog of C3 called cobra venom factor (CVF). Functionally, CVF resembles C3b in that it can bind Factor B in human serum and virtually all vertebrate sera to form a weak complex CVF,B, which is subsequently cleaved by Factor D in the presence of $Mg^{2+}$ into the bimolecular enzyme CVF,Bb and Ba. The bimolecular complex CVF,Bb is a C3/C5 convertase that activates C3 and C5 analogously to the C3/C5 convertase formed with C3b.

CVF is a three-chain glycoprotein with a molecular mass of approximately 150,000 Da. CVF and mammalian C3 have been shown to exhibit several structural similarities including immunological cross-reactivity, amino acid composition, circular dichroism spectra and secondary structure, and electron microscopic ultrastructure. Initial N-terminal amino acid sequence comparisons have demonstrated sequence homology with C3 and have led to the suggestion that CVF structurally resembles C3c. The structural homology between CVF and C3 and the chain relationships were confirmed by the molecular cloning of CVF, which revealed an overall similarity at the protein level of approximately 70 percent to mammalian C3s and over 90 percent when compared to cobra C3.

Despite these functional and structural similarities between CVF and C3, the two molecules and the resulting convertases exhibit important functional differences:

1. Both enzymes exhibit spontaneous decay-dissociation into the respective subunits which abolishes the enzymatic activity. Whereas the C3b,Bb enzyme is very short-lived and decays with an intrinsic half-life of 1.5 minutes at 37° C., the CVF,Bb enzyme is orders of magnitude more stable, decaying with an intrinsic half-life of approximately seven hours.
2. The C3b,Bb enzyme is subject to regulation by factors H and I. In contrast, CVF,Bb and CVF are completely resistant to the regulatory actions of these two proteins.
3. The C3b,Bb enzyme generated during complement activation is surface bound. In contrast, the CVF,Bb enzyme is a fluid-phase enzyme (like iC3,Bb).
4. Another functional difference between C3b,Bb and CVF,Bb lies in the C5 convertase activities. In order for C5 to be cleaved by a C5 convertase, it needs to be bound to either C3b or CVF. However, for C5 cleavage to occur by the C3b,Bb enzyme, C5 has to be bound to a different C3b molecule than the one that is part of the C3b,Bb enzyme. In contrast, C5 is bound by the same CVF molecule that carries the Bb catalytic subunit. This property of the CVF,Bb enzyme to bind C5 is probably the reason for its ability to exhibit fluid phase C5 convertase activity, whereas the C5 convertase activity of the C3b,Bb enzyme is confined to the surface of a particle.
5. Both enzymes have been shown to differ somewhat in their kinetics of C3 hydrolysis. Based on the $k_{cat}/K_m$, the catalytic efficiency is approximately eight-fold greater for C3b,Bb compared to CVF,Bb.

In terms of functional consequences, the two most significant differences between CVF,Bb and C3b,Bb are the intrinsic stability of the CVF,Bb enzyme and its resistance to the regulatory proteins factors H and I. Once the CVF,Bb enzyme has formed, it will continue to activate C3 and C5, leading to complement consumption. Ever since it was demonstrated over 30 years ago that CVF can be administered safely to laboratory animals in order to deplete their plasma complement, CVF has become an important investigational tool to study the various biological functions of complement in immune response, host defense, and pathogenesis of disease by comparing normal (complement-sufficient) animals with CVF-treated (complement-depleted) animals.

C3/CVF Derivatives

CVF is a complement inhibitor that acts through a mechanism of exhaustive activation which subsequently leads to depletion. As a matter of fact, CVF is frequently used as the standard to evaluate the anti-complement activity of other drugs. Whereas CVF exhibits this powerful anti-complement activity, it is not suitable for human application because of its immunogenicity. For this reason it is desirable to prepare a substantially non-immunogenic CVF by taking advantage of the extensive structural similarity between CVF and C3, and to generate human C3 derivatives with the desired complement-depleting function of CVF by substituting the functionally important regions of the CVF molecule into human C3 by recombinant means. This has been accomplished as described herein.

A number of human C3 derivatives have been produced and/or designed, in which portions of the C3 sequence were replaced with homologous CVF sequences, mainly sequences in the CVF beta chain. CVF and C3 have been successfully expressed by recombinant means in eukaryotic expression systems. The alpha chain region of C3, and preferably the C-terminal portion of this chain, was chosen based on previous work in which five hybrid proteins were constructed between CVF and cobra C3 (because of its greater similarity to CVF than human C3), collectively spanning the entire CVF sequence (*Mol. Immunol.* 40:199 (2003), incorporated herein by reference in its entirety). The other line of work involved the limited proteolysis of the CVF protein (*Mol. Immunol.* 30, Suppl. 1, 113 (1993) U.S. Pat. No. 5,174,344, incorporated herein by reference in its entirety). Using the results of this previous work, three human C3 preferred derivatives were created by replacing amino acid residues 1550-1663, 1504-1663, and 1348-1663, respectively, with the homologous sequences from CVF. The C3 derivatives are designated by the first amino acid residue and if the last amino acid residue is not indicated, it is understood to be 1663. If the endpoint of the CVF insertion is before the C-terminus of the protein, it is designated with the location (for example: HC3-1550/1617). The C3 derivative which was created by replacing amino acids residues 1348-1663 was formerly referred to as 1325-1663, but substitution mapping has subsequently shown that the substitution was at 1348 rather than 1325. The three human C3 derivatives are referred to as HC3-1550, HC3-1504, and HC3-1348. The three human C3 derivatives were shown to exhibit the desired CVF activity: all three proteins are able to form an active C3/C5 convertase. This is demonstrated by the ability of the three proteins to support the activation of factor B, and by the ability of the three resulting convertases to cleave C3. All three proteins form stable convertases, although the intrinsic stability and at least one (HC3-1550) exhibits a lower intrinsic stability compared to CVF. Unexpected was the observation that two of the three proteins first tested (HC3-1550 and HC3-1348) were actually able to decomplement guinea pig serum, although this activity was clearly less than that of CVF, and four of five proteins were able to deplete complement in human serum, with HC3-1348 and HC3-1496 able to decomplement human sera almost as well as CVF. HC3-1550/1617 was not able to deplete complement in human serum. The ability to at least partially deplete complement indicates that the C3 derivative does not only form a stable convertase but is at least partially resistant to the regulatory proteins factors H and/or I, thereby exhibiting CVF-like activity. The human C3 derivative HC3-1550 differs from human C3 in less than 4% of the amino acid residues, which greatly reduces or eliminates its predicted immunogenicity compared to CVF. Various C3 hybrids can be preferred, based upon their various characteristics, depending upon the disease to be treated. For example, for the treatment of chronic diseases, the objective is to provide a C3 hybrid having extremely low or no immunogenicity and high convertase stability, facilitating its persistence in the body of the patient suffering from the chronic disease. In such a situation, the other characteristics, such as the activity of the convertase, are of comparatively less importance. In contrast, for treatment to avoid complement-associated reperfusion injury, a high convertase activity is of greater importance than convertase stability. Thus, a multiplicity of different hybrids, each having a particular array of properties, permits selection of a preferred hybrid for treatment of a given condition that can be treated by complement activation and/or complement depletion.

In one embodiment, the present invention relates to modified complement C3 proteins that exhibit at least one of the following CVF or CVF,Bb qualities: decaying with an intrinsic half-life of longer than 1.5 minutes, increased resistance to the regulatory actions of factors H and/or I, fluid-phase C3 convertase and fluid-phase C5 convertase activity. In addition to these factors, in some embodiments the catalytic efficiency may be reduced relative to C3b,Bb, since the catalytic efficiency is approximately eight-fold greater for C3b,Bb compared to CVF,Bb. In other embodiments the catalytic efficiency is not reduced or is elevated in comparison to C3b,Bb. Although many preferred C3 hybrids have little or no immunogenicity, other embodiments, which are nevertheless suitable for many applications, may display detectable to moderate immunogenicity in some cases.

In some embodiments, the intrinsic half-life of the convertase formed with the modified C3 protein is greater than 1.5 minutes, preferably greater than 10 minutes. In further embodiments, the intrinsic half-life can fall generally between that of the CVF-containing convertase (7 hours or longer) and that of C3 (1.5 minutes), including but not limited to about: 2 minutes, 10 minutes, 20 minutes, 30 minutes, 40 minutes, 50 minutes, 60 minutes, 90 minutes, 2 hours, 2.5 hours, 3 hours, 3.5 hours, 4 hours, 4.5 hours, 5 hours, 5.5 hours, 6 hours, 6.5 hours and 7 hours, or more. Modified C3 proteins with short convertase intrinsic half-lives and/or short plasma half-lives will be useful for some applications, while C3 proteins with long convertase intrinsic half-lives and/or long plasma half-lives will be useful for different applications.

In further embodiments, the resistance of the C3 hybrid to factors H and/or I is greater than that for the unmodified C3 and is in some embodiments as good as the resistance of CVF. However, in some embodiments, further modification in other parts of the molecule can be necessary to achieve resistance to factors H and/or I.

While many embodiments described herein are directed to specific substitutions of one or more discrete regions of C3 with corresponding regions of CVF, other embodiments include substitutions employing a sequence that is substantially related, but not identical, to a CVF sequence. That is, there are positions within a CVF region selected for substitution, in which changes to one or more amino acids can be made without a loss of any desirable feature or function of the selected CVF region, and in some cases such changes can confer an enhanced feature or function. All such changes are considered to be embodiments of the invention.

In a further embodiment, the catalytic activity of convertase containing the modified C3 protein is in some embodiments at least 50% that of the convertase containing CVF, and may be greater than that of the convertase containing unmodified C3. In a further embodiment, the catalytic activity is 60%, 70%, 80% 90% or 100% that of the CVF convertase. Both enzymes have been shown to differ somewhat in their kinetics of C3 hydrolysis. Thus, in many embodiments, convertases containing the modified C3 can have a catalytic activity that falls between the two, or that exceeds the activity of the convertase containing unmodified C3. Thus, in some embodiments, such activity of the convertase containing the modified C3 can be from 10% to 1000%, or more, that of the convertase containing CVF, including but not limited to 20%, 30%, 40%, 50%, 60%, 70%, 80%, 90%, and 110%, 135%, 150%, 200%, 300%, 400%, 500%, 750%, 1000% and more.

Based on the $k_{cat}/K_m$, the catalytic efficiency is approximately eight-fold greater for C3b,Bb compared to CVF,Bb when cleaving C3. Thus, in some embodiments, the catalytic efficiency of convertase containing the modified C3 protein is in some embodiments at least 50% that of the convertase containing CVF, and may be greater than that of the convertase containing unmodified C3b. Both enzymes have been shown to differ somewhat in their kinetics of C3 hydrolysis. Thus, in many embodiments, convertases containing the modified C3 can have a catalytic efficiency that falls between the two, or that exceeds the efficiency of the convertase containing unmodified C3. Thus, in some embodiments, such efficiency of the convertase containing the modified C3 can be from 10% to 1000%, or more, that of the convertase containing CVF, including but not limited to 20%, 30%, 40%, 50%, 60%, 70%, 80%, 90%, and 110%, 135%, 150%, 200%, 300%, 400%, 500%, 750%, 1000% and more.

In further embodiments, the C5 cleaving activity of the modified C3 proteins is increased. The C5 cleaving activity can be from about 10% to 400% of the activity of CVF or C3, including but not limited to: 15%, 20%, 25%, 30%, 35%, 40%, 45%, 50%, 55%, 60%, 65%, 70%, 75%, 80%, 85%, 90%, 95%, 99%, 100%, 150%, 200%, 250%, 300%, 350%, and 375%.

In further embodiments, the binding of the modified C3 proteins to Factor B and/or its subsequent cleavage by factor D may be reduced. However, as long as at least a functional amount of the catalytic activity and the complement depleting activity remain, the modified C3 protein is useful.

In further embodiments, convertases having the modified C3 proteins exhibit substantially the same complement-activating activity of those containing natural CVF. By the term "exhibit substantially the same complement-activating activity of natural CVF it is meant that the C3 derivatives of the present invention have from 0.1 to 97%, preferably from 50 to 97%, preferable from 80 to 97% of the level of the complement activating activity of natural CVF as measured by the method of Cochran et al. ((1970) J. Immunol. 105(1)), 55-69, herein incorporated by reference in its entirety).

In some embodiments, the modified complement C3 proteins are C3 molecules in which some or all of the C-terminal region has been replaced with the corresponding region of CVF. In some embodiments, only the C-terminal portion of the alpha chain of C3 is replaced with the corresponding region of CVF. In some embodiments some or all of amino acids 700-1663 are replaced, including but not limited to regions of from 20 to about 1000 amino acids, including but not limited to: 30, 40, 50, 60, 70, 80, 90, 100, 110, 120, 130, 150, 175, 180, 190, 200, 250, 275, 300, 350, 375, 400, 450, 475, 500, 550, 575, 600, 650, 675, 700, 750, 775, 800, 850, 875, 900, 950 975, 1000. In some embodiments, the beta chain of C3 is intact, that is, is the same as in natural C3. However, in some embodiments, in addition to the substitutions in the alpha chain of C3, other substitutions can be made to provide such functions as increased stability (for example, the sites which relate to Factor H binding and Factor I cleavage can be mutated or substituted). Specific substitutions include but are not limited to amino acids 1550-1663, 1504-1663, 1348-1663, 1550-1617, 1504-1617, 1470-1663, 1348-1617, 1470-1617, 1264-1324, 1348-1386, 749-784, 874-921, 1496-1663, 1496-1617 and 936-970. In some embodiments, still smaller substitutions in these areas can correspond to smaller regions that result in a C3 with the desired CVF functions or qualities.

The immunogenicity of preferred embodiments remains low or absent—comparable to that of C3. In some embodiments, the modified C3 protein is substantially non-immunogenic. Substantially non-immunogenic means that the protein can still exhibit complement activating function when injected into a human patient. Further, the modified C3 protein may be as non-immunogenic as C3 or may be from about 75% non-immunogenic to about 100% non-immunogenic, including but not limited to 80%, 85%, 90%, 95%, and 99%.

Methods of Treatment Systemically and Locally

The modified human complement C3 proteins produced by the methods disclosed herein can be used to deplete complement locally or systemically as follows:

Local treatment may be effected in a number of ways to produce a result of depletion of complement or activation of complement, depending on the desired effect. In one embodiment, local depletion is effected when the modified C3 proteins are administered locally to an organ, tissue, cavity, or intradermally. This results in a temporary and complete depletion of complement in the area. Local depletion or activation may also be effected using an insulin-type pump that produces an intermittent or constant flow of the modified C3 protein to a selected site. Alternatively, local activation of complement may employ a specific monoclonal antibody which, when chemically attached to the modified C3, can localize it to a specific tissue, a disease, or an infected cell to cause continuous activation of complement in that area. In other embodiments, the antibody can be attached to the modified C3 protein via recombinant DNA technology.

Systemic depletion is effected when the modified C3 proteins are administered systemically, for example, intravenously or intraperitoneally. This results in a temporary and complete depletion of complement systemically. This method can be used for reperfusion injury, coronary heart surgery, transplantation and or systemic disease, particularly during a flare-up or episodical activity. This is further discussed in the Examples provided herein.

Many of the most advantageous qualities of the modified human C3 proteins used in each of these cases and in specific disease states can vary considerably. For example, in those cases when an immediate, but temporary removal of complement is desired, a modified protein which has a shorter plasma half-life and/or stability, but high complement activation activity (high C3/C5 convertase activity) would be most suited. In the case where a chronic disease is being treated, a long plasma half-life and/or stability and a low or sluggish activity would be most suitable.

Convertase Activities/Functions

When producing and analyzing the best use for the modified C3 proteins herein, a number of functions and activities can be used for such an analysis, including but not limited to the following:

Affinity for Factor B—Differences in how efficiently the modified C3 proteins support the activation of factor B (cleavage into Ba and Bb) can be detected and taken advantage of. There are multiple factors beyond just affinity for factor B that go into supporting factor B activation, but once the convertase is formed, the subsequent key properties that are generally most important are stability, regulation by H and I, and activity of cleaving C3 and C5.

Stability—Both the C3b,Bb and CVF,Bb enzymes exhibit spontaneous decay-dissociation into the respective subunits which abolishes the enzymatic activity. Whereas the C3b,Bb enzyme is very short-lived and decays with an intrinsic half-life of 1.5 minutes at 37° C., the CVF,Bb enzyme is orders of magnitude more stable, decaying with an intrinsic half-life of approximately seven hours.

Regulation by Factors H and/or I—The C3b,Bb enzyme is subject to regulation by factors H and I. In contrast, CVF,Bb and CVF are completely resistant to the regulatory actions of these two proteins.

Activity of Cleaving C3—Both enzymes have been shown to differ somewhat in their kinetics of C3 hydrolysis. Based on the $k_{cat}/K_m$, the catalytic efficiency is approximately eightfold greater for C3b,Bb compared to CVF,Bb.

Immunogenicity—Because the structural changes in human C3 caused by CVF-specific sequences are minimal, modified C3 can exhibit significantly reduced or even absent immunogenicity as compared with CVF. In addition, as is typical in species far removed from human, a transferase enzyme is produced in cobras that transfers an alpha-bonded galactose to the end of CVF oligosaccharide chains. Because humans do not produce this transferase, the alpha bonded galactose residues are seen as non-self and are highly immunogenic. Thus, anti-alpha-gal antibodies are produced that recognize the specific CHO moieties produced on CVF. Human C3 and CVF lack identity at 52% of their positions, and carbohydrate differences are even more pronounced. Thus, because preferred modified C3 proteins have less than 10%, and in some embodiments about 4%, of the C3 amino acids replaced with those of CVF, and also have no cobra-derived carbohydrate structures (specifically alpha-bonded galactoses on the glycans), the C3 hybrids of the invention are significantly less immunogenic. In some embodiments, the C3 hybrids of the preferred embodiments are significantly less immunogenic than CVF. In other embodiments, the C3 hybrids of the preferred embodiments are at least 50% less immunogenic than CVF. In some embodiments, the recombinant proteins are produced in either insect or mammalian cell lines, which will result in carbohydrate moieties that are either simple or very similar to what would be found in humans.

EXAMPLES

Five CVF/cobra C3 loss-of-function hybrid proteins were produced in which large portions of the CVF sequence were replaced by homologous portions of cobra C3. Preliminary characterization of these hybrid proteins showed that substitutions in the α-chain of CVF (β-chain of C3) with cobra C3 sequences did not appear to change the functional property of depleting serum complement activity, whereas replacing portions of the β- and γ-chains had a major effect. Hybrid proteins H4 and H5, in which CVF residues 978 through 1642 were replaced by cobra C3 sequence, exhibited a significant reduction in bystander lysis (a measure for C5 cleavage) activity in addition to the impaired ability to deplete serum complement. This suggested that the alpha chain of C3 (corresponding to the β- and γ-chains of CVF) may be a major site for the differences between the activity of CVF and C3. Another line of experimental support strongly suggests the C-terminal portion of the CVF α-chain is important for CVF function comes from the experiments of limited proteolysis of CVF with chymotrypsin (Grunwald, et al. (1993) Mol. Immunol. 30, Supp. 1, 30, herein incorporated by reference in its entirety). Thus, a large number of modified human complement C3 proteins (C3) have been produce or identified that have a substitution of a portion of the human C3 protein, with a corresponding portion of the Cobra Venom Factor protein (CVF). These substitutions result in a human C3 protein with CVF-type functions, but with substantially less immunogenicity than CVF. The production and testing of these proteins is set forth below in Examples 1-3. Various uses and assays for these proteins are provided in Examples 4-10.

Example 1

Production of Human Complement C3/CVF Hybrid Proteins

The replacement of human C3 sequences with CVF sequences representing important structural features for CVF specific functions allows the creation of C3 derivatives with CVF-like functions. Thus, embodiments of the invention are directed to generation of human C3 derivatives that exhibit the CVF-specific function of depleting complement by forming a stable convertase for use as a novel therapeutic agent to deplete complement in clinical situations where complement activation is part of the pathogenesis. Because the structural changes in human C3 caused by CVF-specific sequences are minimal, it is clear that the modified C3 molecules can exhibit significantly reduced or event absent immunogenicity.

The human C3 molecules in Table 1 are engineered to contain specific CVF sequences so as to create human C3 derivatives with CVF functions. Some embodiments of the invention provide smaller substitutions in these areas, to define small regions that result in modified C3 proteins that can form a relatively stable convertase and that exhibit little or no immunogenicity.

TABLE 1

| Exemplary Human C3/CVF clones | | |
|---|---|---|
| HC3-1550 | HC3-1504 | HC3-1348 |
| HC3-1550/1617 | HC3-1504/1617 | HC3-1470 |
| HC3-1348/1617 | HC3-1470/1617 | HC3-1264/1324 |
| HG3-1348/1386 | HC3-749/784 | HC3-874/921 |
| HC3-936/970 | HC3-1496 | HC3-1496/1617 |
| HC3-994 | HC3-994/1617 | HC3-1617 |

Certain modified C3 proteins (also called hybrid proteins or chimerae) were produced by site-directed mutagenesis as described below. Briefly, for site-directed mutagenesis replacing small portions of human C3 sequence with CVF, the procedure of Ho et al. was used (Ho, S. N., Hunt, H. D., Horton, R. M., Pullen, J. K. and Pease, L. R. (1989) "Site-Directed Mutagenesis by Overlap Extension Using the Polymerase Chain Reaction" Gene, 77:51-59, herein incorporated by reference in its entirety). In this method, two PCR reactions were performed, one with a forward primer somewhere upstream from the site of the desired mutation. The second, reverse primer contained the mutation. The second PCR of this round had a forward primer containing the desired mutation, with the reverse primer being downstream from the mutation site. At least one unique restriction site is preferably present in each of the PCR products from this step so that it is possible to transfer the modified DNA back into the original clone. Amplification was done using a large amount of template DNA, and a low number of cycles to minimize mutations introduced by the PCR process. More specifically, the first round of PCR, the reaction for the 5' product used a human C3 plasmid as the template, while the other PCR used a CVF plasmid. In this case the middle, "mutagenesis" primers partially consisted of C3 sequences and partially of CVF sequences, providing a "bridge" between the two sequences.

After amplification, the two products were purified by gel electrophoresis and isolated from the gel using a Qiaquick Gel extraction kit from Qiagen. Then, the fragments were combined, and another PCR reaction done, using the two fragments as the template, and the outside primers as the amplification primers. Again, the PCR reaction was performed using a high concentration of template DNA and only cycled for a few cycles to minimize PCR-caused mutations. The resulting PCR product was cut with the two unique restriction enzymes, size purified on an agarose gel, and the fragment of interest isolated using the Qiaquick column. The fragments were then cut with the appropriate enzymes, and cloned into either pBS-HuC3 or pHC3-1550(-sig) that had been cut with the same enzymes.

The first hybrid plasmid, pHC3-1550 contained CVF sequences replacing the homologous C3 sequences from position 1550 to the C-terminus of the protein. The second hybrid plasmid, pHC3-1504, codes for a hybrid protein containing CVF sequences replacing human C3 sequences from position 1504 to the C-terminus of the protein. The third hybrid plasmid, pHC3-1348, contained CVF sequences replacing the homologous C3 sequences from position 1348 to the C terminus of the protein. To prepare the first plasmid, two initial PCR reactions were performed. Both hybrids had about 19 amino acid vector-coded sequence having some or all of the following RSPWPGVPTSPVWWNSADA (SEQ ID NO:5). Because of the method of cloning of the C3 gene, these amino acids coded for by the cloning vector, were N-terminal to the N-terminus of human C3. These extra amino acids did not affect the activity of the protein, so they could be removed with no ill effect. The first plasmid was prepared using pBS-HuC3-2 as a template, and using the following oligonucleotides as primers: HC3H5-1 (GGATGC-CACTATGTCTATATTGGACATATCC—SEQ ID NO:6), and HC3H5-2 (TCTTCTATTCGAACCAGTCGGGTCT-TGTAC—SEQ ID NO:7). The second PCR used pCVF-FL3Δ as a template, and the following oligonucleotides as primers: HuC3H5-3 (GTACAAGACCCGACTGGTTC-GAATAGAAGAACAAG—SEQ ID NO:8) and HuC3H54 (TATCATGTAAGCGGCCGCGTATAAA-CAATTTAAGGG—SEQ ID NO:9). Both reactions were performed in an Eppendorf thermocycler, using the following program: 95° C. for 5 min., followed by five cycles of 95° C. for 30 sec., 58° C. for 30 sec. (gradient from 50 to 65° C.), and 72° C. for 1 min., followed by 20 cycles of 95° C. for 30 sec., 57.5° C. for 30 sec. (gradient from 55 to 60° C.), 72° C. for 1 min, followed by 72° C. for 10 min. The two fragments were purified using a Qiagen PCR cleanup kit, and joined in a second PCR reaction, using HC3H5-1 and HC3H5-2 as primers, and the two primary PCR products as template. The cycling conditions used for this reaction were: 95° C. for 5 min, followed by 5 cycles of; 95° C. for 30 sec., 51° C. for 30 sec (gradient from 46 to 56° C.), and 72° C. for 1.5 min, followed by 20 cycles of; 95° C. for 30 sec., 57° C. for 30 sec (Gradient from 52 to 62° C.), and 72° C. for 1.5 min. This was followed by a 10 min incubation at 72° C. The PCR fragment was purified as described above, cut with BsrGI and NotI, gel purified, and isolated using a Qiagen Gel Isolation kit. This fragment was cloned into pBS-HuC3-2 that had been cut with the same enzymes, and the resulting clones were screened for insertion of the correct fragment by digestion with EcoRI. All clones with the correct EcoRI digestion pattern were sequenced to ascertain that no PCR-induced mutations were inserted. A large-scale preparation of one clone (pHC3-1550) with the expected sequence was performed, and the insert excised by digestion with HindIII (and end repaired with T4 DNA polymerase) and NotI. The fragment was purified by gel electrophoresis, isolated from the gel as described above, and cloned into the *Drosophila* expression vector, pMT/V5-HisA that had been cut with EcoRV and NotI. Attempts to obtain expression of hybrid proteins from this construct resulted in very low yields of protein. For this reason, a construct was made having the human C3 signal sequence removed from pHC3-1550, while inserting a new, unique AfeI site. To do this, pHC3-1550 was amplified with the following two primers: HC3SigRemF; AGATCTCCATGGAAGCT-TAGCGCTGGGAGTCCCATGTACTCTATCATC (SEQ ID NO:10, and HC3SigRemR: GCGTCCCGCCTTCAA-CAGCC (SEQ ID NO:11). After amplification, the fragment was purified as described above, cut with HindIII and SpeI. The 150 bp band was gel isolated, and cloned into pHC3-1550 that had been cut with the same enzymes. DNA from transformants was screened by cutting with AfeI, and all positive clones were confirmed by DNA sequencing. This plasmid was called pHC3-1550(-sig).

The insert was excised from the plasmid by digestion with AfeI, DraI (to fragment the plasmid), and NotI. The digest was run on a gel, and the 5 kb fragment isolated as described above. It was then ligated into pMT-Bip/V5-HisA that had been digested with EcoRV and NotI. The resulting plasmid was called pMB/HC3-1550.

The plasmid for the production of the second hybrid protein, HC3-1504, was produced in a similar manner, as follows. Two PCR reactions were performed to obtain the human C3 and CVF portions of the coding sequence. In the first, pBS-HuC3-2 was used as a template, with the following oligonucleotides used as primers: HC3H5-3-F1 (TCTGT-GTGGCAGACCCCTTCGAGG—SEQ ID NO:12) and HC3H5-3-R1 (CGTTACCAATACATATCTTGT-TCAGCTTTCCATCC—SEQ ID NO:13). The second PCR used pCVF-FL3Δ as a template, and the following oligonucleotides as primers: HuCC3H5-3-F2 (GGATG-GAAAGCTGAACAAGATATGTATTGGTAACG—SEQ ID NO:14), and HuC3H5-3-R2 (CATCCATGACATA-GATATCATTACCATCTTG—SEQ ID NO:15). The resulting two PCR products were joined in a PCR reaction, using HuC3H5-3-F1 and HuC3H5-3-R2 as primers, and the two PCR fragments as the template. After the second PCR reaction, the product was purified using a Qiagen PCR cleanup kit, it was then cut with NspV, and cloned into pHC3-1550(-sig) that had been cut with the same enzyme and that had also been treated with Calf intestine alkaline phosphate. Resulting clones were cut with EcoRI to determine the orientation of the insert and sequenced to ascertain that no PCR induced modifications were present. The resulting plasmid was called pHC3-1504. The insert from this plasmid was then isolated as described above, and cloned into pMT-Bip/V5-HisA as described above. This plasmid was called pMB/HC3-1504.

The plasmid for the production of the third construct, HC3-1348, was constructed in a similar manner to that used for HC3-1504. The only difference is that the two mutation primers were HuC3H5-5-1R (GCAACTGTGCGTTATACAT-TGTCACCACCGAC—SEQ ID NO:16) and HuC3H5-5-2F (GTCGGTGGTGACAATGTATAACGCACAGTTGC—SEQ ID NO:17). For the primary PCR reactions, the primers used were HuC3H5-3-1F and HuC3H5-5-1R, and the template was pBS-HuC3-2, while the primers used for the second primary PCR reaction were HuC3H5-5-2F and HuC3H5-3-2R, using pCVF-FL3Δ as the template. After the primary PCR, the two fragments were purified and used as templates for the secondary PCR reaction as described for the construction of pHC3-1504. The secondary PCR reaction product was purified, cut with NspV, and cloned into pHC3-1550, the sequence confirmed and the insert cloned into pMT-Bip/V5-HisA) as described above.

The plasmid for the production of the fourth hybrid protein, HC3-1496, was produced in a similar manner, as follows. Two PCR reactions were performed to obtain the human C3 and CVF portions of the coding sequence. In the first, pBS-HuC3-2 was used as a template, with the following oligonucleotides used as primers: HC3H5-3-F1 (TCTGTGTG-GCAGACCCCTTCGAGG—SEQ ID NO:12) and HC3H5-4-R1 GAGAAGGCCTGTTCCTTTATCCGGATGG-TAGAACCGGGTAC (SEQ ID NO:18) and. The second PCR used pCVF-FL3Δ as a template, and the following oligonucleotides as primers: HuCC3H5-4-F2 CCGGTTCTAC-CATCCGGATAAAGGAACAGGCCTTC (SEQ ID NO:19), and HuC3H5-3-R2 (CATCCATGACATAGATATCATTAC-CATCTTG—SEQ ID NO:20). The resulting two PCR products were joined in a PCR reaction, using HuC3H5-3-F1 and HuC3H5-3-R2 as primers, and the two PCR fragments as the template. After the second PCR reaction, the product was purified using a Qiagen PCR cleanup kit. It was then cut with NspV, and cloned into pHC3-1550(-sig) that had been cut with the same enzyme and been Calf intestine alkaline phosphate treated. The resulting plasmid was called pHC3-1496. The insert from this plasmid was then isolated as described above, and cloned into pMT-Bip/V5-HisA as described above. This plasmid was called pMB/HC3-1496.

The plasmid for the production of the fifth hybrid protein, HC3-1550/1617, in which the C-terminal 46 amino acid residues of HC3-1550 are replaced with human C3 sequences, is described below. Again, two PCR reactions were done to obtain the CVF and human C3 portions of the coding sequence. In the first, pHC3-1550 was amplified, using the following two primers; HuC3H5-F1 GGATGCCACTAT-GTCTATATTGGACATATCC (SEQ ID NO:21), and HuC3H5-2R1, CCCGATGATGTAGCTGAGTT-TATCTTTCGTGGG (SEQ ID NO:22). The second PCR was performed using pCVF-FL3Δ as the template, and HuC3H5-2F2 (CCCACGAAAGATAAACTCAGCTACAT-CATCGGG—SEQ ID NO:23) and HuC3H5-2-R2 (AATTG-GAGCTCCACCGCGGTGG—SEQ ID NO:24) as the primers. After the first PCR, the fragments were joined in a second PCR reaction, using HuC3H5-F1 and HuC3H5-2-R2 as the primers, and the two PCR fragments as the template. Following this PCR, the amplified fragment was purified using Qiagen PCR purification columns, cut with BsrGI and NotI, and cloned into pHC3-1550(-sig) that had been cut with the same enzymes. The resulting plasmid was sequenced to ascertain the correct sequence. It was called pHC3-1550/1617. The insert was isolated as described above and cloned into pMT-Bip/V5-HisA as described above. This plasmid was called pMB/HC3-1550/1617.

In some cases, portions of the human C3 are additionally exchanged with CVF sequence at more than one site to generate a modified C3 that is useful for one or more of the purposes presented herein. Thus, modified C3 proteins are generated wherein CVF-specific sequence is inserted in more than one region, or known regions are mutagenized by various means. For example, in addition to a site or sites required for the formation of a physically stable convertase with factor B, it can also be desirable to change a Factor I cleavage site in human C3. Factor I-resistant mutants of human C3 have been successfully described previously by Fecke, et al., 1998 (Fecke, W., Farries, T. C., D'Cruz, L. G., Napper, C. M., and Harrison, R. A. (1998) *Xenotransplantation* 5:29-34, herein incorporated by reference in its entirety). For example, replacement of select sequences required for specific CVF functions allows one to engineer novel C3 derivatives wherein specific subsets of CVF functions are present or eliminated, respectively (e.g. a C3 derivative or CVF derivative that forms a stable C3 convertase but does not cleave C5). A modified C3 molecule that does not activate C5 may have particular advantage for therapy as it prevents the generation of the pro-inflammatory C5a anaphylatoxin.

Example 2

Expression of Modified human C3 Proteins

The proteins were produced in the *Drosophila* S2 cell system, using the *Drosophila* Bip signal sequence for secretion of the proteins. Briefly, the plasmids pMB/HC3-1550, pMB/HC3-1504, pMB/HC3-1496, pMB/HC3-1550/1617, and pMB/HC3-1348 were transfected into *Drosophila* S2 cells using the calcium phosphate method of Chen and Okayama (Chen, C., and Okayama, H. (1987) Mol. Cell. Biol. 7(8), 2745-2752, herein incorporated by reference in its entirety). S2 cells were transfected with a mixture of expression plasmid and pCoBlast, using a ratio of 19:1 (w:w). Following transfection, cells containing both plasmids were selected using blasticidin (25 μg/ml). For expression, 1-liter cultures of transfected cells were grown in serum-free medium (Hi-Five plus L-glutamine), in the absence of blasticidin. When the cells reached a density of $5\times10^6$ cells/ml., production of the recombinant proteins was induced by the addition of $CuSO_4$ to a final concentration of 25 μM. Cultures were allowed to express recombinant proteins for 4-5 days. Hybrid proteins were then purified from the media by a combination of ANX, Sephacryl H-300, and CM-FF chromatography.

Because of the method of cloning of the C3 gene, there are several amino acids (approximately 19) coded for by the cloning vector, that are N-terminal to the N-terminus of human C3. These extra amino acids do not affect the activity of the protein, so they can be removed with no ill effect. In some cases, it can be preferred for there to be at least two amino acids that are an artifact of the restriction sites needed to clone the final construct into the expression vector. In various embodiments, a variety of signal sequences can be used, including the native signal sequence of human C3, as well as any other signal sequence effective in directing entry of the nascent polypeptide into the endoplasmic reticulum.

Other expression systems that can be used, include but are not limited to: Baculovirus infection of Sf9 or HiFive cells (other insect expression systems), CHO cells, COS-7 cells (mammalian expression systems), *E. Coli*, BHK, HEK293 cells, and various yeast expression systems, including the *Hanselula* yeast expression system.

Example 3

Results of the Activity Measurements of the Modified Human Complement C3 Proteins The purified modified human C3 protein hybrids were subjected to a number of functional analyses as follows.

Complement Depletion:

This assay measures the ability of a protein to deplete complement in human (or other) serum. The assay was done in two steps. In the first step, the protein of interest was diluted to the desired concentrations in buffer, usually by serial dilution (typically from less than a nanogram/microliter up to approximately 320 ng/microliter or 3.2 μg in the 10 microliters used in the assay). Then, a 10 μl aliquot of the diluted protein was mixed with undiluted serum. The mixture was incubated at 37° C. for 3 hours, which allows the protein to activate complement by forming a C3 convertase. The convertases formed were then able to activate C3 in the serum. Then, to measure the amount of complement activity left, the serum was diluted and mixed with antibody-sensitized sheep erythrocytes, which are easily lysed by complement when it is present in serum. This reaction was allowed to proceed for 30 minutes, and was stopped by diluting the mixture in cold buffer. The cells were centrifuged, and the lysed cells quantified by measuring the hemoglobin released. The results are shown in FIG. 4 and FIG. 9.

As expected, very small amounts of CVF were able to completely deplete the complement in human serum. 800 ng of either of the proteins HC3-1348 and HC3-1496 was able to completely deplete 10 µl of human serum. Other hybrid proteins were less active, requiring about 3-4 µg of protein to partially deplete 10 µl of human serum of complement. One hybrid protein, HC3-1550/1617 was apparently unable to deplete complement at the concentrations examined.

Unexpected was the observation that two of the proteins (HC3-1550 and HC3-1348) were actually able to deplete complement in guinea pig serum, although this activity was clearly less than that of CVF. Notably, preferred embodiments HC3-1550, HC3-1504, HC3-1496 and HC3-1348 were all able to deplete complement in human serum.

Factor B Activation Assay

This was an assay to measure the ability of a hybrid protein to activate factor B, and form a C3/C5 convertase. The convertase formation was measured as a function of the cleavage of factor B into Bb and Ba. In the assay, purified hybrid proteins were incubated with a three-fold excess of factor B and factor D (all highly purified) in the presence of magnesium at 37° C. At various times, aliquots of the reaction were withdrawn, and the reaction stopped by adding EDTA, which chelates the magnesium. The reaction products were run on a non-reducing SDS-polyacrylamide gel, which was stained for proteins with Coomassie Blue. The amount of Factor B converted was quantified by scanning the gel into a specialized computer program and measuring the amount of protein in the factor B and Bb bands.

Figure 5:
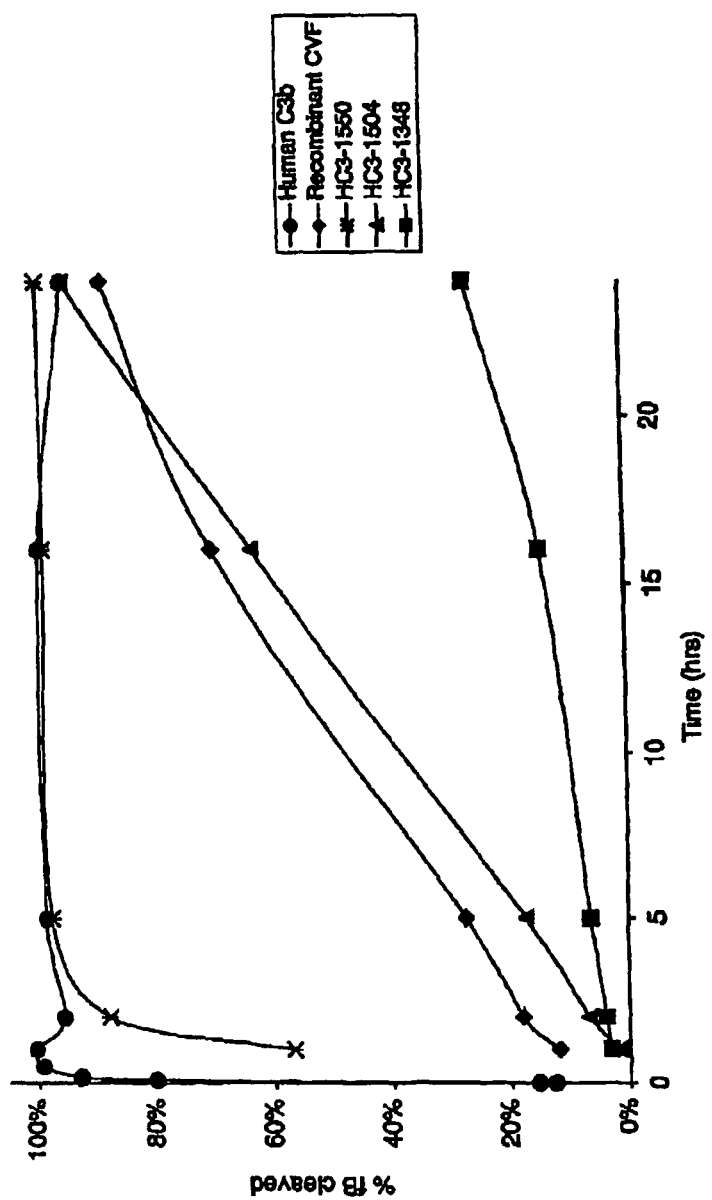
FIG. 5 shows results of an assay to measure the ability of the modified human C3 proteins (HC3-1348, HC3-1504, and HC3-1550) to activate factor B and to form a C3/C5 convertase as compared to CVF and C3b.
Figure 10:
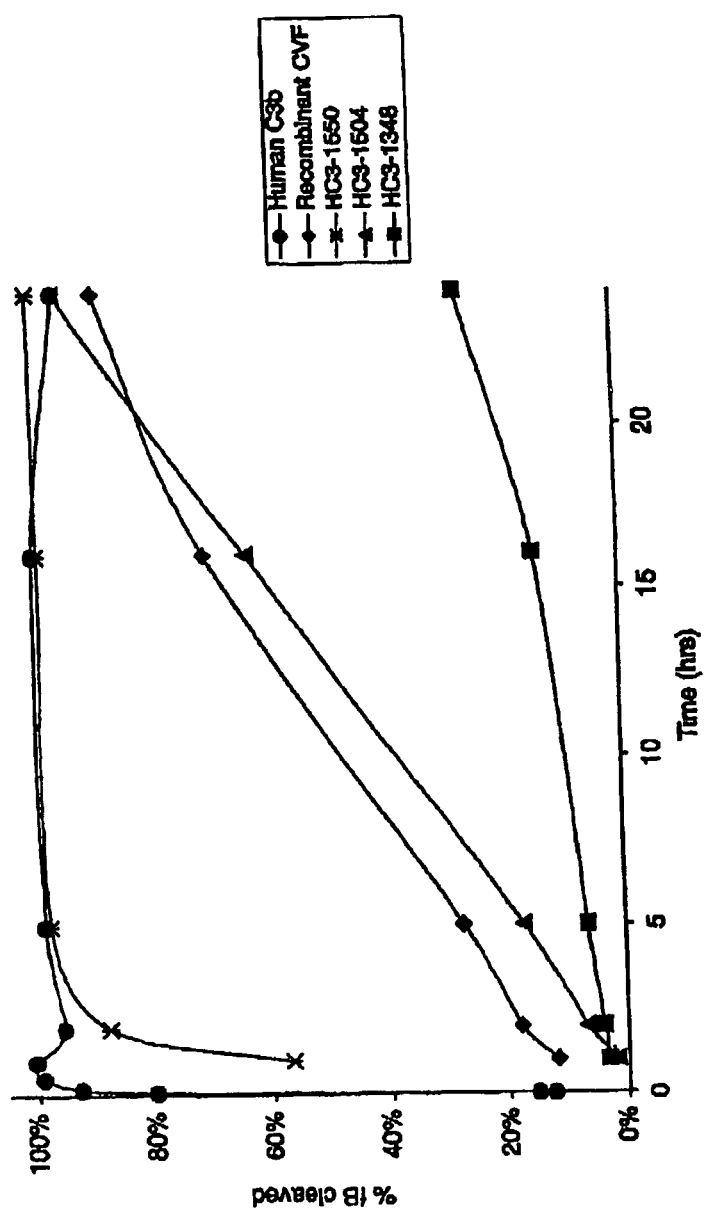
FIG. 10 is a graph showing the results of Cleavage of factor B by C3b, Recombinant CVF and a variety of modified human C3 proteins.

The results in FIGS. 5 and 10 show that Factor B was activated very rapidly in the presence of Human C3, for two reasons. Human C3 was able to bind factor B very rapidly, which makes it available for cleavage by factor D. However, the resulting convertase was very unstable, and falls apart rapidly, making the C3b available to bind more factor B. The reaction in the presence of CVF was much slower, which was a result of the lower affinity of CVF for factor B, and the greater stability of the CVF containing convertase. The conversion of factor B in the presence of HC3-1504 or HC3-1496 was quite similar to that of CVF. HC3-1550 and HC3-1550/1617 were able to convert factor B much more rapidly than CVF, but slower than C3b. This was probably a result of the convertase being less stable than the CVF containing enzyme, but more stable than the C3b containing convertase. In addition, it is likely that the initial binding of factor B by HC3-1550 is much more rapid than by CVF. Finally, HC3-1348 supports the cleavage of factor B less well than the other proteins discussed. This is probably a combination of the resulting convertase being more stable than the C3b containing enzyme, and the initial binding of factor B being less rapid.

C3 Convertase Activity Assay

This assay measures the activity of C3/C5 convertases containing hybrid proteins to activate human C3, by cleaving off the C3a peptide. To perform this assay, convertases were formed as described above, and the reaction stopped by the addition of EDTA. The convertase was then mixed with human C3, and the reaction incubated at 37° C. At the indicated times, aliquots were removed, and the reaction stopped by mixing with gel loading buffer containing SDS and β-mercaptoethanol. The SDS denatures the proteins, and the β-mercaptoethanol reduces the disulfide bonds between cysteines in the proteins. After electrophoresis under reducing conditions, the gel was stained with Coomassie Blue dye, and the relative amounts of the C3 α-chain and C3 α'-chain quantified as described above. Care was taken to use the same amount of convertase in each reaction.

Figure 6:
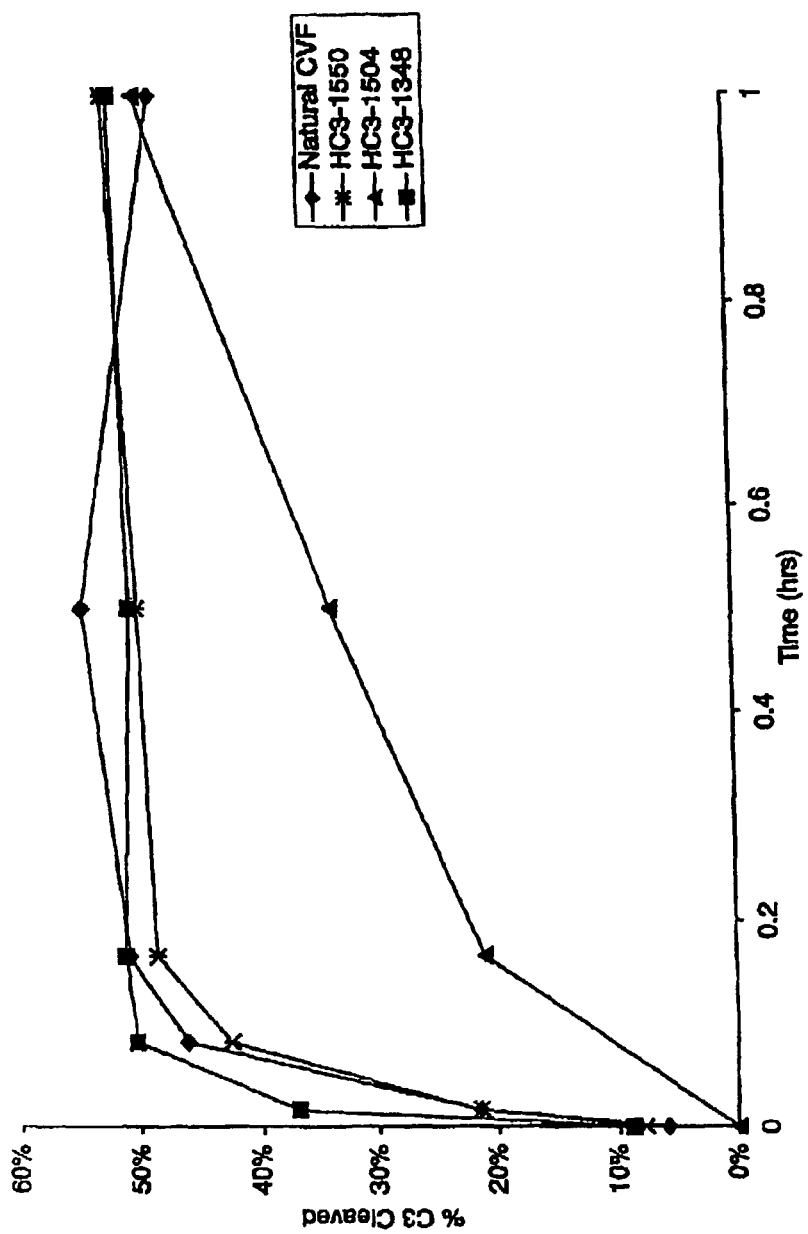
FIG. 6 shows results of an assay to measure the activity of C3/C5 convertase to activate C3 for the three modified human C3 proteins (HC3-1348, HC3-1504, and HC3-1550) as compared to CVF.
Figure 7:
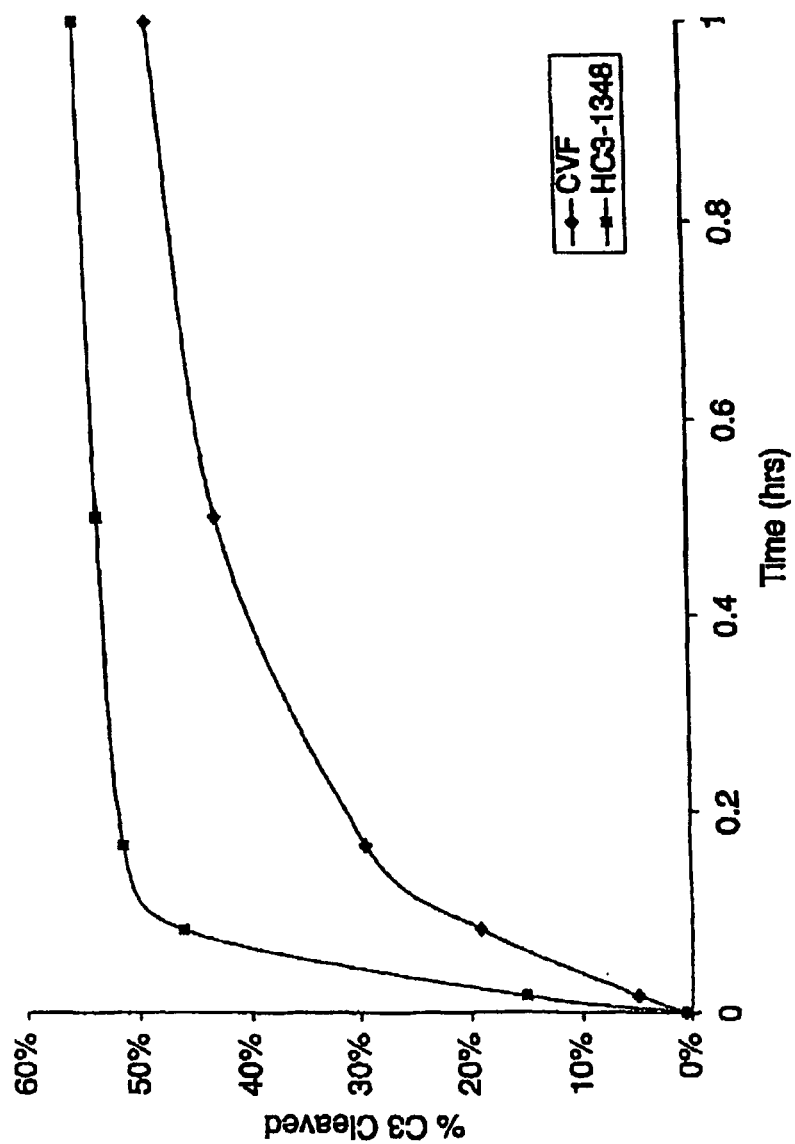
FIG. 7 shows results of an assay to measure C3 cleavage (using 20% of the amount of convertase used in the experiment in FIG. 6) of the modified human C3 protein HC3-1348 as compared to CVF.
Figure 11:
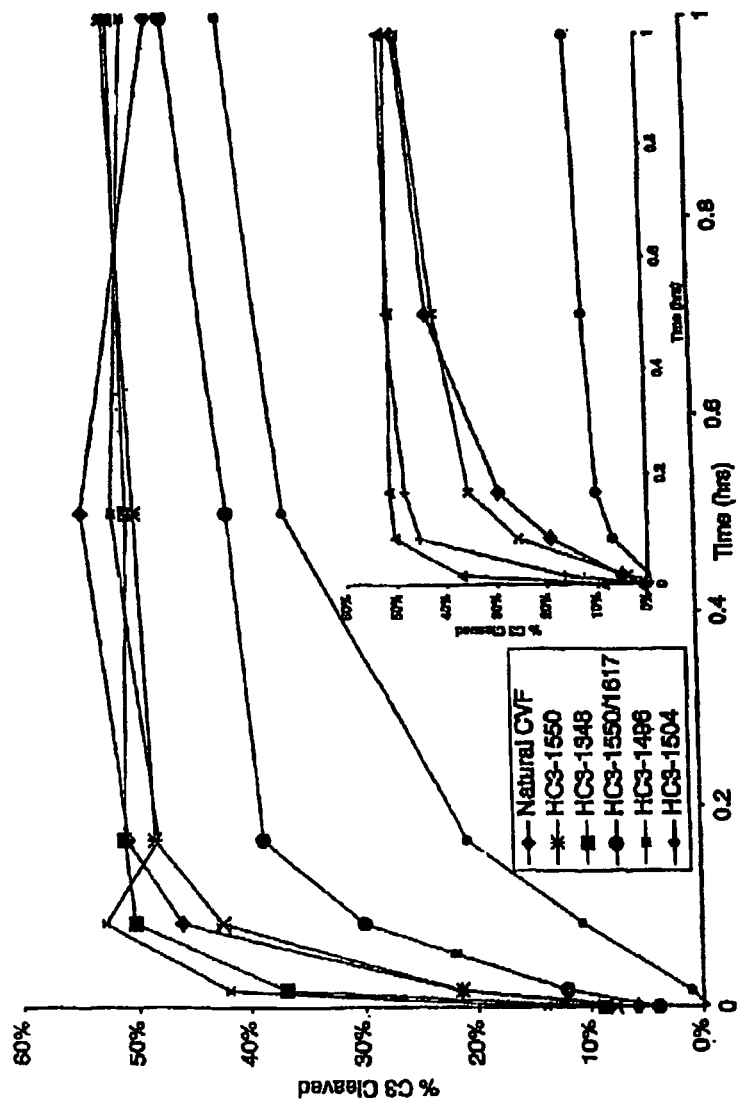
FIG. 11 is a graph showing the results of C3 cleavage of Natural CVF and a variety of modified human C3 proteins. The inset graph is of the same reaction performed using 20% of the convertase in the main graph.

FIG. 6 and FIG. 11 show that in this assay, CVF and HC3-1550 both were able to convert human C3 at approximately equal rates. HC3-1504 was markedly slower than CVF, but still was able to completely convert the amount of C3 present within one hour. HC3-1348 and HC3-1496 appeared to convert C3 at a rate faster than CVF, while HC3-1550/1617 appeared to convert C3 at an initially high rate which became slower after about 10 minutes. To further investigate this phenomenon, the C3 conversion assay was repeated, using all proteins except HC3-1504. In an effort to reduce the speed of the reaction, the amount of convertase present was reduced by a factor of five. These results are shown in FIG. 7 and in the insert of FIG. 11. In this assay, it was clear that the HC3-1348 and HC3-1496 formed convertases that were markedly efficient than CVF. HC3-1550/1617 formed a convertase that was initially active, but appears to become mostly inactive after about 10 minutes.

C5 Conversion Assay

The assay for C5 conversion activity was done essentially as described by Petrella et al., (1987) J. Immunol. Methods 104(1-2), 159-172, herein incorporated by reference in its entirety. In this assay, C5 convertase was formed as described above, using a total of 3 µg protein. After convertase formation, the reaction was stopped by the addition of EDTA to a final concentration of 5 mM. Then, 5 µl of this reaction was added to a 25 µl reaction containing 7 µg C5 in PBS. The reaction was incubated at 37° C. for 24 hours, and the reaction stopped by the addition of 7 µl Laemmli gel loading buffer, followed by boiling for 5 minutes. The reaction products were separated by reducing SDS-PAGE, and the gel was stained with Coomassie Blue dye, and the relative amounts of the C5 α-chain and C5 α'-chain quantified as described above. None of the current proteins are able to form an active C5 convertase.

The assay for degradation of the proteins by factors H and I was performed essentially according to the method of Oran and Isenman ((1999) J. Biol. Chem. 274 (8), 5120-5130, herein incorporated by reference in its entirety). In this method, 12 µg of each protein was incubated with 4.3 µg factor H and 0.3 µg factor I at 37° C. in a total volume of 60 µl. At the indicated times, 10 µl aliquots were withdrawn, and reactions stopped by the addition of 5 µl 5×Laemli gel loading buffer. Reaction products were separated by SDS-PAGE on a 4-20% gradient gel under reducing conditions. These data show that all proteins are partially resistant to digestion by factor I in the presence of factor H. In a similar assay, C3b was nearly digested to completion at the 0 timepoint.

Example 4

A Method for Depleting Complement Locally or Systemically

The modified human Complement C3 proteins produced by the methods disclosed herein are used to deplete complement locally or systemically as follows:

Local depletion is effected when the modified C3 proteins are administered locally to an organ, tissue, cavity, or intradermally. This results in a temporary and complete depletion of complement in the area. Alternatively, local depletion may use a specific monoclonal antibody which, when chemically attached to the modified C3, would localize it to a specific tissue, a disease site, or an infected cell to cause continuous depletion of complement in that area.

Systemic depletion is effected when the modified C3 proteins are administered systemically, for example, intravenously or intraperitoneally. This results in a temporary and complete depletion of complement systemically. This method can be used for reperfusion injury, coronary heart surgery, transplantation and/or systemic disease, particularly during a flare-up of symptoms or during episodical activity.

Some of the most advantageous qualities of the modified human C3 proteins used in each of these cases and in specific disease states can vary considerably. For example, in those cases for which an immediate, but temporary depletion of complement is desired, a modified protein having a shorter plasma half-life and/or lower stability, but high complement activation activity is preferred. In treating a chronic disease, a long plasma half-life and/or high stability, even if accompanied by a low or sluggish activity, would be preferred. Further, a modified C3 molecule that does not activate C5 can be particularly advantageous for certain therapies as it prevents the generation of the pro-inflammatory C5a anaphylatoxin.

Example 5

A Method for the Treatment of Reperfusion Injury

Examples of reperfusion injuries are tissue damage after the reopening of blocked vessels (e.g. after a heart attack or ischemic stroke), and reperfusion of a transplanted organ with a recipients' blood. For a clogged coronary artery or for reperfusion after organ transplantation, it can be desirable in many cases to deplete the complement before the transplant is reperfused or before the opening of the blocked vessel. The ability to avoid complement activation can avoid the tissue damage it causes, so the only remaining primary source of tissue damage is oxygen starvation. Typically, tissue damage due to complement activation during reperfusion is twice as great as tissue damage due to oxygen starvation—that is, roughly ⅔ of tissue damage is attributable to complement activation while ⅓ is attributable to oxygen starvation. Thus, reperfusion injury can be greatly diminished by depleting complement prior to reperfusion, as is possible with embodiments of the present invention. In this case it is preferable to use the highest activity convertase and to use a high dosage. The stability of the convertase is less important than it would be for a chronic disease.

In general terms, the methods of these embodiments of the invention involve administering an effective amount of a modified C3 protein systemically allowing enough time for depletion of complement, and then performing the surgery.

Example 6

A Method for Increasing the Effectiveness and/or Efficiency of Gene Therapy

This method relies on the depletion of complement in order to help prolong survival of a useful virus in the body. Because complement has been found to help the removal from the body of certain viral vectors used in gene therapy, it is desirable to reduce the amount of circulating complement prior to administration of a gene therapy vector. This may be done locally or systemically depending upon the type of gene therapy that is being used.

The method involves administering an effective amount of a modified C3 protein systemically or to the local area where the gene therapy is being administered, allowing time for depletion of complement, and then administering the gene therapy.

Example 7

A Method for Increasing Delivery of a Therapeutic (e.g. Chemotherapeutic) or Diagnostic Agent To increase the blood flow to an area where a therapeutic is being administered, a modified C3 protein is chemically linked to a monoclonal antibody with an affinity for the tissue of choice. In this example, the modified C3 is one that forms a highly active C3/C5 convertase. The modified C3/antibody is targeted to the tissue, resulting in local complement activation in the region, causing vessel permeability due to complement activation. The vessel permeability continues as long as the active convertase/antibody complexes are bound to the target, because new, non-activated complement is continually supplied by the blood arriving at the target.

For use of this method during the treatment of lung cancer, a modified C3 protein-monoclonal antibody hybrid is administered to a lung cancer patient, using a monoclonal antibody that recognizes a lung-specific antigen. The antibody binds to lung tissue and activates complement locally. This increases the vessel permeability in the lung, permitting the chemotherapeutic agent to more efficiently and effectively act on the lung cancer. As described above, this method permits continuous local activation of complement, which permits a persistent local elevation in blood-vessel permeability.

Example 8

A Method of Treating Rheumatoid Arthritis, Lupus, and Other Autoimmune or Immune Complex Diseases This method uses the example of rheumatoid arthritis as one of several conditions in which pain and inflammation arise from complement activation in a local area. For treatment, a modified C3 protein is administered systemically or locally, diminishing the complement response/activation by depleting the complement. This can reduce the symptoms of the disease and the progression of the disease. It can also be beneficial to have episodical depletion in combination with a longer term lowering of the activity of the complement system, especially when there are episodes of exacerbation of the symptoms of the disease. Further, this method can be used with other diseases with circulating immune complexes, such as lupus and other autoimmune diseases.

For example, when a complement-activating autoantibody is produced and is directed against the body's own proteins, the disease effect is primarily due to the binding of the antibody to the target causing complement activation and tissue damage as well as other interference with normal function. Myasthenia Gravis is an example of this type of disease. Autoantibody binds to the neuromuscular endplate where the nerve comes into contact with the muscle. Complement is activated and blocks the neurotransmitter, resulting in paralysis. Employing the method of this embodiment of the invention, the systemic depletion of complement, either continuously or during exacerbations in the disease, can markedly reduce symptoms and progression thereof.

Example 9

Method of Selecting a Modified C3 Protein

Various modified C3 proteins are useful for different diseases, and methods of treatment. Thus, it is useful to analyze the functional qualities of the modified C3 proteins of embodiments of the invention and to use them accordingly. The following methods are employed to analyze the function of purified modified C3 proteins produced as in Example 2.

The methods described herein, as well as others that are known to those of skill in the art, may be used.

Assays to Determine Convertase Activity.

In addition to the specific assays as mentioned below, two hemolytic assays for depletion of serum complement activity and induction of bystander lysis can be employed for screening.

Complement Depletion Assay.

To measure the anticomplementary (complement consumption) activity of modified C3 proteins, a small volume of human serum is incubated with CVF or hybrid proteins for three hours or shorter periods of time at 37° C. at a protein concentration of 5 µg/ml, to allow the proteins to deplete complement. The remaining complement hemolytic activity is subsequently measured using sensitized sheep erythrocytes using methods known to one of skill in the art including that of Cochrane et al., 1970 (Cochrane et al., 1970, *J. Immunol.* 117:6304, herein incorporated by reference in its entirety).

Bystander Lysis Assay.

The bystander lysis assay is performed by incubating 20 µl of normal guinea pig serum at 37° C. with 20 µl of CVF or hybrid proteins at a concentration of 5 µg/ml and 20 µl guinea pig erythrocytes ($5 \times 10^8$/ml). The CVF or hybrid proteins participate in fluid-phase activation of C5, which leads to lysis of the erythrocytes. Thus, presence of hemoglobin in the supernatant is indicative of C5 activation. The reaction is incubated at 37° C. for 30 minutes, and is stopped by the addition of 1 ml of cold buffer. After centrifugation, the released hemoglobin is measured spectrophotometrically. (Vogel, C. W., and Müller-Eberhard, H. J. (1984) *J. Immunol. Methods* 73(1), 203-220, herein incorporated by reference in its entirety).

C3 Convertase Formation/Factor B Activation.

To detect cleavage of Factor B into Ba and Bb, a hybrid protein (at 1 µM) is incubated for up to twenty four hours in the presence of a three-fold molar excess of Factor B and 0.5 µM of Factor D in the presence of $MgCl_2$ at 37° C. The reaction mixtures are analyzed by electrophoresis on 7.5% (w/v) SDS polyacrylamide gels under non-reducing conditions to monitor the disappearance of Factor B and the appearance of the cleavage products Ba and Bb. If necessary, a subsequent western blot can be performed to detect the Ba and Bb cleavage fragments. Controls can include native CVF, pro-CVF, cobra C3, iC3, human C3, iC3, C3b, and EDTA (Vogel and Müller-Eberhard, 1982, *J. Biol. Chem.* 257:8292-9, herein incorporated by reference in its entirety).

C3 Cleaving Activity.

To examine C3 cleaving activity, a C3 convertase is preformed as described herein, in reference to "C3 convertase formation/Factor B activation," using the hybrid proteins and human Factor B and Factor D. The convertase formation is stopped by the addition of EDTA, and purified human C3 is added The reaction mixture is incubated at 37° C. for one hour or for any other appropriate period of time. Aliquots are taken and immediately transferred into an ice water bath to stop further C3 activation. C3 cleavage is monitored by the disappearance of the C3 α-chain and appearance of the C3 α'-chain by running the reaction products on a 7.5% (w/v) SDS polyacrylamide gel under reducing conditions. If necessary, a subsequent western blot using anti-C3 antiserum is performed. Controls include native CVF, pro-CVF, and human and cobra iC3 or C3b (Vogel and Müller-Eberhard, 1982, *J. Biol. Chem.* 257:8292-9, herein incorporated by reference in its entirety).

C5 Cleaving Assay.

Figure 12:
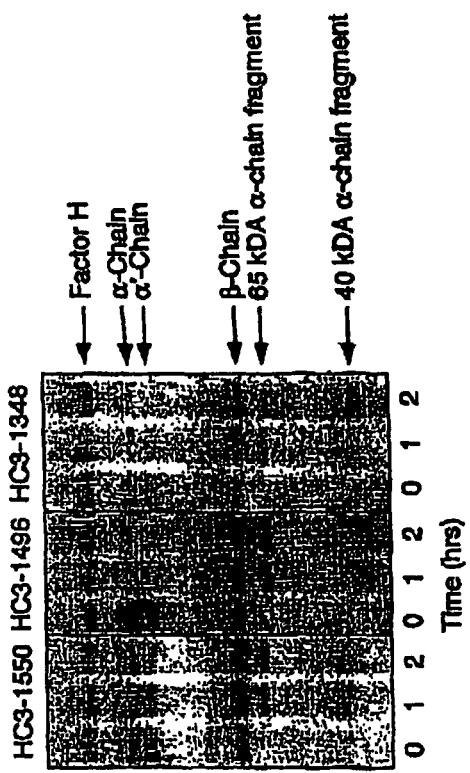
FIG. 12 is a graph showing the results of cleavage of selected hybrid proteins by factors H and I.
Figure 13:
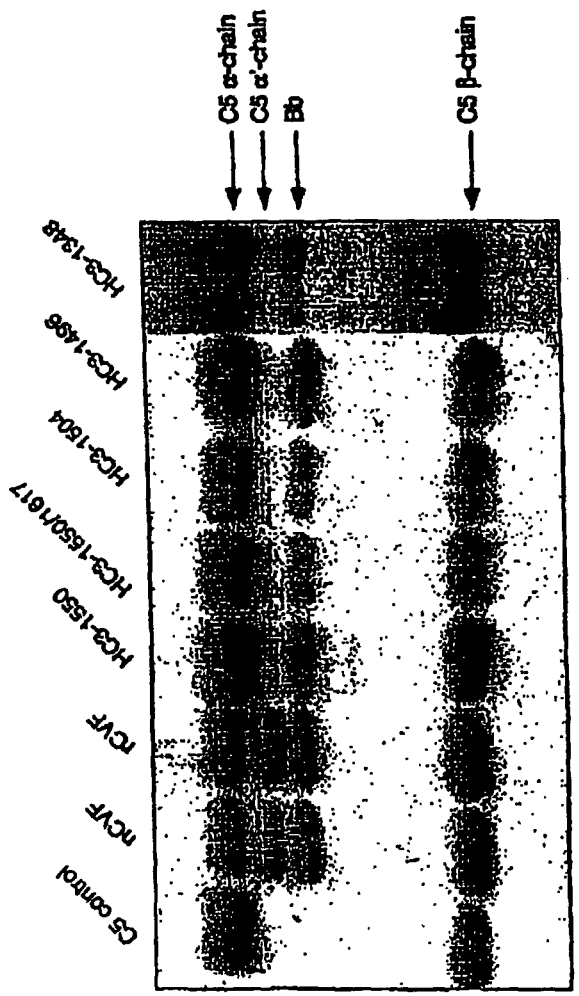
FIG. 13 is a picture of a gel showing the results of C5 conversion by Human C3/CVF hybrid proteins.

The C5 cleaving assay is performed as described above for the C3 cleaving assay using purified human C5 as substrate (Petrella et al., 1987, *J. Immunol.* 164:4742-4751, herein incorporated by reference in its entirety). See, for example, FIG. 12.

Assay for Convertase Stability.

Bimolecular convertases are pre-formed using the hybrid proteins and purified human Factor B and Factor D as described above. After addition of EDTA, the mixture is incubated at 37° C. and aliquots are removed over a period of 24 hours or shorter periods of time if appropriate, and each aliquot is immediately placed in an ice water bath. Subsequently, the C3 convertase activity is determined by the C3 cleaving assay described above. From the reduction of the C3 cleaving activity over time, the half-life of the spontaneous decay-dissociation of the various convertases is calculated. If insufficient quantities of hybrid proteins for this assay are available, the enzymatic activity is determined using the fluorogenic tripeptide t-butyloxy-carbonyl-leucyl-glycyl-arginyl-aminomethylcoumarin. (Caporale, L. H., Gabaer, S. S., Kell, W., and Gotze, O. 1981 J. Immunol. 126(5), 1963-1965, herein incorporated by reference in its entirety).

Assay for Factor H Binding.

Factor H binding to hybrid proteins is determined using an ELISA assay. Hybrid proteins are adsorbed onto microtiter plates. After blocking with ovalbumin and BSA, purified human Factor H at 10 µg/ml is added and incubated for 30 minutes at room temperature. After washing, bound Factor H is detected with anti-Factor-H antibody followed with an appropriate phosphatase-linked secondary antibody. If factor H can bind to the protein, an appropriate color change is observed. Controls can include native CVF, pro-CVF, cobra and human C3, as well as cobra and human iC3 (Alsenz et al., 1992, *Dev. Comp. Immunol.* 16:63-76, herein incorporated by reference in its entirety).

Assay for Factor I Cleavage.

Hybrid proteins are incubated with purified human Factor H and Factor I at 37° C. for several hours. The reactions are analyzed by subsequent 4-20% (w/v) SDS polyacrylamide gel electrophoresis under reducing conditions. Factor I activity is determined by the reduction in the strength of the 105 kDa α'-chain band, and appearance of bands with a molecular weight of 37 and 40 kDa. If necessary, a subsequent western blot is performed using anti-CVF and/or anti-C3 antibodies. Alternatively, hybrid proteins are labeled with $^{125}I$ using the iodogen method (Fraker and Speck, 1978). Cleavage products are detected after SDS polyacrylamide gel electrophoresis by autoradiography (Lambris et al., 1996, *J. Immunol.* 156:4821-32, herein incorporated by reference in its entirety). See, for example, FIG. 12.

Assays for Immunogenicity.

Various methods can be used to analyze immunogenicity, including but not limited to, skin tests, testing the modified C3 protein in transgenic animals which have been genetically engineered to have human immune systems, in vitro methods, including RIA tests using serum generated in such transgenic animals, Radioimmunoprecipitation assays, ELISA assays, Electrochemiluminescence, and Surface Plasmon Resonance. In addition, mouse, rate or guinea pig analogs of some proteins are constructed, using either mouse, rate or guinea pig C3 and CVF sequences. These are injected into the appropriate animal, and serum is collected and analyzed for the production of antibodies against the hybrid proteins.

Example 10

Method of Measuring Plasma Half-Life

There are many factors that can affect the plasma half-life of the modified C3 protein, including but not limited to specific antibodies produced by the immune system, proteases circulating within the serum, non-specific immune responses, and specific regulatory factors such as Factors H and I. In order for the modified C3 proteins to be able to activate and subsequently deplete complement, preferred C3 proteins will persist within human plasma for at least a minimum amount of time. Thus, it is of interest to identify the plasma half-life of the modified C3 proteins to determine how useful they will be for treatment of certain diseases.

This method measures the stability of the modified C3 protein in plasma in three ways. However it is to be understood that one or all of the methods can be used as well as any other methods known to one of skill in the art.

The first method measures the stability in serum in vitro. Human serum is isolated and separated from the whole blood of a patient. Aliquots of different concentrations of the modified C3 proteins are added to the serum and allowed to incubate. Aliquots of the serum are removed at various time intervals and the amount of modified C3 that persists is identified in an ELISA assay using a monoclonal antibody which is specific to C3.

A second method allows for the identification of stability in serum in a humanized animal. The modified C3 protein is administered to the animal and blood samples are taken over time. The amount of modified C3 protein is identified in an ELISA assay using specific antibodies to the protein.

A third method allows for the identification of stability in a human patient. The modified C3 is administered to the patient and blood samples are removed over time. The amount of modified C3 protein is identified using an ELISA assay. This will give a clear indication of how long the modified C3 protein circulates within the plasma of a patient.

In some embodiments, the antibody that is used need not be specific for the modified C3. For example, antibodies that recognize normal C3 can be tested and used to identify the modified C3 in an ELISA procedure.

Example 11

C3 Convertase Formation of Modified Human Complement C3 Proteins as Measured Using Surface Plasmon Resonance Table 2 shows relative binding of complement proteins to C3, CVF, and recombinant human C3/CVF proteins. In all cases, a higher number indicates that the protein interaction is tighter. The proteins (C3b, etc.) were bound to a BIACORE CHIP™, and then contacted with complement factors. The amount of each of the complement factors bound to the chip (and thus bound to the modified C3 proteins) was determined by surface plasmon resonance. The results showed that: 1) Neither of the recombinant proteins bound C5, consistent with the inability to form a convertase capable of cleaving C5. 2) Both proteins bound factor H, though CVF does not. Factor H is one of the regulatory proteins that is capable of dissociating the C3b,Bb convertase complex and directing a second complement protein, factor I, to inactivate C3b through cleavage. 3) The affinity of the proteins for factor B in the presence of factor D and magnesium was approximately proportional to the rate the proteins were able to form a C3 convertase (as measured by their ability to mediate factor B cleavage—see FIG. 10). Both HC3-1550 and HC3-1348 were cleaved but slower than C3b. CVF is not cleaved at all by H or I, because natural CVF has no H or I sites. It is interesting that recombinant CVF, a 2 chain molecule, has 2 or 3 I sites, but is still not cleaved by factor I.

TABLE 2

Relative binding of Complement proteins to C3, CVF, and recombinant human C3/CVF proteins.

| Protein on Chip | Amount of protein bound (RU)-2nd column corrected for MW C5 | Factor H | Factor B (in EDTA) | Factor B (with Mg) | Factor B (with fD and Mg) |
|---|---|---|---|---|---|
| C3b | 607 | 646 | 243 | 285 | 625 |
| HC3-1550 | 66 | 550 | 9 | 264 | 340 |
| HC3-1348 | 18 | 219 | 5 | 276 | 162 |
| CVF | 617 | −14 | 99 | 298 | 370 |

Table 3 shows the stability of the C3 convertases formed by the modified human Complement C3 proteins as measured by surface plasmon resonance on a BIACORE machine at 25° C. The results showed that both proteins were able to form C3 convertases that were substantially more stable than the C3b-containing convertase. The table also shows that the HC3-1348-containing convertase was actually more stable than the CVF-containing enzyme. These results are consistent with other measurements of half life at higher temperatures which showed that CVF had a half life of 7 hours at 37° C. and C3b had a half life of 1.5 minutes at 37° C.

TABLE 3

C3 convertase formation

| Protein on Chip | T½ of C3 convertase (min) |
|---|---|
| C3b | 4.3 |
| HC3-1550 | 119.3 |
| HC3-1348 | 1720.0 |
| CVF | 1100.0 |

Example 12

Factor B Cleavage of Modified Human Complement C3 Proteins

The factor B cleavage graph in FIG. 10 shows a time course of the ability of the modified human complement C3b proteins to mediate the cleavage of factor B in the presence of magnesium ion and factor D. This can be used to measure the ability of the protein to form a C3/C5 convertase. Of note in this assay was that C3b formed a convertase very efficiently, both because it bound factor B very efficiently in the presence of factor D and magnesium (see the data in Example 11), and because the resulting complex was very unstable. CVF, HC3-1496 and HC3-1504 all formed a convertase at approximately the same rate, while HC3-1550 and HC3-1550/1617 were intermediate between C3b and CVF in their ability to form a convertase. HC3-1348 was very slow to bind factor B. This is most probably explained by a combination of a longer half-life of the convertase once formed and a lower affinity of the hybrid protein for factor B.

Example 13

C3 Cleavage of Modified Human Complement C3 Proteins

FIG. 11 shows the ability of the convertases to cleave C3, and shows a time course of the cleavage reaction. The inset is a time course performed with 20% of the convertase used in the main graph. The results showed that CVF and HC3-1550 formed convertases that were approximately equally efficient at C3 cleavage, while HC3-1348 and HC3-1496 both formed convertases that were approximately 5-fold more efficient than CVF at cleaving C3. It is interesting that the HC3-1550/1617-containing convertase appeared to be quite unstable, and did not support C3 cleavage after about 10 minutes.

Example 14

Complement Depletion of Modified Human Complement C3 Proteins

Figure 9:
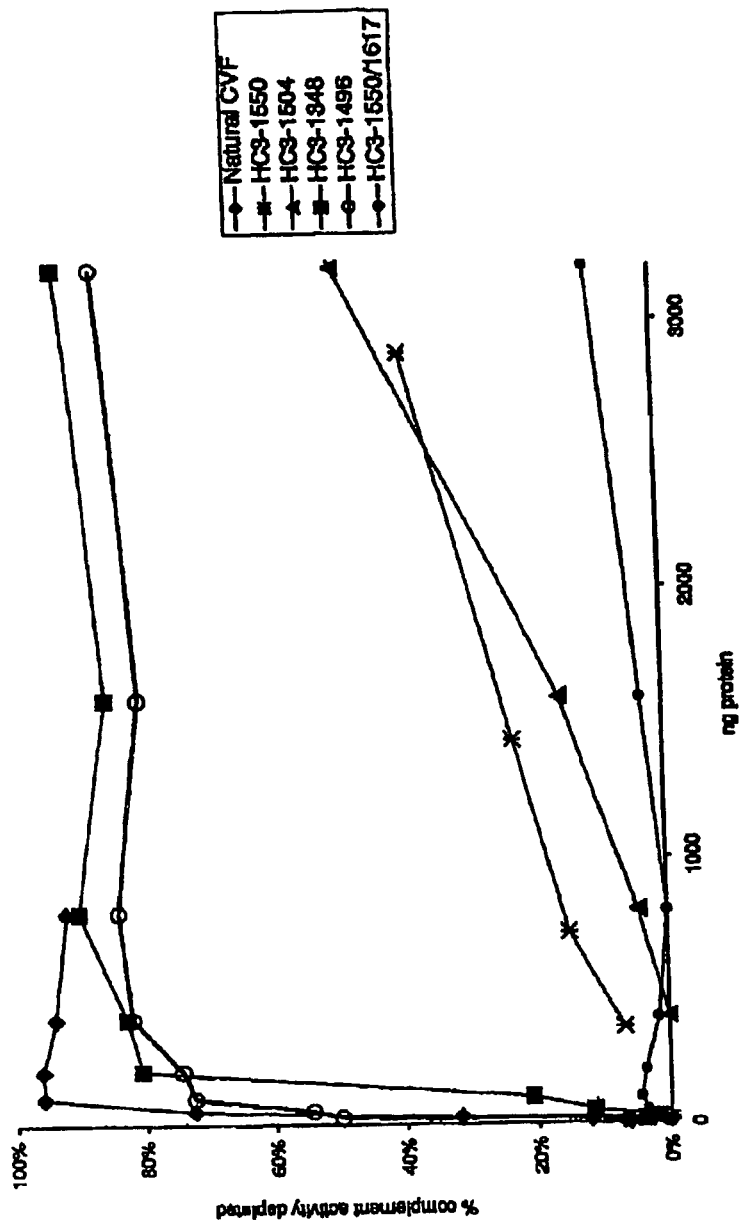
FIG. 9 is a graph showing the results of complement depletion of Natural CVF and a variety of human C3 proteins.

The data in the complement depletion chart in FIG. 9 show that all proteins except HC3-1550/1617 were able to deplete complement, though with very different efficiencies. Both HC3-1550 and HC3-1504 were quite inefficient at the depletion of complement, while HC3-1496 and HC3-1348 were able to deplete complement quite efficiently, though not quite as well as natural or recombinant CVF. HC3-1348 was formerly referred to as HC3-1325 in a previous application, but substitution mapping has subsequently shown that the substitution was at 1348 rather than 1325.

In conclusion, HC3-1496 is an interesting protein because, although it only has an insert 8 amino acids longer than HC3-1504, it acts much more like HC3-1348 with respect to complement depletion and C3 cleavage and more like HC3-1504 with respect to factor B cleavage. It forms a convertase as well as HC3-1504 or CVF, but the resulting convertase is more active at cleaving C3.

HC31550/1617 was made by replacing the region from 1550 to the end of C3 with the CVF region, then taking away the last 46 amino acids and replacing them with C3. This chimeric molecule showed no complement depletion, formed a C3 convertase as well as HC3-1550, and the C3 convertase formed was nearly as active as HC3-550, but had an apparently shorter half-life.

Example 15

Methods of Producing Variants in the Modified C3 Proteins

Variants of the modified C3 proteins are produced that have advantageous qualities. By advantageous it is meant that the variants enhance one or more activities of the protein, including but not limited to: C3 convertase activity, serum decomplementation, factor B binding, cleavage of C3, Binding of Bb and Binding of C3. The variants can include one or more mutations in each region and can include one or more amino acids. Some specific variants are set out below:

Because the C-terminus is involved in stabilization of the C3 convertase, mutations are produced in the C-terminus (after aa 1617) of any modified C3 proteins. The mutations can be insertions, deletions, and substitutions. However, the mutations are preferably substitutions. The mutations stabilize the C3 convertase. Examples of mutations at the C terminus include but are not limited to: mutations at positions 1633, 1654, and 1658. Non-conservative as well as conservative mutations, in addition to amino acid changes that affect the conformation, are included among the embodiments. However, preferably the mutations result in a non-conservative amino acid change.

There are three changes between CVF and human C3 in the span of 1496 and 1504 (8 amino acid residues) that appear to be responsible for a large change in the activity of the convertase. Thus, mutations between positions 1496 and 1504 of any of the modified C3 proteins are included that result in increased activity of the convertase in cleaving C3 and/or in decomplementing serum. The mutations can be changes to one or more amino acids within that region. Preferably, the mutations are substitutions of one or more amino acids in that region, in particular, mutations that result in non-conservative amino acid changes.

Mutations between positions 1348 and 1496 in any modified C3 protein are produced that modify the ability of the protein to bind factor B (and specifically, the ability for C3b and factor B to bind), preferably the modification results in an increased ability to bind to factor B. Whole regions from CVF are switched out to C3 and vice versa. Further mutations are included that result in amino acid substitutions. More specifically, the regions from 1367-1379 are switched for CVF and for C3 and specific amino acids within this region are substituted.

Sequence changes in the region of around 1550 in CVF and 1570-1584 in C3 that may be responsible for the activity of the C3 convertase in cleaving C3, either from binding Bb or binding the target C3 molecule. Using CVF/cobra C3 substitutions, a series of 4 amino acid residues were identified (Q1550G, E1554R, P1556A and R1557Q-positions numbered according to CVF sequence numbering) that resulted in a protein with a much lower activity in cleaving C3. Therefore, variants are produced in the amino acids from position 1570-1584 that result in an increased activity of the C3 convertase in cleaving C3 for the modified C3 proteins. The variants are preferably amino acid substitutions of one or more amino acids in that region.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be combined and/or exchanged by one of ordinary skill in this art to perform methods in accordance with principles described herein. Each patent, journal reference, and the like, cited herein is hereby incorporated by reference in its entirety.

Although the invention has been disclosed in the context of certain embodiments and examples, it is understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A modified human complement C3 protein consisting of SEQ ID NO:2 with a substitution of a portion of a human C3 protein (SEQ ID NO:2) with a corresponding portion of a Cobra Venom Factor (CVF) protein (SEQ ID NO:4), wherein the substitution is selected from the group consisting of: amino acids 1550-1663 of human C3 (SEQ ID NO:2) substituted with amino acids 1529-1642 of CVF (SEQ ID NO:4), amino acids 1504-1663 of human C3 (SEQ ID NO:2) substituted with amino acids 1484-1642 of CVF (SEQ ID NO:4), amino acids 1348-1663 of human C3 (SEQ ID NO:2) substituted with amino acids 1330-1642 of CVF (SEQ ID NO:4), amino acids 1550-1617 of human C3 (SEQ ID NO:2) substituted with amino acids 1529-1596 of CVF (SEQ ID NO:4), amino acids 1504-1617 of human C3 (SEQ ID NO:2) substituted with amino acids 1484-1642 of CVF (SEQ ID NO:4), and amino acids 1496-1663 of human C3 (SEQ ID NO:2) substituted with amino acids 1475-1642 of CVF (SEQ ID NO:4).

2. The modified C3 protein of claim 1, wherein the substitution is amino acids 1550-1663 of the human C3 protein (SEQ ID NO:2) substituted with amino acids 1529-1642 of CVF (SEQ ID NO:4).

3. The modified C3 protein of claim 1, wherein the substitution is amino acids 1504-1663 of the human C3 protein (SEQ ID NO:2) substituted with amino acids 1484-1642 of CVF (SEQ ID NO:4).

4. The modified C3 protein of claim 1, wherein the substitution is amino acids 1348-1663 of the human C3 protein (SEQ ID NO:2) substituted with amino acids 1330-1642 of CVF (SEQ ID NO:4).

5. The modified C3 protein of claim 1, wherein the substitution is amino acids 1496-1663 of the human C3 protein (SEQ ID NO:2) substituted with amino acids 1475-1642 of CVF (SEQ ID NO:4).

6. The modified C3 protein of claim 1, wherein the modified C3 protein has an affinity for factor B and supports formation of an active convertase.

7. The modified C3 protein of claim 6, wherein the convertase has an intrinsic half-life of at least about 15 minutes at 37° C.

8. The modified C3 protein of claim 1, wherein the modified protein is less immunogenic than CVF.

9. A composition comprising the modified human complement C3 protein of claim 1 and a pharmaceutically acceptable carrier.

10. The modified C3 protein of claim 6, wherein the resulting convertase is capable of cleaving C3, but is not capable of cleaving C5.

11. The modified C3 protein of claim 1, wherein the modified C3 protein has modified affinity for factor B and/or factor D.

12. The modified C3 protein of claim 5, wherein the modified C3 protein has an affinity for factor B and supports formation of an active convertase.

13. The modified C3 protein of claim 12, wherein the resulting convertase is capable of cleaving C3, but is not capable of cleaving C5.

14. The modified C3 protein of claim 12, wherein the convertase has an intrinsic half-life of at least about 15 minutes at 37° C.

15. The modified C3 protein of claim 5, wherein the modified protein is less immunogenic than CVF.

16. The modified C3 protein of claim 5, wherein the modified C3 protein has modified affinity for factor B and/or factor D.

17. A composition comprising the modified human complement C3 protein of claim 5 and a pharmaceutically acceptable carrier.

18. A modified human complement C3 protein consisting of SEQ ID NO:2 with a substitution of a portion of a human C3 protein (SEQ ID NO:2) with a corresponding portion of a Cobra Venom Factor (CVF) protein (SEQ ID NO:4), wherein the modified human complement C3 protein has an additional 1 to 19 amino acids at the N-terminus that are not encoded by a human C3 protein or a CVF protein; wherein the substitution of the human C3 protein is selected from the group consisting of: amino acids 1550-1663 of human C3 (SEQ ID NO:2) substituted with amino acids 1529-1642 of CVF (SEQ ID NO:4), amino acids 1504-1663 of human C3 (SEQ ID NO:2) substituted with amino acids 1484-1642 of CVF (SEQ ID NO:4), amino acids 1348-1663 of human C3 (SEQ ID NO:2) substituted with amino acids 1330-1642 of CVF (SEQ ID NO:4), amino acids 1550-1617 of human C3 (SEQ ID NO:2) substituted with amino acids 1529-1596 of CVF (SEQ ID NO:4), amino acids 1504-1617 of human C3 (SEQ ID NO:2) substituted with amino acids 1484-1642 of CVF (SEQ ID NO:4), and amino acids 1496-1663 of human C3 (SEQ ID NO:2) substituted with amino acids 1475-1642 of CVF (SEQ ID NO:4).

19. The method modified C3 protein of claim 18, wherein the additional 1 to 19 amino acids at the N-terminus of the modified human C3 protein is a 19 amino acid sequence consisting of the amino acid sequence of SEQ ID NO:5.

20. The modified C3 protein of claim 19, wherein the substitution is amino acids 1496-1663 of the human C3 protein (SEQ ID NO:2) substituted with amino acids 1475-1642 of CVF (SEQ ID NO:4).

21. A method for depleting complement, comprising administering the modified C3 protein of claim 1 to a patient in an amount effective for the depletion of complement.

22. The method of claim 21, wherein the administration is a local administration, and said local administration is selected from the group consisting of administration into an organ, into a cavity, into a tissue, and subcutaneous administration.

23. The method of claim 21, wherein the administration is a systemic administration, and said systemic administration is intravenous or intraperitoneal administration.

24. A method of treating a condition or disease associated with undesirable complement activation, comprising administering the modified C3 protein of claim 1 in an amount sufficient to deplete complement.

25. The method of claim 24, wherein the condition or disease is selected from the group consisting of rheumatoid arthritis, myocardial ischemia, reperfusion, cardiopulmonary bypass, myocardial infarction, and angioplasty.

26. A method for avoiding or ameliorating reperfusion injury in a patient, comprising: delivering the modified C3 protein of claim 1 to the patient in an amount sufficient to deplete complement; and permitting reperfusion in the patient.

27. A method for depleting complement, comprising administering the modified C3 protein of claim 5 to a patient in an amount effective for the depletion of complement.

28. The method of claim 27, wherein the administration is a local administration, and said local administration is selected from the group consisting of administration into an organ, into a cavity, into a tissue, and subcutaneous administration.

29. The method of claim 27, wherein the administration is a systemic administration, and said systemic administration is intravenous or intraperitoneal administration.

30. A method for avoiding or ameliorating reperfusion injury in a patient, comprising: delivering the modified C3 protein of claim 5 to the patient in an amount sufficient to deplete complement; and permitting reperfusion in the patient.

31. A method of increasing delivery of a therapeutic or diagnostic agent in a patient, comprising: delivering the modified C3 protein of claim 5 to the patient in an amount sufficient to increase blood flow; and providing the therapeutic or diagnostic agent.

32. A method of treating a condition or disease associated with undesirable complement activation in a patient, comprising administering the modified C3 protein of claim 5 to the patient in an amount sufficient to deplete complement.

33. The method of claim 32, wherein the condition or disease is selected from the group consisting of rheumatoid arthritis, myocardial ischemia, reperfusion, cardiopulmonary bypass and myocardial infarction.

* * * * *